(12) United States Patent
Umeda et al.

(10) Patent No.: US 12,186,345 B2
(45) Date of Patent: Jan. 7, 2025

(54) CELL POPULATION INCLUDING ADHESIVE STEM CELLS, PRODUCTION METHOD THEREFOR AND PHARMACEUTICAL COMPOSITION

(71) Applicant: KANEKA CORPORATION, Osaka (JP)

(72) Inventors: Nobuyoshi Umeda, Kobe (JP); Keita Ino, Kobe (JP); Chiho Kobayashi, Kobe (JP)

(73) Assignee: KANEKA CORPORATION, Osaka (JP)

( * ) Notice: Subject to any disclaimer, the term of this patent is extended or adjusted under 35 U.S.C. 154(b) by 1170 days.

(21) Appl. No.: 16/957,896

(22) PCT Filed: Dec. 28, 2018

(86) PCT No.: PCT/JP2018/048540
§ 371 (c)(1),
(2) Date: Jun. 25, 2020

(87) PCT Pub. No.: WO2019/132026
PCT Pub. Date: Jul. 4, 2019

(65) Prior Publication Data
US 2020/0368291 A1    Nov. 26, 2020

(30) Foreign Application Priority Data

Dec. 28, 2017  (JP) ................ 2017-253879

(51) Int. Cl.
*A61K 35/545*   (2015.01)
*C12N 5/0775*   (2010.01)

(52) U.S. Cl.
CPC .......... *A61K 35/545* (2013.01); *C12N 5/0665* (2013.01)

(58) Field of Classification Search
CPC .... A61K 35/545; A61K 9/0019; A61K 35/28; C12N 5/0665; C12N 5/0605; C12N 2500/99; C12N 2502/115; C12N 15/09; A61P 1/04; G01N 2800/065; G01N 2800/245; G01N 33/56966; C07K 14/47
See application file for complete search history.

(56) References Cited

FOREIGN PATENT DOCUMENTS

| CN | 101316602 A | * 12/2008 | ........... A61K 31/738 |
|----|-------------|-----------|------------------------|
| CN | 105765060 A | 7/2016 | |
| EP | 3 037 523 A1 | 6/2016 | |
| JP | 2005-151907 A | 6/2005 | |
| JP | 2010-527629 A | 8/2010 | |
| WO | WO 2008/146992 A1 | 12/2008 | |

OTHER PUBLICATIONS

Martinelli et al. A humanized system to expand in vitro amniotic fluid-derived stem cells intended for clinical application; Cytotherapy, 2016; 18: 438-451 (Year: 2016).*
Office Action issued Jan. 9, 2023, in Chinese Patent Application No. 201880084442.5.
Japanese Office Action for corresponding Japanese Application No. 2019-562519, dated Jun. 13, 2023.
Barkholt et al., "Risk of tumorigenicity in mesenchymal stromal cell-based therapies-Bridging scientific observations and regulatory viewpoints", Cytotherapy, 2013, vol. 15, pp. 753-759.
International Search Report (PCT/ISA/210) issued in PCT/JP2018/048540 mailed on Apr. 9, 2019.
Lankford et al., "Manufacture and preparation of human placenta-derived mesenchymal stromal cells for local tissue delivery", Cytotherapy, 2017, vol. 19, No. 6, pp. 680-688, whole article, abstract, p. 683, left column, fig. 21.
Stultz et al., "Chromosomal Stability of Mesenchymal Stromal Cells During In Vitro Culture", Cytotherapy, 2016, vol. 18, No. 3, pp. 336-343.
Written Opinion (PCT/ISA/237) issued in PCT/JP2018/048540 mailed on Apr. 9, 2019.
Chinese Office Action for Chinese Application No. 201880084442. 5, dated Sep. 28, 2023.
Zongliu, "Basic Clinical Application of Domestic Adult Stem Cells", Yunnan Science and Technology Press, Aug. 2016, pp. 3-8 (20 pages total), with an English translation.
Chevallier et al., "Osteoblastic differentiation of human mesenchymal stem cells with platelet lysate," Biomaterials (2010), vol. 31, pp. 270-278.
Extended European Search Report issued Oct. 11, 2021, in European Patent Application No. 18893991.2.

* cited by examiner

*Primary Examiner* — Christopher M Babic
*Assistant Examiner* — Masudur Rahman
(74) *Attorney, Agent, or Firm* — Birch, Stewart, Kolasch & Birch, LLP

(57) ABSTRACT

An object of the present invention is to provide a cell population comprising safe adherent stem cells maintaining a normal karyotype and a method for producing the cell population, and a pharmaceutical composition comprising the cell population. According to the present invention, a production method of a cell population comprising adherent stem cells, comprising obtaining a cell population in which the proportion of KCNAB1-positive adherent stem cells in the cell population is 85% or more, is provided.

9 Claims, 1 Drawing Sheet
Specification includes a Sequence Listing.

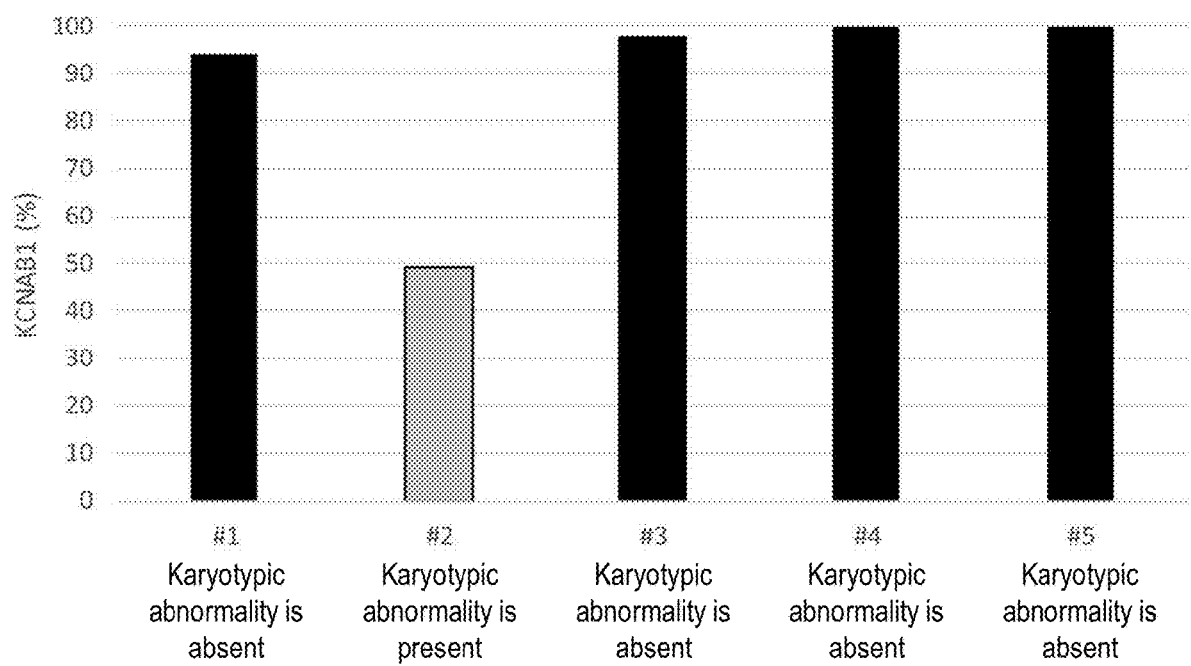

SEQUENCE LISTING

```
<160> NUMBER OF SEQ ID NOS: 10

<210> SEQ ID NO 1
<211> LENGTH: 1851
<212> TYPE: DNA
<213> ORGANISM: Homo sapiens
<220> FEATURE:
<221> NAME/KEY: CDS
<222> LOCATION: (1)..(1851)

<400> SEQUENCE: 1 atg tcg ggg gtc cgg ggc ctg tcg cgg ctg ctg agc gct cgg cgc ctg      48
Met Ser Gly Val Arg Gly Leu Ser Arg Leu Leu Ser Ala Arg Arg Leu
1               5                   10                  15 gcg ctg gcc aag gcg tgg cca aca gtg ttg caa aca gga acc cga ggt      96
Ala Leu Ala Lys Ala Trp Pro Thr Val Leu Gln Thr Gly Thr Arg Gly
            20                  25                  30 ttt cac ttc act gtt gat ggg aac aag agg gca tct gct aaa gtt tca     144
Phe His Phe Thr Val Asp Gly Asn Lys Arg Ala Ser Ala Lys Val Ser
        35                  40                  45
```

| | | |
|---|---|---|
| gat tcc att tct gct cag tat cca gta gtg gat cat gaa ttt gat gca<br>Asp Ser Ile Ser Ala Gln Tyr Pro Val Val Asp His Glu Phe Asp Ala<br>50                       55                  60 | | 192 |
| gtg gtg gta ggc gct gga ggg gca ggc ttg cga gct gca ttt ggc ctt<br>Val Val Val Gly Ala Gly Gly Ala Gly Leu Arg Ala Ala Phe Gly Leu<br>65                       70                  75                  80 | | 240 |
| tct gag gca ggg ttt aat aca gca tgt gtt acc aag ctg ttt cct acc<br>Ser Glu Ala Gly Phe Asn Thr Ala Cys Val Thr Lys Leu Phe Pro Thr<br>                       85                  90                  95 | | 288 |
| agg tca cac act gtt gca gca cag cta gaa aat tat ggc atg ccg ttt<br>Arg Ser His Thr Val Ala Ala Gln Leu Glu Asn Tyr Gly Met Pro Phe<br>                100                  105                110 | | 336 |
| agc aga act gaa gat ggg aag att tat cag cgt gca ttt ggt gga cag<br>Ser Arg Thr Glu Asp Gly Lys Ile Tyr Gln Arg Ala Phe Gly Gly Gln<br>              115                  120                125 | | 384 |
| agc ctc aag ttt gga aag ggc ggg cag gcc cat cgg tgc tgc tgt gtg<br>Ser Leu Lys Phe Gly Lys Gly Gly Gln Ala His Arg Cys Cys Cys Val<br>130                      135                140 | | 432 |
| gct gat cgg act ggc cac tcg cta ttg cac acc tta tat gga agg tct<br>Ala Asp Arg Thr Gly His Ser Leu Leu His Thr Leu Tyr Gly Arg Ser<br>145                      150                  155                160 | | 480 |
| ctg cga tat gat acc agc tat ttt gtg gag tat ttt gcc ttg gat ctc<br>Leu Arg Tyr Asp Thr Ser Tyr Phe Val Glu Tyr Phe Ala Leu Asp Leu<br>                       165                  170                175 | | 528 |
| ctg atg gag aat ggg gag tgc cgt ggt gtc atc gca ctg tgc ata gag<br>Leu Met Glu Asn Gly Glu Cys Arg Gly Val Ile Ala Leu Cys Ile Glu<br>                    180                  185                190 | | 576 |
| gac ggg tcc atc cat cgc ata aga gca aag aac act gtt gtt gcc aca<br>Asp Gly Ser Ile His Arg Ile Arg Ala Lys Asn Thr Val Val Ala Thr<br>                195                  200                205 | | 624 |
| gga ggc tac ggg cgc acc tac ttc agc tgc acg tct gcc cac acc agc<br>Gly Gly Tyr Gly Arg Thr Tyr Phe Ser Cys Thr Ser Ala His Thr Ser<br>210                      215                  220 | | 672 |
| act ggc gac ggc acg gcc atg atc acc agg gca ggc ttt cct tgc cag<br>Thr Gly Asp Gly Thr Ala Met Ile Thr Arg Ala Gly Leu Pro Cys Gln<br>225                      230                  235                240 | | 720 |
| gac cta gag ttt gtt cag ttc cac cct aca ggc ata tat ggt gct ggt<br>Asp Leu Glu Phe Val Gln Phe His Pro Thr Gly Ile Tyr Gly Ala Gly<br>                       245                  250                255 | | 768 |
| tgt ctc att acg gaa gga tgt cgt gga gag gga ggc att ctc att aac<br>Cys Leu Ile Thr Glu Gly Cys Arg Gly Glu Gly Gly Ile Leu Ile Asn<br>                    260                  265                270 | | 816 |
| agt caa ggc gaa agg ttt atg gag cga tac gcc cct gtc gcg aag gac<br>Ser Gln Gly Glu Arg Phe Met Glu Arg Tyr Ala Pro Val Ala Lys Asp<br>                275                  280                285 | | 864 |
| ctg gcg tct aga gat gtg gtg tct cgg tcc atg act ctg gag atc cga<br>Leu Ala Ser Arg Asp Val Val Ser Arg Ser Met Thr Leu Glu Ile Arg<br>290                      295                  300 | | 912 |
| gaa gga aga ggc tgt ggc cct gag aaa gat cac gtc tac ctg cag ctg<br>Glu Gly Arg Gly Cys Gly Pro Glu Lys Asp His Val Tyr Leu Gln Leu<br>305                      310                  315                320 | | 960 |
| cac cac cta cct cca gag cag ctg gcc acg cgc ctg cct ggc att tca<br>His His Leu Pro Pro Glu Gln Leu Ala Thr Arg Leu Pro Gly Ile Ser<br>                       325                  330                335 | | 1008 |
| gag aca gcc atg atc ttc gct ggc gtg gac gtc acg aag gag ccg atc<br>Glu Thr Ala Met Ile Phe Ala Gly Val Asp Val Thr Lys Glu Pro Ile<br>                    340                  345                350 | | 1056 |
| cct gtc ctc ccc acc gtg cat tat aac atg ggc ggc att ccc acc aac<br>Pro Val Leu Pro Thr Val His Tyr Asn Met Gly Gly Ile Pro Thr Asn<br>                355                  360                365 | | 1104 |

```
tac aag ggg cag gtc ctg agg cac gtg aat ggc cag gat cag att gtg      1152
Tyr Lys Gly Gln Val Leu Arg His Val Asn Gly Gln Asp Gln Ile Val
    370                 375                 380 ccc ggc ctg tac gcc tgt ggg gag gcc gcc tgt gcc tcg gta cat ggt      1200
Pro Gly Leu Tyr Ala Cys Gly Glu Ala Ala Cys Ala Ser Val His Gly
385                 390                 395                 400 gcc aac cgc ctc ggg gca aac tcg ctc ttg gac ctg gtt gtc ttt ggt      1248
Ala Asn Arg Leu Gly Ala Asn Ser Leu Leu Asp Leu Val Val Phe Gly
                405                 410                 415 cgg gca tgt gcc ctg agc atc gaa gag tca tgc agg cct gga gat aaa      1296
Arg Ala Cys Ala Leu Ser Ile Glu Glu Ser Cys Arg Pro Gly Asp Lys
420                 425                 430 gtc cct cca att aaa cca aac gct ggg gaa gaa tct gtc atg aat ctt      1344
Val Pro Pro Ile Lys Pro Asn Ala Gly Glu Glu Ser Val Met Asn Leu
    435                 440                 445 gac aaa ttg aga ttt gct gat gga agc ata aga aca tcg gaa ctg cga      1392
Asp Lys Leu Arg Phe Ala Asp Gly Ser Ile Arg Thr Ser Glu Leu Arg
450                 455                 460 ctc agc atg cag aag tca atg caa aat cat gct gcc gtg ttc cgt gtg      1440
Leu Ser Met Gln Lys Ser Met Gln Asn His Ala Ala Val Phe Arg Val
465                 470                 475                 480 gga agc gtg ttg caa gaa ggt tgt ggg aaa atc agc aag ctc tat gga      1488
Gly Ser Val Leu Gln Glu Gly Cys Gly Lys Ile Ser Lys Leu Tyr Gly
                485                 490                 495 gac cta aag cac ctg aag acg ttc gac cgg gga atg gtc tgg aac acg      1536
Asp Leu Lys His Leu Lys Thr Phe Asp Arg Gly Met Val Trp Asn Thr
                500                 505                 510 gac ctg gtg gag acc ctg gag ctg cag aac ctg atg ctg tgt gcg ctg      1584
Asp Leu Val Glu Thr Leu Glu Leu Gln Asn Leu Met Leu Cys Ala Leu
            515                 520                 525 cag acc atc tac gga gca gag gca cgg aag gag tca cgg ggc gcg cat      1632
Gln Thr Ile Tyr Gly Ala Glu Ala Arg Lys Glu Ser Arg Gly Ala His
    530                 535                 540 gcc agg gaa gac tac aag gtg cgg att gat gag tac gat tac tcc aag      1680
Ala Arg Glu Asp Tyr Lys Val Arg Ile Asp Glu Tyr Asp Tyr Ser Lys
545                 550                 555                 560 ccc atc cag ggg caa cag aag aag ccc ttt gag gag cac tgg agg aag      1728
Pro Ile Gln Gly Gln Gln Lys Lys Pro Phe Glu Glu His Trp Arg Lys
                565                 570                 575 cac acc ctg tcc tat gtg gac gtt ggc act ggg aag gtc act ctg gaa      1776
His Thr Leu Ser Tyr Val Asp Val Gly Thr Gly Lys Val Thr Leu Glu
                580                 585                 590 tat aga ccc gtg atc gac aaa act ttg aac gag gct gac tgt gcc acc      1824
Tyr Arg Pro Val Ile Asp Lys Thr Leu Asn Glu Ala Asp Cys Ala Thr
            595                 600                 605 gtc ccg cca gcc att cgc tcc tac tga                                   1851
Val Pro Pro Ala Ile Arg Ser Tyr
    610                 615

<210> SEQ ID NO 2
<211> LENGTH: 616
<212> TYPE: PRT
<213> ORGANISM: Homo sapiens

<400> SEQUENCE: 2

Met Ser Gly Val Arg Gly Leu Ser Arg Leu Leu Ser Ala Arg Arg Leu
1               5                   10                  15

Ala Leu Ala Lys Ala Trp Pro Thr Val Leu Gln Thr Gly Thr Arg Gly
            20                  25                  30
```

```
Phe His Phe Thr Val Asp Gly Asn Lys Arg Ala Ser Ala Lys Val Ser
         35                  40                  45

Asp Ser Ile Ser Ala Gln Tyr Pro Val Val Asp His Glu Phe Asp Ala
 50                  55                  60

Val Val Gly Ala Gly Ala Gly Leu Arg Ala Ala Phe Gly Leu
 65              70                  75                  80

Ser Glu Ala Gly Phe Asn Thr Ala Cys Val Thr Lys Leu Phe Pro Thr
                 85                  90                  95

Arg Ser His Thr Val Ala Ala Gln Leu Glu Asn Tyr Gly Met Pro Phe
             100                 105                 110

Ser Arg Thr Glu Asp Gly Lys Ile Tyr Gln Arg Ala Phe Gly Gly Gln
         115                 120                 125

Ser Leu Lys Phe Gly Lys Gly Gly Gln Ala His Arg Cys Cys Cys Val
     130                 135                 140

Ala Asp Arg Thr Gly His Ser Leu Leu His Thr Leu Tyr Gly Arg Ser
 145                 150                 155                 160

Leu Arg Tyr Asp Thr Ser Tyr Phe Val Glu Tyr Phe Ala Leu Asp Leu
                 165                 170                 175

Leu Met Glu Asn Gly Glu Cys Arg Gly Val Ile Ala Leu Cys Ile Glu
             180                 185                 190

Asp Gly Ser Ile His Arg Ile Arg Ala Lys Asn Thr Val Val Ala Thr
         195                 200                 205

Gly Gly Tyr Gly Arg Thr Tyr Phe Ser Cys Thr Ser Ala His Thr Ser
     210                 215                 220

Thr Gly Asp Gly Thr Ala Met Ile Thr Arg Ala Gly Leu Pro Cys Gln
225                 230                 235                 240

Asp Leu Glu Phe Val Gln Phe His Pro Thr Gly Ile Tyr Gly Ala Gly
                 245                 250                 255

Cys Leu Ile Thr Glu Gly Cys Arg Gly Glu Gly Gly Ile Leu Ile Asn
             260                 265                 270

Ser Gln Gly Glu Arg Phe Met Glu Arg Tyr Ala Pro Val Ala Lys Asp
         275                 280                 285

Leu Ala Ser Arg Asp Val Val Ser Arg Ser Met Thr Leu Glu Ile Arg
 290                 295                 300

Glu Gly Arg Gly Cys Gly Pro Glu Lys Asp His Val Tyr Leu Gln Leu
305                 310                 315                 320

His His Leu Pro Pro Glu Gln Leu Ala Thr Arg Leu Pro Gly Ile Ser
                 325                 330                 335

Glu Thr Ala Met Ile Phe Ala Gly Val Asp Val Thr Lys Glu Pro Ile
             340                 345                 350

Pro Val Leu Pro Thr Val His Tyr Asn Met Gly Gly Ile Pro Thr Asn
         355                 360                 365

Tyr Lys Gly Gln Val Leu Arg His Val Asn Gly Gln Asp Gln Ile Val
 370                 375                 380

Pro Gly Leu Tyr Ala Cys Gly Glu Ala Ala Cys Ala Ser Val His Gly
385                 390                 395                 400

Ala Asn Arg Leu Gly Ala Asn Ser Leu Leu Asp Leu Val Val Phe Gly
                 405                 410                 415

Arg Ala Cys Ala Leu Ser Ile Glu Glu Ser Cys Arg Pro Gly Asp Lys
             420                 425                 430

Val Pro Pro Ile Lys Pro Asn Ala Gly Glu Glu Ser Val Met Asn Leu
         435                 440                 445

Asp Lys Leu Arg Phe Ala Asp Gly Ser Ile Arg Thr Ser Glu Leu Arg
```

```
                    450              455              460
Leu Ser Met Gln Lys Ser Met Gln Asn His Ala Ala Val Phe Arg Val
465                 470              475              480

Gly Ser Val Leu Gln Glu Gly Cys Gly Lys Ile Ser Lys Leu Tyr Gly
                485              490              495

Asp Leu Lys His Leu Lys Thr Phe Asp Arg Gly Met Val Trp Asn Thr
            500              505              510

Asp Leu Val Glu Thr Leu Glu Leu Gln Asn Leu Met Leu Cys Ala Leu
        515              520              525

Gln Thr Ile Tyr Gly Ala Glu Ala Arg Lys Glu Ser Arg Gly Ala His
    530              535              540

Ala Arg Glu Asp Tyr Lys Val Arg Ile Asp Glu Tyr Asp Tyr Ser Lys
545             550              555              560

Pro Ile Gln Gly Gln Lys Lys Pro Phe Glu His Trp Arg Lys
                565              570              575

His Thr Leu Ser Tyr Val Asp Val Gly Thr Gly Lys Val Thr Leu Glu
            580              585              590

Tyr Arg Pro Val Ile Asp Lys Thr Leu Asn Glu Ala Asp Cys Ala Thr
            595              600              605

Val Pro Pro Ala Ile Arg Ser Tyr
        610              615

<210> SEQ ID NO 3
<211> LENGTH: 1173
<212> TYPE: DNA
<213> ORGANISM: Homo sapiens
<220> FEATURE:
<221> NAME/KEY: CDS
<222> LOCATION: (1)..(1173)

<400> SEQUENCE: 3 atg ctg gca gcc cgg aca ggg gca gcg ggg agt cag atc tca gag gag        48
Met Leu Ala Ala Arg Thr Gly Ala Ala Gly Ser Gln Ile Ser Glu Glu
1               5                   10                  15 aac acc aag tta agg aga cag tct ggg ttt tct gta gca ggg aaa gac        96
Asn Thr Lys Leu Arg Arg Gln Ser Gly Phe Ser Val Ala Gly Lys Asp
                20                  25                  30 aaa tct ccc aag aaa gcc tca gaa aac gct aaa gac agc agc ctt agt        144
Lys Ser Pro Lys Lys Ala Ser Glu Asn Ala Lys Asp Ser Ser Leu Ser
            35                  40                  45 ccc tca ggg gaa agc cag ctc agg gcg cgt caa ctg gct ctg ctg cgc        192
Pro Ser Gly Glu Ser Gln Leu Arg Ala Arg Gln Leu Ala Leu Leu Arg
        50                  55                  60 gaa gtg gag atg aac tgg tac cta aag ctc tgc gac ctg tcc agc gag        240
Glu Val Glu Met Asn Trp Tyr Leu Lys Leu Cys Asp Leu Ser Ser Glu
65                  70                  75                  80 cac acc acc gtc tgc acc aca ggc atg ccg cac agg aat ctt gga aaa        288
His Thr Thr Val Cys Thr Thr Gly Met Pro His Arg Asn Leu Gly Lys
                85                  90                  95 tca gga ctc aga gtt tct tgc ttg ggt ctt gga aca tgg gtg aca ttt        336
Ser Gly Leu Arg Val Ser Cys Leu Gly Leu Gly Thr Trp Val Thr Phe
            100                 105                 110 gga ggt caa att tca gat gag gtt gct gaa cgg ctg atg acc atc gcc        384
Gly Gly Gln Ile Ser Asp Glu Val Ala Glu Arg Leu Met Thr Ile Ala
        115                 120                 125 tat gaa agt ggt gtt aac ctc ttt gat act gcc gaa gtc tat gct gct        432
Tyr Glu Ser Gly Val Asn Leu Phe Asp Thr Ala Glu Val Tyr Ala Ala
    130                 135                 140
```

| | | | | | | | | | | | | | | | | |
|---|---|---|---|---|---|---|---|---|---|---|---|---|---|---|---|---|
| gga | aag | gct | gaa | gtg | att | ctg | ggg | agc | atc | atc | aag | aag | aaa | ggc | tgg | 480 |
| Gly | Lys | Ala | Glu | Val | Ile | Leu | Gly | Ser | Ile | Ile | Lys | Lys | Lys | Gly | Trp | |
| 145 | | | | 150 | | | | | 155 | | | | | 160 | | |
| agg | agg | tcc | agt | ctg | gtc | ata | aca | acc | aaa | ctc | tac | tgg | ggt | gga | aaa | 528 |
| Arg | Arg | Ser | Ser | Leu | Val | Ile | Thr | Thr | Lys | Leu | Tyr | Trp | Gly | Gly | Lys | |
| | | | | 165 | | | | | 170 | | | | | 175 | | |
| gct | gaa | aca | gaa | aga | ggg | ctg | tca | aga | aag | cat | att | att | gaa | gaa | att | 576 |
| Ala | Glu | Thr | Glu | Arg | Gly | Leu | Ser | Arg | Lys | His | Ile | Ile | Glu | Glu | Ile | |
| | | 180 | | | | | 185 | | | | | 190 | | | | |
| gtc | cga | gcc | atg | aca | cat | gtg | ata | aac | caa | ggc | atg | gcg | atg | tac | tgg | 624 |
| Val | Arg | Ala | Met | Thr | His | Val | Ile | Asn | Gln | Gly | Met | Ala | Met | Tyr | Trp | |
| | | 195 | | | | | 200 | | | | | 205 | | | | |
| ggc | acc | tcg | aga | tgg | agt | gct | atg | gag | atc | atg | gaa | gcc | tat | tct | gta | 672 |
| Gly | Thr | Ser | Arg | Trp | Ser | Ala | Met | Glu | Ile | Met | Glu | Ala | Tyr | Ser | Val | |
| | | 210 | | | | | 215 | | | | | 220 | | | | |
| gca | aga | cag | ttc | aat | atg | atc | ccg | ccg | gtc | tgt | gaa | caa | gct | gag | tac | 720 |
| Ala | Arg | Gln | Phe | Asn | Met | Ile | Pro | Pro | Val | Cys | Glu | Gln | Ala | Glu | Tyr | |
| 225 | | | | 230 | | | | | 235 | | | | | 240 | | |
| cat | ctt | ttc | cag | aga | gag | aaa | gtg | gag | gtc | cag | ctg | cca | gag | ctc | tac | 768 |
| His | Leu | Phe | Gln | Arg | Glu | Lys | Val | Glu | Val | Gln | Leu | Pro | Glu | Leu | Tyr | |
| | | | | 245 | | | | | 250 | | | | | 255 | | |
| cac | aaa | ata | ggt | gtt | ggc | gca | atg | aca | tgg | tct | cca | ctt | gcc | tgt | gga | 816 |
| His | Lys | Ile | Gly | Val | Gly | Ala | Met | Thr | Trp | Ser | Pro | Leu | Ala | Cys | Gly | |
| | | | | 260 | | | | | 265 | | | | | 270 | | |
| atc | atc | tca | gga | aaa | tac | gga | aac | ggg | gtg | cct | gaa | agt | tcc | agg | gct | 864 |
| Ile | Ile | Ser | Gly | Lys | Tyr | Gly | Asn | Gly | Val | Pro | Glu | Ser | Ser | Arg | Ala | |
| | | | | 275 | | | | | 280 | | | | | 285 | | |
| tca | ctg | aag | tgc | tac | cag | tgg | ttg | aaa | gaa | aga | att | gta | agt | gaa | gaa | 912 |
| Ser | Leu | Lys | Cys | Tyr | Gln | Trp | Leu | Lys | Glu | Arg | Ile | Val | Ser | Glu | Glu | |
| | | 290 | | | | | 295 | | | | | 300 | | | | |
| ggg | aga | aaa | cag | caa | aac | aag | cta | aaa | gac | ctt | tcc | cca | att | gcg | gag | 960 |
| Gly | Arg | Lys | Gln | Gln | Asn | Lys | Leu | Lys | Asp | Leu | Ser | Pro | Ile | Ala | Glu | |
| 305 | | | | 310 | | | | | 315 | | | | | 320 | | |
| cgt | ctg | gga | tgc | aca | cta | cct | cag | cta | gct | gtt | gcg | tgg | tgc | ctg | aga | 1008 |
| Arg | Leu | Gly | Cys | Thr | Leu | Pro | Gln | Leu | Ala | Val | Ala | Trp | Cys | Leu | Arg | |
| | | | | 325 | | | | | 330 | | | | | 335 | | |
| aat | gaa | ggt | gtg | agt | tct | gtg | ctc | ctg | gga | tca | tcc | act | cct | gaa | caa | 1056 |
| Asn | Glu | Gly | Val | Ser | Ser | Val | Leu | Leu | Gly | Ser | Ser | Thr | Pro | Glu | Gln | |
| | | | | 340 | | | | | 345 | | | | | 350 | | |
| ctc | att | gaa | aac | ctt | ggt | gcc | att | cag | gtt | ctc | cca | aag | atg | aca | tca | 1104 |
| Leu | Ile | Glu | Asn | Leu | Gly | Ala | Ile | Gln | Val | Leu | Pro | Lys | Met | Thr | Ser | |
| | | | | 355 | | | | | 360 | | | | | 365 | | |
| cat | gtg | gta | aat | gag | att | gat | aac | ata | ctg | cgc | aac | aag | ccc | tac | agc | 1152 |
| His | Val | Val | Asn | Glu | Ile | Asp | Asn | Ile | Leu | Arg | Asn | Lys | Pro | Tyr | Ser | |
| 370 | | | | 375 | | | | | 380 | | | | | | | |
| aag | aag | gac | tat | aga | tca | taa | | | | | | | | | | 1173 |
| Lys | Lys | Asp | Tyr | Arg | Ser | | | | | | | | | | | |
| 385 | | | | 390 | | | | | | | | | | | | |

<210> SEQ ID NO 4
<211> LENGTH: 390
<212> TYPE: PRT
<213> ORGANISM: Homo sapiens

<400> SEQUENCE: 4

Met Leu Ala Ala Arg Thr Gly Ala Ala Gly Ser Gln Ile Ser Glu Glu
1               5                   10                  15

Asn Thr Lys Leu Arg Arg Gln Ser Gly Phe Ser Val Ala Gly Lys Asp
            20                  25                  30

Lys Ser Pro Lys Lys Ala Ser Glu Asn Ala Lys Asp Ser Ser Leu Ser

```
                35                  40                  45
Pro Ser Gly Glu Ser Gln Leu Arg Ala Arg Gln Leu Ala Leu Leu Arg
 50                  55                  60
Glu Val Glu Met Asn Trp Tyr Leu Lys Leu Cys Asp Leu Ser Ser Glu
 65                  70                  75                  80
His Thr Thr Val Cys Thr Thr Gly Met Pro His Arg Asn Leu Gly Lys
                 85                  90                  95
Ser Gly Leu Arg Val Ser Cys Leu Gly Leu Gly Thr Trp Val Thr Phe
                100                 105                 110
Gly Gly Gln Ile Ser Asp Glu Val Ala Glu Arg Leu Met Thr Ile Ala
                115                 120                 125
Tyr Glu Ser Gly Val Asn Leu Phe Asp Thr Ala Glu Val Tyr Ala Ala
            130                 135                 140
Gly Lys Ala Glu Val Ile Leu Gly Ser Ile Ile Lys Lys Lys Gly Trp
145                 150                 155                 160
Arg Arg Ser Ser Leu Val Ile Thr Thr Lys Leu Tyr Trp Gly Gly Lys
                165                 170                 175
Ala Glu Thr Glu Arg Gly Leu Ser Arg Lys His Ile Ile Glu Glu Ile
            180                 185                 190
Val Arg Ala Met Thr His Val Ile Asn Gln Gly Met Ala Met Tyr Trp
        195                 200                 205
Gly Thr Ser Arg Trp Ser Ala Met Glu Ile Met Glu Ala Tyr Ser Val
210                 215                 220
Ala Arg Gln Phe Asn Met Ile Pro Pro Val Cys Glu Gln Ala Glu Tyr
225                 230                 235                 240
His Leu Phe Gln Arg Glu Lys Val Glu Val Gln Leu Pro Glu Leu Tyr
                245                 250                 255
His Lys Ile Gly Val Gly Ala Met Thr Trp Ser Pro Leu Ala Cys Gly
            260                 265                 270
Ile Ile Ser Gly Lys Tyr Gly Asn Gly Val Pro Glu Ser Ser Arg Ala
            275                 280                 285
Ser Leu Lys Cys Tyr Gln Trp Leu Lys Glu Arg Ile Val Ser Glu Glu
290                 295                 300
Gly Arg Lys Gln Gln Asn Lys Leu Lys Asp Leu Ser Pro Ile Ala Glu
305                 310                 315                 320
Arg Leu Gly Cys Thr Leu Pro Gln Leu Ala Val Ala Trp Cys Leu Arg
                325                 330                 335
Asn Glu Gly Val Ser Ser Val Leu Leu Gly Ser Ser Thr Pro Glu Gln
            340                 345                 350
Leu Ile Glu Asn Leu Gly Ala Ile Gln Val Leu Pro Lys Met Thr Ser
            355                 360                 365
His Val Val Asn Glu Ile Asp Asn Ile Leu Arg Asn Lys Pro Tyr Ser
        370                 375                 380
Lys Lys Asp Tyr Arg Ser
385                 390

<210> SEQ ID NO 5
<211> LENGTH: 885
<212> TYPE: DNA
<213> ORGANISM: Homo sapiens
<220> FEATURE:
<221> NAME/KEY: CDS
<222> LOCATION: (1)..(885)

<400> SEQUENCE: 5
```

```
atg aat tct gaa ctt gac tat tat gaa aag ttt gaa gaa gtc cat ggg      48
Met Asn Ser Glu Leu Asp Tyr Tyr Glu Lys Phe Glu Glu Val His Gly
1               5                   10                  15 att cta atg tat aaa gat ttt gtc aaa tat tgg gat aat gtg gaa gcg      96
Ile Leu Met Tyr Lys Asp Phe Val Lys Tyr Trp Asp Asn Val Glu Ala
            20                  25                  30 ttc cag gca aga cca gat gat ctt gtc att gcc acc tac cct aaa tct     144
Phe Gln Ala Arg Pro Asp Asp Leu Val Ile Ala Thr Tyr Pro Lys Ser
        35                  40                  45 ggt aca acc tgg gtt agt gaa att gtg tat atg atc tat aaa gag ggt     192
Gly Thr Thr Trp Val Ser Glu Ile Val Tyr Met Ile Tyr Lys Glu Gly
    50                  55                  60 gat gtg gaa aag tgc aaa gaa gat gta att ttt aat cga ata cct ttc     240
Asp Val Glu Lys Cys Lys Glu Asp Val Ile Phe Asn Arg Ile Pro Phe
65                  70                  75                  80 ctg gaa tgc aga aaa gaa aac ctc atg aat gga gta aaa caa tta gat     288
Leu Glu Cys Arg Lys Glu Asn Leu Met Asn Gly Val Lys Gln Leu Asp
                85                  90                  95 gag atg aat tct cct aga att gtg aag act cat ttg cca cct gaa ctt     336
Glu Met Asn Ser Pro Arg Ile Val Lys Thr His Leu Pro Pro Glu Leu
            100                 105                 110 ctt cct gcc tca ttt tgg gaa aag gat tgt aag ata atc tat ctt tgc     384
Leu Pro Ala Ser Phe Trp Glu Lys Asp Cys Lys Ile Ile Tyr Leu Cys
        115                 120                 125 cgg aat gca aag gat gtg gct gtt tcc ttt tat tat ttc ttt cta atg     432
Arg Asn Ala Lys Asp Val Ala Val Ser Phe Tyr Tyr Phe Phe Leu Met
    130                 135                 140 gtg gct ggt cat cca aat cct gga tcc ttt cca gag ttt gtg gag aaa     480
Val Ala Gly His Pro Asn Pro Gly Ser Phe Pro Glu Phe Val Glu Lys
145                 150                 155                 160 ttc atg caa gga cag gtt cct tat ggt tcc tgg tat aaa cat gta aaa     528
Phe Met Gln Gly Gln Val Pro Tyr Gly Ser Trp Tyr Lys His Val Lys
                165                 170                 175 tct tgg tgg gaa aag gga aag agt cca cgt gta cta ttt ctt ttc tac     576
Ser Trp Trp Glu Lys Gly Lys Ser Pro Arg Val Leu Phe Leu Phe Tyr
            180                 185                 190 gaa gac ctg aaa gag gat atc aga aaa gag gtg ata aaa ttg ata cat     624
Glu Asp Leu Lys Glu Asp Ile Arg Lys Glu Val Ile Lys Leu Ile His
        195                 200                 205 ttc ctg gaa agg aag cca tca gag gag ctt gtg gac agg att ata cat     672
Phe Leu Glu Arg Lys Pro Ser Glu Glu Leu Val Asp Arg Ile Ile His
    210                 215                 220 cat act tcg ttc caa gag atg aag aac aat cca tcc aca aat tac aca     720
His Thr Ser Phe Gln Glu Met Lys Asn Asn Pro Ser Thr Asn Tyr Thr
225                 230                 235                 240 aca ctg cca gac gaa att atg aac cag aaa ttg tcg ccc ttc atg aga     768
Thr Leu Pro Asp Glu Ile Met Asn Gln Lys Leu Ser Pro Phe Met Arg
                245                 250                 255 aag gga att aca gga gac tgg aaa aat cac ttt aca gta gcc ctg aat     816
Lys Gly Ile Thr Gly Asp Trp Lys Asn His Phe Thr Val Ala Leu Asn
            260                 265                 270 gaa aaa ttt gat aaa cat tat gag cag caa atg aag gaa tct aca ctg     864
Glu Lys Phe Asp Lys His Tyr Glu Gln Gln Met Lys Glu Ser Thr Leu
        275                 280                 285 aag ttt cga act gag atc taa                                         885
Lys Phe Arg Thr Glu Ile
    290

<210> SEQ ID NO 6
<211> LENGTH: 294
```

```
<212> TYPE: PRT
<213> ORGANISM: Homo sapiens

<400> SEQUENCE: 6

Met Asn Ser Glu Leu Asp Tyr Tyr Glu Lys Phe Glu Val His Gly
1               5                   10                  15

Ile Leu Met Tyr Lys Asp Phe Val Lys Tyr Trp Asp Asn Val Glu Ala
            20                  25                  30

Phe Gln Ala Arg Pro Asp Asp Leu Val Ile Ala Thr Tyr Pro Lys Ser
            35                  40                  45

Gly Thr Thr Trp Val Ser Glu Ile Val Tyr Met Ile Tyr Lys Glu Gly
50                      55                  60

Asp Val Glu Lys Cys Lys Glu Asp Val Ile Phe Asn Arg Ile Pro Phe
65                  70                  75                  80

Leu Glu Cys Arg Lys Glu Asn Leu Met Asn Gly Val Lys Gln Leu Asp
                85                  90                  95

Glu Met Asn Ser Pro Arg Ile Val Lys Thr His Leu Pro Pro Glu Leu
            100                 105                 110

Leu Pro Ala Ser Phe Trp Glu Lys Asp Cys Lys Ile Ile Tyr Leu Cys
        115                 120                 125

Arg Asn Ala Lys Asp Val Ala Val Ser Phe Tyr Tyr Phe Phe Leu Met
130                 135                 140

Val Ala Gly His Pro Asn Pro Gly Ser Phe Pro Glu Phe Val Glu Lys
145                 150                 155                 160

Phe Met Gln Gly Gln Val Pro Tyr Gly Ser Trp Tyr Lys His Val Lys
                165                 170                 175

Ser Trp Trp Glu Lys Gly Lys Ser Pro Arg Val Leu Phe Leu Phe Tyr
            180                 185                 190

Glu Asp Leu Lys Glu Asp Ile Arg Lys Glu Val Ile Lys Leu Ile His
        195                 200                 205

Phe Leu Glu Arg Lys Pro Ser Glu Glu Leu Val Asp Arg Ile Ile His
    210                 215                 220

His Thr Ser Phe Gln Glu Met Lys Asn Asn Pro Ser Thr Asn Tyr Thr
225                 230                 235                 240

Thr Leu Pro Asp Glu Ile Met Asn Gln Lys Leu Ser Pro Phe Met Arg
                245                 250                 255

Lys Gly Ile Thr Gly Asp Trp Lys Asn His Phe Thr Val Ala Leu Asn
            260                 265                 270

Glu Lys Phe Asp Lys His Tyr Glu Gln Gln Met Lys Glu Ser Thr Leu
        275                 280                 285

Lys Phe Arg Thr Glu Ile
    290

<210> SEQ ID NO 7
<211> LENGTH: 3963
<212> TYPE: DNA
<213> ORGANISM: Homo sapiens
<220> FEATURE:
<221> NAME/KEY: CDS
<222> LOCATION: (1)..(3963)

<400> SEQUENCE: 7 atg ttt ggg ctg gac caa ttc gag ccc cag gtc aac agc agg aac gct      48
Met Phe Gly Leu Asp Gln Phe Glu Pro Gln Val Asn Ser Arg Asn Ala
1               5                   10                  15 ggc cag ggc gag agg aac ttt aac gag acc gga ctg agc atg aac acc      96
Gly Gln Gly Glu Arg Asn Phe Asn Glu Thr Gly Leu Ser Met Asn Thr
```

```
                      20                      25                      30
cac ttt aag gcc ccg gct ttc cac act ggg ggg ccc cct ggc cct gtg           144
His Phe Lys Ala Pro Ala Phe His Thr Gly Gly Pro Pro Gly Pro Val
         35                      40                      45 gat cct gct atg agc gcg ctg ggc gaa ccc ccg atc ttg ggc atg aac           192
Asp Pro Ala Met Ser Ala Leu Gly Glu Pro Pro Ile Leu Gly Met Asn
 50                      55                      60 atg gag ccc tac ggc ttc cac gcg cgc ggc cac tcg gag ttg cac gca           240
Met Glu Pro Tyr Gly Phe His Ala Arg Gly His Ser Glu Leu His Ala
 65                      70                      75                  80 ggg ggg ctg caa gcg cag cct gtg cac ggc ttc ttt ggc ggc cag cag           288
Gly Gly Leu Gln Ala Gln Pro Val His Gly Phe Phe Gly Gly Gln Gln
                     85                      90                      95 cct cac cac ggc cac ccg gga agt cat cat ccc cac cag cat cac ccc           336
Pro His His Gly His Pro Gly Ser His His Pro His Gln His His Pro
            100                     105                     110 cac ttt ggg ggc aac ttc ggt ggc ccg gac ccc ggg gcc tcg tgc ctg           384
His Phe Gly Gly Asn Phe Gly Gly Pro Asp Pro Gly Ala Ser Cys Leu
                115                     120                     125 cac ggg ggt cgc ctg ctc ggc tac ggc ggc gca gcc gga ggc ctg ggc           432
His Gly Gly Arg Leu Leu Gly Tyr Gly Gly Ala Ala Gly Gly Leu Gly
130                     135                     140 agc cag ccg ccc ttc gcc gag ggc tat gag cac atg gcg gag agc cag           480
Ser Gln Pro Pro Phe Ala Glu Gly Tyr Glu His Met Ala Glu Ser Gln
145                     150                     155                 160 ggg cct gag agc ttc ggc ccg cag cga ccg ggg aac ctc ccg gac ttc           528
Gly Pro Glu Ser Phe Gly Pro Gln Arg Pro Gly Asn Leu Pro Asp Phe
                165                     170                     175 cac agt tca ggt gcc tcc agc cac gcc gtg ccg gcc cca tgc ctg ccg           576
His Ser Ser Gly Ala Ser Ser His Ala Val Pro Ala Pro Cys Leu Pro
                180                     185                     190 ctg gac cag agc cct aac cga gcc gcc tcc ttc cac ggc ctg ccg tcc           624
Leu Asp Gln Ser Pro Asn Arg Ala Ala Ser Phe His Gly Leu Pro Ser
                195                     200                     205 tcc agc ggc tcc gat tcc cac agt ctg gag cca cgg agg gtg acg aac           672
Ser Ser Gly Ser Asp Ser His Ser Leu Glu Pro Arg Arg Val Thr Asn
    210                     215                     220 caa gga gcc gtc gac tcg ctg gaa tac aat tac ccg ggc gag gcg ccc           720
Gln Gly Ala Val Asp Ser Leu Glu Tyr Asn Tyr Pro Gly Glu Ala Pro
225                     230                     235                 240 tcg gga cat ttt gac atg ttt tcg ccc tct gac tcc gaa ggg cag ctg           768
Ser Gly His Phe Asp Met Phe Ser Pro Ser Asp Ser Glu Gly Gln Leu
                245                     250                     255 cct cat tat gca gcg ggt cgc cag gtt cct ggg ggc gct ttc ccg ggc           816
Pro His Tyr Ala Ala Gly Arg Gln Val Pro Gly Gly Ala Phe Pro Gly
                260                     265                     270 gcc tcg gcc atg ccc aga gct gcg ggc atg gtg ggc ttg tcc aaa atg           864
Ala Ser Ala Met Pro Arg Ala Ala Gly Met Val Gly Leu Ser Lys Met
            275                     280                     285 cac gcc cag cca ccg cag cag cag ccc cag cag cag cag ccc cag               912
His Ala Gln Pro Pro Gln Gln Pro Gln Gln Gln Gln Pro Gln
            290                     295                     300 cag cag cag cag cag cat ggt gtg ttc ttt gag agg ttc agt ggg gcc           960
Gln Gln Gln Gln Gln His Gly Val Phe Phe Glu Arg Phe Ser Gly Ala
305                     310                     315                 320 aga aag atg cct gtg ggt ctg gag ccc tca gtg ggc tcc agg cac ccg          1008
Arg Lys Met Pro Val Gly Leu Glu Pro Ser Val Gly Ser Arg His Pro
                325                     330                     335 tta atg cag cct ccc cag cag gcc ccg cca ccc cct cag cag cag ccc          1056
```

-continued

| | | |
|---|---|---|
| Leu Met Gln Pro Pro Gln Gln Ala Pro Pro Pro Gln Gln Pro<br>340                 345                 350 | | |
| ccg cag cag ccg cca cag cag cag ccg ccg ccg cca ccc ggg ctt cta<br>Pro Gln Gln Pro Pro Gln Gln Gln Pro Pro Pro Pro Gly Leu Leu<br>        355                 360                 365 | 1104 | |
| gtc cga caa aat tcg tgc ccg cct gcg ctc cct cgg ccc cag cag ggc<br>Val Arg Gln Asn Ser Cys Pro Pro Ala Leu Pro Arg Pro Gln Gln Gly<br>370                 375                 380 | 1152 | |
| gag gcg ggc acg ccc agc ggc ggc ctg cag gac gga ggc ccc atg ctg<br>Glu Ala Gly Thr Pro Ser Gly Gly Leu Gln Asp Gly Gly Pro Met Leu<br>385                 390                 395                 400 | 1200 | |
| ccc agc cag cac gcg caa ttc gag tat ccc atc cac cgg ctg gag aac<br>Pro Ser Gln His Ala Gln Phe Glu Tyr Pro Ile His Arg Leu Glu Asn<br>                405                 410                 415 | 1248 | |
| cgg agc atg cac cct tat tcc gag cct gtt ttc agc atg cag cat cct<br>Arg Ser Met His Pro Tyr Ser Glu Pro Val Phe Ser Met Gln His Pro<br>                420                 425                 430 | 1296 | |
| cct ccg cag cag gcg ccc aac cag cgg ctg cag cat ttc gac gcg ccc<br>Pro Pro Gln Gln Ala Pro Asn Gln Arg Leu Gln His Phe Asp Ala Pro<br>                435                 440                 445 | 1344 | |
| ccc tac atg aac gtg gcc aag agg ccg cgc ttc gac ttt ccg ggc agc<br>Pro Tyr Met Asn Val Ala Lys Arg Pro Arg Phe Asp Phe Pro Gly Ser<br>450                 455                 460 | 1392 | |
| gcg gga gtg gac cgc tgc gct tcg tgg aac ggc agc atg cac aac ggc<br>Ala Gly Val Asp Arg Cys Ala Ser Trp Asn Gly Ser Met His Asn Gly<br>465                 470                 475                 480 | 1440 | |
| gct ctg gat aat cac ctc tcc cct tcc gcc tac cca ggc cta ccc ggc<br>Ala Leu Asp Asn His Leu Ser Pro Ser Ala Tyr Pro Gly Leu Pro Gly<br>                485                 490                 495 | 1488 | |
| gag ttc aca ccg cct gtg ccc gac agc ttc cct tcg ggg ccg ccc ctg<br>Glu Phe Thr Pro Pro Val Pro Asp Ser Phe Pro Ser Gly Pro Pro Leu<br>                500                 505                 510 | 1536 | |
| cag cat ccg gcc ccg gac cac cag tcc ctg caa cag cag cag cag cag<br>Gln His Pro Ala Pro Asp His Gln Ser Leu Gln Gln Gln Gln Gln Gln<br>                515                 520                 525 | 1584 | |
| cag cag cag cag cag caa cag cag cag cag cag caa cag caa cag caa<br>Gln Gln Gln Gln Gln Gln Gln Gln Gln Gln Gln Gln Gln Gln Gln Gln<br>530                 535                 540 | 1632 | |
| cag cag cag cag cag cag cgc caa aac gcg gcc ctc atg att aag cag<br>Gln Gln Gln Gln Gln Gln Arg Gln Asn Ala Ala Leu Met Ile Lys Gln<br>545                 550                 555                 560 | 1680 | |
| atg gcg tcg cgg aat cag cag cag cgg ctg cgc cag ccc aac ctg gct<br>Met Ala Ser Arg Asn Gln Gln Gln Arg Leu Arg Gln Pro Asn Leu Ala<br>                565                 570                 575 | 1728 | |
| cag cta ggc cac ccc ggg gac gtg ggc cag ggc ggc ctg gtg cat ggc<br>Gln Leu Gly His Pro Gly Asp Val Gly Gln Gly Gly Leu Val His Gly<br>                580                 585                 590 | 1776 | |
| ggc ccg gtg ggc ggc ttg gcc cag ccg aac ttt gag cgc gaa ggc ggc<br>Gly Pro Val Gly Gly Leu Ala Gln Pro Asn Phe Glu Arg Glu Gly Gly<br>                595                 600                 605 | 1824 | |
| agc acg ggc gcc ggg cgt ctg ggc acc ttc gag cag cag gcg ccg cac<br>Ser Thr Gly Ala Gly Arg Leu Gly Thr Phe Glu Gln Gln Ala Pro His<br>610                 615                 620 | 1872 | |
| ttg gcg caa gag agc gcg tgg ttc tca ggt ccg cat ccg ccg ccc gga<br>Leu Ala Gln Glu Ser Ala Trp Phe Ser Gly Pro His Pro Pro Pro Gly<br>625                 630                 635                 640 | 1920 | |
| gac ctg ctg ccc cgt agg atg ggc ggc tcg ggt ctg ccc gct gac tgt<br>Asp Leu Leu Pro Arg Arg Met Gly Gly Ser Gly Leu Pro Ala Asp Cys<br>                645                 650                 655 | 1968 | |

```
ggc ccg cac gac ccc agc ctg gcg ccc cct cct ccg cct ggt ggc tcg        2016
Gly Pro His Asp Pro Ser Leu Ala Pro Pro Pro Pro Pro Gly Gly Ser
            660                 665                 670 ggg gtg ctg ttc cgg ggc cct ctg cag gag ccg atg agg atg ccc gga        2064
Gly Val Leu Phe Arg Gly Pro Leu Gln Glu Pro Met Arg Met Pro Gly
        675                 680                 685 gag ggc cac gtg ccc gcg ctg cct tca ccg ggc ctg cag ttc ggg ggc        2112
Glu Gly His Val Pro Ala Leu Pro Ser Pro Gly Leu Gln Phe Gly Gly
    690                 695                 700 agt ctg gga ggc ctg ggt cag ctg cag tcg ccc ggg gcg ggc gtg ggg        2160
Ser Leu Gly Gly Leu Gly Gln Leu Gln Ser Pro Gly Ala Gly Val Gly
705                 710                 715                 720 ctc ccc agc gct gct tcg gag cgc cgg ccc ccg ccg gac ttt gct            2208
Leu Pro Ser Ala Ala Ser Glu Arg Arg Pro Pro Pro Asp Phe Ala
                725                 730                 735 acg tct gcg ctc ggg ggc cag ccg ggc ttt ccg ttt ggt gca gcc ggc        2256
Thr Ser Ala Leu Gly Gly Gln Pro Gly Phe Pro Phe Gly Ala Ala Gly
            740                 745                 750 cgg cag tcc acg ccg cac agc ggt cca ggc gtg aac tcg ccc ccc agc        2304
Arg Gln Ser Thr Pro His Ser Gly Pro Gly Val Asn Ser Pro Pro Ser
        755                 760                 765 gcg gga ggg ggc ggt ggc agc tct ggt ggc ggc ggt ggc ggg ggt gcc        2352
Ala Gly Gly Gly Gly Ser Gly Gly Gly Gly Gly Gly Ala
    770                 775                 780 tac ccg ccg cag cct gat ttc cag ccc agc cag cgc acc tcg gcc agt        2400
Tyr Pro Pro Gln Pro Asp Phe Gln Pro Ser Gln Arg Thr Ser Ala Ser
785                 790                 795                 800 aaa ttg ggc gcg ctc tcg ctg ggc tcc ttc aac aag ccc agc tcc aag        2448
Lys Leu Gly Ala Leu Ser Leu Gly Ser Phe Asn Lys Pro Ser Ser Lys
            805                 810                 815 gac aac ctg ttc ggc cag agc tgc ctg gct gcg ctc tcc acc gct tgc        2496
Asp Asn Leu Phe Gly Gln Ser Cys Leu Ala Ala Leu Ser Thr Ala Cys
        820                 825                 830 cag aac atg atc gcc agc ctc ggg gcc ccc aac ctc aac gtg acc ttc        2544
Gln Asn Met Ile Ala Ser Leu Gly Ala Pro Asn Leu Asn Val Thr Phe
    835                 840                 845 aac aag aag aac ccg cca gag ggc aag agg aaa ctg agc cag aac gag        2592
Asn Lys Lys Asn Pro Pro Glu Gly Lys Arg Lys Leu Ser Gln Asn Glu
850                 855                 860 acc gac ggc gcg gca gtg gcc ggc aac ccg ggc tcg gat tac ttc cca        2640
Thr Asp Gly Ala Ala Val Ala Gly Asn Pro Gly Ser Asp Tyr Phe Pro
865                 870                 875                 880 gga ggg act gct cct ggg gcc cca gga ccc gga ggc ccg tcc ggg acc        2688
Gly Gly Thr Ala Pro Gly Ala Pro Gly Pro Gly Gly Pro Ser Gly Thr
            885                 890                 895 agt agc agc ggc tcc aaa gcc tcg ggg ccg ccc aac cct cca gcc cag        2736
Ser Ser Ser Gly Ser Lys Ala Ser Gly Pro Pro Asn Pro Pro Ala Gln
        900                 905                 910 ggg gac ggc acc agc ctc tcc ccc aac tac acc ctg gaa tcc acg tcg        2784
Gly Asp Gly Thr Ser Leu Ser Pro Asn Tyr Thr Leu Glu Ser Thr Ser
    915                 920                 925 ggg aat gac ggc aag ccg gtc tcc ggg ggc ggc cgg gga cgg ggt            2832
Gly Asn Asp Gly Lys Pro Val Ser Gly Gly Gly Arg Gly Arg Gly
930                 935                 940 cgc aga aaa agg gac agt ggt cac gtg agc cct ggc acc ttc ttt gac        2880
Arg Arg Lys Arg Asp Ser Gly His Val Ser Pro Gly Thr Phe Phe Asp
945                 950                 955                 960 aag tac tcg gcg gct ccg gac agc ggg ggc gca cct ggg gtg agc cca        2928
Lys Tyr Ser Ala Ala Pro Asp Ser Gly Gly Ala Pro Gly Val Ser Pro
            965                 970                 975
```

```
ggg cag cag caa gcg tca ggc gca gcc gtc ggg gga agc tcc gca ggc    2976
Gly Gln Gln Gln Ala Ser Gly Ala Ala Val Gly Gly Ser Ser Ala Gly
            980                 985                 990 gag acg cgc ggg gca ccg acg ccc cac gaa aag gcg ctc acg tcg cca    3024
Glu Thr Arg Gly Ala Pro Thr Pro His Glu Lys Ala Leu Thr Ser Pro
    995                 1000                1005 tcc tgg ggg aag ggg gct gag ttg ctc ctg ggg gat cag ccg gac        3069
Ser Trp Gly Lys Gly Ala Glu Leu Leu Leu Gly Asp Gln Pro Asp
    1010                1015                1020 ctc att ggg tcc ctg gac ggc ggg gcc aag tcg gac agt agt tcg        3114
Leu Ile Gly Ser Leu Asp Gly Gly Ala Lys Ser Asp Ser Ser Ser
    1025                1030                1035 cca aac gtg ggt gag ttc gcc tcg gac gag gtg agc acg agc tac        3159
Pro Asn Val Gly Glu Phe Ala Ser Asp Glu Val Ser Thr Ser Tyr
    1040                1045                1050 gcc aat gag gac gag gtg tcg tcc agc tct gac aac ccc cag gca        3204
Ala Asn Glu Asp Glu Val Ser Ser Ser Ser Asp Asn Pro Gln Ala
    1055                1060                1065 cta gtt aaa gcg agc agg agt ccc ctg gtg acc ggc tcg ccc aaa        3249
Leu Val Lys Ala Ser Arg Ser Pro Leu Val Thr Gly Ser Pro Lys
    1070                1075                1080 ctc cct ccc cgt ggg gta ggc gcc ggg gaa cac gga ccg aag gcg        3294
Leu Pro Pro Arg Gly Val Gly Ala Gly Glu His Gly Pro Lys Ala
    1085                1090                1095 ccc ccg ccc gcc ctc ggc ctg ggc atc atg tct aac tct acc tcg        3339
Pro Pro Pro Ala Leu Gly Leu Gly Ile Met Ser Asn Ser Thr Ser
    1100                1105                1110 acc cct gac agc tac ggc ggc ggt ggg ggc ccg ggc cat ccg ggc        3384
Thr Pro Asp Ser Tyr Gly Gly Gly Gly Gly Pro Gly His Pro Gly
    1115                1120                1125 act ccg ggc ctg gag cag gtc cgc acc ccg acg agc agc agc ggc        3429
Thr Pro Gly Leu Glu Gln Val Arg Thr Pro Thr Ser Ser Ser Gly
    1130                1135                1140 gcc ccg cca ccc gac gag atc cac ccc ctg gag atc ctt cag gcg        3474
Ala Pro Pro Pro Asp Glu Ile His Pro Leu Glu Ile Leu Gln Ala
    1145                1150                1155 cag atc cag cta cag agg cag cag ttc agc atc tcc gag gac cag        3519
Gln Ile Gln Leu Gln Arg Gln Gln Phe Ser Ile Ser Glu Asp Gln
    1160                1165                1170 cct ctg ggg ctg aag ggt ggc aag aag ggt gag tgc gcc gtc ggg        3564
Pro Leu Gly Leu Lys Gly Gly Lys Lys Gly Glu Cys Ala Val Gly
    1175                1180                1185 gcc tca ggg gcg cag aat ggc gac agc gag ctg ggc agc tgc tgc        3609
Ala Ser Gly Ala Gln Asn Gly Asp Ser Glu Leu Gly Ser Cys Cys
    1190                1195                1200 tcc gag gcg gtc aag agc gcc atg agc acc att gac ctg gac tcg        3654
Ser Glu Ala Val Lys Ser Ala Met Ser Thr Ile Asp Leu Asp Ser
    1205                1210                1215 ctg atg gca gag cac agc gct gcc tgg tac atg ccc gct gac aag        3699
Leu Met Ala Glu His Ser Ala Ala Trp Tyr Met Pro Ala Asp Lys
    1220                1225                1230 gcc ctg gtg gac agc gcg gac gac aag acg ttg gcg ccc tgg            3744
Ala Leu Val Asp Ser Ala Asp Asp Lys Thr Leu Ala Pro Trp
    1235                1240                1245 gag aag gcc aaa ccc cag aac ccc aac agc aaa gaa gcc cac gac        3789
Glu Lys Ala Lys Pro Gln Asn Pro Asn Ser Lys Glu Ala His Asp
    1250                1255                1260 ctc cct gca aac aag gcc tca gca tcc cag cct ggc agc cac ttg        3834
Leu Pro Ala Asn Lys Ala Ser Ala Ser Gln Pro Gly Ser His Leu
```

```
                    1265                1270                1275
cag  tgc  ctg  tct  gtc  cac  tgc  aca  gac  gac  gtg  ggt  gac  gcc  aag    3879
Gln  Cys  Leu  Ser  Val  His  Cys  Thr  Asp  Asp  Val  Gly  Asp  Ala  Lys
          1280                     1285                     1290 gct  cga  gcc  tcc  gtg  ccc  acc  tgg  cgg  tcc  ctg  cat  tct  gac  atc    3924
Ala  Arg  Ala  Ser  Val  Pro  Thr  Trp  Arg  Ser  Leu  His  Ser  Asp  Ile
     1295                     1300                     1305 tcc  aac  aga  ttt  ggg  aca  ttc  gtg  gct  gcc  cta  act  tga               3963
Ser  Asn  Arg  Phe  Gly  Thr  Phe  Val  Ala  Ala  Leu  Thr
1310                1315                     1320
```

<210> SEQ ID NO 8
<211> LENGTH: 1320
<212> TYPE: PRT
<213> ORGANISM: Homo sapiens

<400> SEQUENCE: 8

```
Met Phe Gly Leu Asp Gln Phe Glu Pro Gln Val Asn Ser Arg Asn Ala
1               5                   10                  15

Gly Gln Gly Glu Arg Asn Phe Asn Glu Thr Gly Leu Ser Met Asn Thr
            20                  25                  30

His Phe Lys Ala Pro Ala Phe His Thr Gly Gly Pro Gly Pro Val
        35                  40                  45

Asp Pro Ala Met Ser Ala Leu Gly Glu Pro Pro Ile Leu Gly Met Asn
50                  55                  60

Met Glu Pro Tyr Gly Phe His Ala Arg Gly His Ser Glu Leu His Ala
65                  70                  75                  80

Gly Gly Leu Gln Ala Gln Pro Val His Gly Phe Phe Gly Gln Gln
                85                  90                  95

Pro His His Gly His Pro Gly Ser His His Pro His Gln His His Pro
            100                 105                 110

His Phe Gly Gly Asn Phe Gly Gly Pro Asp Pro Gly Ala Ser Cys Leu
        115                 120                 125

His Gly Gly Arg Leu Leu Gly Tyr Gly Gly Ala Ala Gly Gly Leu Gly
130                 135                 140

Ser Gln Pro Pro Phe Ala Glu Gly Tyr Glu His Met Ala Glu Ser Gln
145                 150                 155                 160

Gly Pro Glu Ser Phe Gly Pro Gln Arg Pro Gly Asn Leu Pro Asp Phe
                165                 170                 175

His Ser Ser Gly Ala Ser Ser His Ala Val Pro Ala Pro Cys Leu Pro
            180                 185                 190

Leu Asp Gln Ser Pro Asn Arg Ala Ser Phe His Gly Leu Pro Ser
        195                 200                 205

Ser Ser Gly Ser Asp Ser His Ser Leu Glu Pro Arg Arg Val Thr Asn
210                 215                 220

Gln Gly Ala Val Asp Ser Leu Glu Tyr Asn Tyr Pro Gly Glu Ala Pro
225                 230                 235                 240

Ser Gly His Phe Asp Met Phe Ser Pro Asp Ser Glu Gly Gln Leu
                245                 250                 255

Pro His Tyr Ala Ala Gly Arg Gln Val Pro Gly Gly Ala Phe Pro Gly
            260                 265                 270

Ala Ser Ala Met Pro Arg Ala Ala Gly Met Val Gly Leu Ser Lys Met
        275                 280                 285

His Ala Gln Pro Pro Gln Gln Pro Gln Gln Gln Gln Pro Gln
290                 295                 300
```

```
Gln Gln Gln Gln Gln His Gly Val Phe Phe Glu Arg Phe Ser Gly Ala
305                 310                 315                 320

Arg Lys Met Pro Val Gly Leu Glu Pro Ser Val Gly Ser Arg His Pro
            325                 330                 335

Leu Met Gln Pro Pro Gln Gln Ala Pro Pro Pro Gln Gln Gln Pro
            340                 345                 350

Pro Gln Gln Pro Pro Gln Gln Gln Pro Pro Pro Pro Gly Leu Leu
            355                 360                 365

Val Arg Gln Asn Ser Cys Pro Pro Ala Leu Pro Arg Pro Gln Gln Gly
370                 375                 380

Glu Ala Gly Thr Pro Ser Gly Gly Leu Gln Asp Gly Gly Pro Met Leu
385                 390                 395                 400

Pro Ser Gln His Ala Gln Phe Glu Tyr Pro Ile His Arg Leu Glu Asn
                405                 410                 415

Arg Ser Met His Pro Tyr Ser Glu Pro Val Phe Ser Met Gln His Pro
                420                 425                 430

Pro Pro Gln Gln Ala Pro Asn Gln Arg Leu Gln His Phe Asp Ala Pro
            435                 440                 445

Pro Tyr Met Asn Val Ala Lys Arg Pro Arg Phe Asp Phe Pro Gly Ser
450                 455                 460

Ala Gly Val Asp Arg Cys Ala Ser Trp Asn Gly Ser Met His Asn Gly
465                 470                 475                 480

Ala Leu Asp Asn His Leu Ser Pro Ser Ala Tyr Pro Gly Leu Pro Gly
                485                 490                 495

Glu Phe Thr Pro Pro Val Pro Asp Ser Phe Pro Ser Gly Pro Pro Leu
            500                 505                 510

Gln His Pro Ala Pro Asp His Gln Ser Leu Gln Gln Gln Gln Gln Gln
515                 520                 525

Gln Gln Gln Gln Gln Gln Gln Gln Gln Gln Gln Gln Gln Gln
530                 535                 540

Gln Gln Gln Gln Gln Gln Arg Gln Asn Ala Ala Leu Met Ile Lys Gln
545                 550                 555                 560

Met Ala Ser Arg Asn Gln Gln Gln Arg Leu Arg Gln Pro Asn Leu Ala
            565                 570                 575

Gln Leu Gly His Pro Gly Asp Val Gly Gln Gly Gly Leu Val His Gly
            580                 585                 590

Gly Pro Val Gly Gly Leu Ala Gln Pro Asn Phe Glu Arg Glu Gly Gly
            595                 600                 605

Ser Thr Gly Ala Gly Arg Leu Gly Thr Phe Glu Gln Gln Ala Pro His
610                 615                 620

Leu Ala Gln Glu Ser Ala Trp Phe Ser Gly Pro His Pro Pro Gly
625                 630                 635                 640

Asp Leu Leu Pro Arg Arg Met Gly Gly Ser Gly Leu Pro Ala Asp Cys
            645                 650                 655

Gly Pro His Asp Pro Ser Leu Ala Pro Pro Pro Gly Gly Ser
            660                 665                 670

Gly Val Leu Phe Arg Gly Pro Leu Gln Glu Pro Met Arg Met Pro Gly
            675                 680                 685

Glu Gly His Val Pro Ala Leu Pro Ser Pro Gly Leu Gln Phe Gly Gly
            690                 695                 700

Ser Leu Gly Gly Leu Gly Gln Leu Gln Ser Pro Gly Ala Gly Val Gly
705                 710                 715                 720

Leu Pro Ser Ala Ala Ser Glu Arg Arg Pro Pro Pro Asp Phe Ala
```

-continued

```
              725                 730                 735
Thr Ser Ala Leu Gly Gly Gln Pro Gly Phe Pro Phe Gly Ala Ala Gly
                740                 745                 750
Arg Gln Ser Thr Pro His Ser Gly Pro Gly Val Asn Ser Pro Pro Ser
                755                 760                 765
Ala Gly Gly Gly Gly Ser Ser Gly Gly Gly Gly Gly Gly Gly Gly Ala
                770                 775                 780
Tyr Pro Pro Gln Pro Asp Phe Gln Pro Ser Gln Arg Thr Ser Ala Ser
785                 790                 795                 800
Lys Leu Gly Ala Leu Ser Leu Gly Ser Phe Asn Lys Pro Ser Ser Lys
                805                 810                 815
Asp Asn Leu Phe Gly Gln Ser Cys Leu Ala Ala Leu Ser Thr Ala Cys
                820                 825                 830
Gln Asn Met Ile Ala Ser Leu Gly Ala Pro Asn Leu Asn Val Thr Phe
                835                 840                 845
Asn Lys Lys Asn Pro Pro Glu Gly Lys Arg Lys Leu Ser Gln Asn Glu
                850                 855                 860
Thr Asp Gly Ala Ala Val Ala Gly Asn Pro Gly Ser Asp Tyr Phe Pro
865                 870                 875                 880
Gly Gly Thr Ala Pro Gly Ala Pro Gly Pro Gly Pro Ser Gly Thr
                885                 890                 895
Ser Ser Ser Gly Ser Lys Ala Ser Gly Pro Pro Asn Pro Pro Ala Gln
                900                 905                 910
Gly Asp Gly Thr Ser Leu Ser Pro Asn Tyr Thr Leu Glu Ser Thr Ser
                915                 920                 925
Gly Asn Asp Gly Lys Pro Val Ser Gly Gly Gly Arg Gly Arg Gly
                930                 935                 940
Arg Arg Lys Arg Asp Ser Gly His Val Ser Pro Gly Thr Phe Phe Asp
945                 950                 955                 960
Lys Tyr Ser Ala Ala Pro Asp Ser Gly Gly Ala Pro Gly Val Ser Pro
                965                 970                 975
Gly Gln Gln Gln Ala Ser Gly Ala Ala Val Gly Gly Ser Ser Ala Gly
                980                 985                 990
Glu Thr Arg Gly Ala Pro Thr Pro His Glu Lys Ala Leu Thr Ser Pro
                995                1000                1005
Ser Trp Gly Lys Gly Ala Glu Leu Leu Leu Gly Asp Gln Pro Asp
                1010                1015                1020
Leu Ile Gly Ser Leu Asp Gly Gly Ala Lys Ser Asp Ser Ser Ser
                1025                1030                1035
Pro Asn Val Gly Glu Phe Ala Ser Asp Glu Val Ser Thr Ser Tyr
                1040                1045                1050
Ala Asn Glu Asp Glu Val Ser Ser Ser Ser Asp Asn Pro Gln Ala
                1055                1060                1065
Leu Val Lys Ala Ser Arg Ser Pro Leu Val Thr Gly Ser Pro Lys
                1070                1075                1080
Leu Pro Pro Arg Gly Val Gly Ala Gly Glu His Gly Pro Lys Ala
                1085                1090                1095
Pro Pro Pro Ala Leu Gly Leu Gly Ile Met Ser Asn Ser Thr Ser
                1100                1105                1110
Thr Pro Asp Ser Tyr Gly Gly Gly Gly Pro Gly His Pro Gly
                1115                1120                1125
Thr Pro Gly Leu Glu Gln Val Arg Thr Pro Thr Ser Ser Ser Gly
                1130                1135                1140
```

Ala Pro Pro Pro Asp Glu Ile His Pro Leu Glu Ile Leu Gln Ala
    1145                1150                1155

Gln Ile Gln Leu Gln Arg Gln Gln Phe Ser Ile Ser Glu Asp Gln
    1160                1165                1170

Pro Leu Gly Leu Lys Gly Gly Lys Lys Gly Glu Cys Ala Val Gly
    1175                1180                1185

Ala Ser Gly Ala Gln Asn Gly Asp Ser Glu Leu Gly Ser Cys Cys
    1190                1195                1200

Ser Glu Ala Val Lys Ser Ala Met Ser Thr Ile Asp Leu Asp Ser
    1205                1210                1215

Leu Met Ala Glu His Ser Ala Ala Trp Tyr Met Pro Ala Asp Lys
    1220                1225                1230

Ala Leu Val Asp Ser Ala Asp Asp Asp Lys Thr Leu Ala Pro Trp
    1235                1240                1245

Glu Lys Ala Lys Pro Gln Asn Pro Asn Ser Lys Glu Ala His Asp
    1250                1255                1260

Leu Pro Ala Asn Lys Ala Ser Ala Ser Gln Pro Gly Ser His Leu
    1265                1270                1275

Gln Cys Leu Ser Val His Cys Thr Asp Asp Val Gly Asp Ala Lys
    1280                1285                1290

Ala Arg Ala Ser Val Pro Thr Trp Arg Ser Leu His Ser Asp Ile
    1295                1300                1305

Ser Asn Arg Phe Gly Thr Phe Val Ala Ala Leu Thr
    1310                1315                1320

<210> SEQ ID NO 9
<211> LENGTH: 399
<212> TYPE: DNA
<213> ORGANISM: Homo sapiens
<220> FEATURE:
<221> NAME/KEY: CDS
<222> LOCATION: (1)..(399)

<400> SEQUENCE: 9 atg cga cgg ctg ctg atc cct ctg gcc ctg tgg ctg ggt gcg gtg ggc     48
Met Arg Arg Leu Leu Ile Pro Leu Ala Leu Trp Leu Gly Ala Val Gly
1               5                   10                  15 gtg ggc gtc gcc gag ctc acg gaa gcc cag cgc cgg ggc ctg cag gtg     96
Val Gly Val Ala Glu Leu Thr Glu Ala Gln Arg Arg Gly Leu Gln Val
            20                  25                  30 gcc ctg gag gaa ttt cac aag cac ccg ccc gtg cag tgg gcc ttc cag    144
Ala Leu Glu Glu Phe His Lys His Pro Pro Val Gln Trp Ala Phe Gln
        35                  40                  45 gag acc agt gtg gag agc gcc gtg gac acg ccc ttc cca gct gga ata    192
Glu Thr Ser Val Glu Ser Ala Val Asp Thr Pro Phe Pro Ala Gly Ile
    50                  55                  60 ttt gtg agg ctg gaa ttt aag ctg cag cag aca agc tgc cgg aag agg    240
Phe Val Arg Leu Glu Phe Lys Leu Gln Gln Thr Ser Cys Arg Lys Arg
65                  70                  75                  80 gac tgg aag aaa ccc gag tgc aaa gtc agg ccc aat ggg agg aaa cgg    288
Asp Trp Lys Lys Pro Glu Cys Lys Val Arg Pro Asn Gly Arg Lys Arg
                85                  90                  95 aaa tgc ctg gcc tgc atc aaa ctg ggc tct gag gac aaa gtt ctg ggc    336
Lys Cys Leu Ala Cys Ile Lys Leu Gly Ser Glu Asp Lys Val Leu Gly
            100                 105                 110 cgg ttg gtc cac tgc ccc ata gag acc caa gtt ctg cgg ttt tgg gca    384
Arg Leu Val His Cys Pro Ile Glu Thr Gln Val Leu Arg Phe Trp Ala
        115                 120                 125

```
ctg gca gga ggc tga                                                         399
Leu Ala Gly Gly
    130

<210> SEQ ID NO 10
<211> LENGTH: 132
<212> TYPE: PRT
<213> ORGANISM: Homo sapiens

<400> SEQUENCE: 10

Met Arg Arg Leu Leu Ile Pro Leu Ala Leu Trp Leu Gly Ala Val Gly
1               5                   10                  15

Val Gly Val Ala Glu Leu Thr Glu Ala Gln Arg Arg Gly Leu Gln Val
            20                  25                  30

Ala Leu Glu Glu Phe His Lys His Pro Pro Val Gln Trp Ala Phe Gln
        35                  40                  45

Glu Thr Ser Val Glu Ser Ala Val Asp Thr Pro Phe Pro Ala Gly Ile
    50                  55                  60

Phe Val Arg Leu Glu Phe Lys Leu Gln Gln Thr Ser Cys Arg Lys Arg
65                  70                  75                  80

Asp Trp Lys Lys Pro Glu Cys Lys Val Arg Pro Asn Gly Arg Lys Arg
            85                  90                  95

Lys Cys Leu Ala Cys Ile Lys Leu Gly Ser Glu Asp Lys Val Leu Gly
            100                 105                 110

Arg Leu Val His Cys Pro Ile Glu Thr Gln Val Leu Arg Phe Trp Ala
            115                 120                 125

Leu Ala Gly Gly
    130
```

CELL POPULATION INCLUDING ADHESIVE STEM CELLS, PRODUCTION METHOD THEREFOR AND PHARMACEUTICAL COMPOSITION

TECHNICAL FIELD

The present invention relates to a cell population of adherent stem cells such as mesenchymal stem cells. The present invention relates to a method for producing the cell population and a pharmaceutical composition comprising the cell population. The present invention further relates to a method for monitoring karyotypic abnormality of adherent stem cells using a proportion of adherent stem cells expressing a predetermined marker in a cell population as an index, a method for evaluating a donor and/or a biological sample collected from the donor, and a method for determining and/or predicting conditions of enzymatic treatment.

BACKGROUND ART

Adherent stem cells such as mesenchymal stem cells, also called mesenchymal stromal cells, are somatic stem cells reported to exist in the bone marrow, adipose tissues, tooth pulp and the like. Recently, it has been revealed that these cells also exist in fetal appendages including the placenta, umbilical cord, and fetal membrane. Also, the adherent stem cells have immunosuppressive capacity and have been increasingly used in practice for treating acute graft-versus-host disease (GVHD) and inflammatory bowel disease such as Crohn's disease.

Further, in recent years, safe adherent stem cells to be sufficiently used for cell therapy have been desired; for example, Non Patent Literature 1 discloses criteria for karyotypic analysis of mesenchymal stem cells to be applied to cell therapy. Also, in Non Patent Literature 2, the occurrence frequency of karyotypic abnormality in bone marrow-derived mesenchymal stem cells of a plurality of donors and the correlation between passage number and the occurrence frequency of karyotypic abnormality are disclosed.

CITATION LIST

Non-Patent Literatures

Non-Patent Literature 1: Lisbeth Barkholt et al., Risk of tumorigenicity in mesenchymal stromal cell based therapies-Bridging scientific observations and regulatory viewpoints, Cytotherapy, 2013, 15, 753-759
Non-Patent Literature 2: Brian G. Stultz et al., Chromosomal Stability of Mesenchymal Stromal Cells During In Vitro Culture, Cytotherapy, 2016, 18(3), 336-343

SUMMARY OF INVENTION

Object to be Achieved

The present inventors conducted studies with a view to providing safe adherent stem cells to be sufficiently used for cell therapy. As a result, it was found that karyotypic abnormality occurs at a high frequency during a culture process of adherent stem cells and also a problem of accumulation of karyotypic abnormality with an increase of the number of passages. Since above problem causes a risk of tumorigenicity, an adherent stem cell population comprising adherent stem cells confirmed to have karyotypic abnormality has to be totally discarded even if the number of abnormal cells is small. In addition, the analysis for evaluating karyotype by observing the structures of chromosomes one by one to obtain a frequency of karyotypic abnormality requires an enormous amount of time and labor. This is the reason why guarantee of the quality cannot be quickly carried out. Accordingly, the present inventors found that, a cell population having no karyotypic abnormality must be prepared, and the occurrence of karyotypic abnormality must be monitored over time, as objects to be achieved in order to solve the aforementioned problem.

To achieve the objects, the inventors reviewed Non Patent Literature 1. Non Patent Literature 1 discloses criteria for frequency of occurrence of chromosome structural abnormality in mesenchymal stem cells for use in cell therapy. Also, Non Patent Literature 1 suggests that determining culture conditions so as to control the cell proliferation rate and doubling number as low as possible can provide a cell population comprising no karyotypic abnormality. However, the present inventors found that even if the proliferation rate and doubling number are reduced, karyotypic abnormality occurs at a high frequency. A method for monitoring the presence or absence of karyotypic abnormality is not disclosed in Non Patent Literature 1.

Non Patent Literature 2 discloses the occurrence frequency of karyotypic abnormality in bone marrow-derived mesenchymal stem cells of a plurality of donors, and the correlation between the passage number and the occurrence frequency of karyotypic abnormality. It is confirmed that the occurrence frequency of karyotypic abnormality tends to decrease as the number of passages increases and doubling number increases, different from the disclosure of Non Patent Literature 1. Likewise, the relationship between doubling number of cells and the occurrence frequency of karyotypic abnormality differs in tendency between the literatures and occurrence mechanism of karyotypic abnormality is not sufficiently elucidated. In addition, in Non Patent Literature 2, it is mentioned that analyzing the karyotype of mesenchymal stem cells obtained every time passage culture is performed is important for monitoring stability of chromosomes of the mesenchymal stem cells during expansion culture. However, in the karyotypic analysis, after mesenchymal stem cells are obtained, chromosomes to be subjected to karyotypic analysis are extracted from 17 to 144 cells and the structures of the chromosomes are observed one by one in accordance with the SKY (Spectral Karyotyping) method. This analysis requires an enormous amount of time and labor. In addition, it is difficult to monitor occurrence of karyotypic abnormality over time and impossible to quickly evaluate the presence or absence of karyotypic abnormality. Also, the literature is silent about a method for preparing a cell population not comprising karyotypic abnormality.

In view of the aforementioned problems, an object of the present invention is to provide a means for obtaining a cell population comprising adherent stem cells maintaining a normal karyotype; monitoring occurrence of karyotypic abnormality in the cell population comprising adherent stem cells over time; and quickly evaluating the presence or absence of karyotypic abnormality.

Means to Achieve the Object

The present inventors conducted intensive studies with a view to attaining the above object. As a result, it was found that if a cell population comprising adherent stem cells is cultured in such a condition that the proportion of KCNAB1-positive adherent stem cells is maintained at a predetermined value or more, a cell population comprising adherent stem cells maintaining a normal karyotype can be obtained. The present inventors further found that the presence or absence of a karyotypic abnormality of the adherent stem cells can be monitored by using the proportion of KCNAB1-positive adherent stem cells in a cell population comprising adherent stem cells being a predetermined value or more, as an index. It was further found that, from the viewpoint of efficiently obtaining adherent stem cells maintaining a normal karyotype, the quality of a donor and/or a biological sample collected from the donor can be quickly evaluated, and further that optimal enzymatic treatment conditions for a biological sample collected from a donor can be determined and/or predicted. The present invention was accomplished on the basis of these findings.

That is, the following inventions are provided herein.

[1] A producing method of a cell population comprising adherent stem cells, comprising obtaining a cell population in which the proportion of KCNAB1-positive adherent stem cells in the cell population is 85% or more.

[2] A cell population comprising adherent stem cells, wherein the proportion of KCNAB1-positive adherent stem cells in the cell population is 85% or more.

[3] The cell population according to [2], wherein the relative expression level of KCNAB1 gene to the expression level of SDHA gene is 0.05 or more.

[4] The cell population according to [2] or [3], wherein the relative expression level of SULT1E1 gene to the expression level of SDHA gene is 0.1 or more.

[5] The cell population according to any one of [2] to [4], wherein the relative expression level of MN1 gene to the expression level of SDHA gene is 0.7 or more.

[6] The cell population according to any one of [2] to [5], wherein the relative expression level of RARRES2 gene to the expression level of SDHA gene is 0.4 or less.

[7] The cell population according to any one of [2] to [6], wherein the adherent stem cells are derived from a fetal appendage.

[8] A pharmaceutical composition comprising the cell population according to any one of [2] to [7] and a pharmaceutically acceptable vehicle.

[9] The pharmaceutical composition comprising the cell population according to any one of [2] to [7] and additional cells that can be administered.

[10] The pharmaceutical composition according to [8] or [9], wherein a single dose of the adherent stem cells to a human is $10^{12}$ cells/kg body weight or less.

[11] The pharmaceutical composition according to any one of [8] to [10], wherein the pharmaceutical composition is an injectable preparation.

[12] The pharmaceutical composition according to any one of [8] to [10], wherein the pharmaceutical composition is a transplant preparation.

[13] The pharmaceutical composition according to [12], wherein the transplant preparation has a cell aggregate or sheet-like structure.

[14] The pharmaceutical composition according to any one of [8] to [13], being a therapeutic agent for a disease selected from immune-related disease, ischemic disease, lower-limb ischemia, cerebrovascular ischemia, renal ischemia, pulmonary ischemia, neurological disease, graft-versus-host disease, inflammatory bowel disease, Crohn's disease, ulcerative colitis, radiation enteritis, systemic lupus erythematosus, lupus erythematosus, collagen disease, stroke, cerebral infarction, intracerebral hematoma, cerebrovascular paralysis, liver cirrhosis, atopic dermatitis, multiple sclerosis, psoriasis, epidermolysis bullosa, diabetes mellitus, mycosis fungoides, scleroderma, disease caused by the degeneration and/or inflammation of connective tissues such as cartilage, articular cartilage defect, meniscal damage, osteochondritis dissecans, aseptic necrosis, knee osteoarthritis, inflammatory arthritis, rheumatoid arthritis, eye disease, angiogenesis-related disease, ischemic heart disease, coronary heart disease, myocardial infarction, angina pectoris, cardiac failure, cardiomyopathy, valvular disease, wound, epithelial damage, fibrosis, lung disease and cancer.

[15] A method for monitoring karyotypic abnormality of adherent stem cells, comprising measuring a proportion of KCNAB1-positive adherent stem cells in a cell population comprising the adherent stem cells and using the proportion of KCNAB1-positive adherent stem cells in the cell population being 85% or more as an index.

[16] A method for evaluating a donor and/or a biological sample collected from the donor, comprising collecting a cell population comprising adherent stem cells from the donor, measuring a proportion of KCNAB1-positive adherent stem cells and performing evaluation based on the proportion of KCNAB1-positive adherent stem cells in the cell population being 85% or more as an index.

[17] A method for determining and/or predicting enzymatic treatment condition of a biological sample collected from a donor, comprising measuring a proportion of KCNAB1-positive adherent stem cells to a cell population obtained by enzymatic treatment of the biological sample, and performing evaluation based on the proportion of KCNAB1-positive adherent stem cells in the cell population being 85% or more, as an index.

[21] A method for treating a disease, comprising administering the cell population according to any one of [2] to [7] to a patient or a subject in need of treatment.

[22] The method according to [21], wherein a single dose of the adherent stem cells to a human is $1 \times 10^{12}$ cells/kg body weight or less.

[23] The method according to [21] or [22], being an injectable preparation.

[24] The method according to [21] or [22], being a transplant preparation.

[25] The pharmaceutical composition according to [24], wherein the transplant preparation is a cell aggregate or sheet-like structure.

[26] The method according to any one of [21] to [25], wherein the disease is a disease selected from immune-related disease, ischemic disease, lower-limb ischemia, cerebrovascular ischemia, renal ischemia, pulmonary ischemia, neurological disease, graft-versus-host disease, inflammatory bowel disease, Crohn's disease, ulcerative colitis, radiation enteritis, systemic lupus erythematosus, lupus erythematosus, collagen disease, stroke, cerebral infarction, intracerebral hematoma, cerebrovascular paralysis, liver cirrhosis, atopic dermatitis, multiple sclerosis, psoriasis, epidermolysis bullosa, diabetes mellitus, mycosis fungoides, scleroderma, disease caused by the degeneration and/or inflammation of connective tissues such as cartilage, articular cartilage defect, meniscal damage, osteochondritis dissecans, aseptic necrosis, knee osteoarthritis, inflammatory arthritis, rheumatoid arthritis, eye disease, angiogenesis-related disease, ischemic heart disease, coronary heart disease, myocardial infarction, angina pectoris, cardiac failure, cardiomyopathy, valvular disease, wound, epithelial damage, fibrosis, lung disease and cancer.

[31] Use of the cell population according to any one of [2] to [6] for the manufacture of a pharmaceutical composition.

[32] Use according to [31], wherein the pharmaceutical composition is a pharmaceutical composition where a single dose of the adherent stem cells to a human is $1\times10^{12}$ cells/kg body weight or less.

[33] Use according to [31] or [32], wherein the pharmaceutical composition is an injectable preparation.

[34] Use according to [31] or [32], wherein the pharmaceutical composition is a transplant preparation.

[35] The pharmaceutical composition according to [34], wherein the transplant preparation is a cell aggregate or sheet-like structure.

[36] Use of any one of [31] to [35], wherein the pharmaceutical composition is a therapeutic agent for a disease selected from immune-related disease, ischemic disease, lower-limb ischemia, cerebrovascular ischemia, renal ischemia, pulmonary ischemia, neurological disease, graft-versus-host disease, inflammatory bowel disease, Crohn's disease, ulcerative colitis, radiation enteritis, systemic lupus erythematosus, lupus erythematosus, collagen disease, stroke, cerebral infarction, intracerebral hematoma, cerebrovascular paralysis, liver cirrhosis, atopic dermatitis, multiple sclerosis, psoriasis, epidermolysis bullosa, diabetes mellitus, mycosis fungoides, scleroderma, disease caused by the degeneration and/or inflammation of connective tissues such as cartilage, articular cartilage defect, meniscal damage, osteochondritis dissecans, aseptic necrosis, knee osteoarthritis, inflammatory arthritis, rheumatoid arthritis, eye disease, angiogenesis-related disease, ischemic heart disease, coronary heart disease, myocardial infarction, angina pectoris, cardiac failure, cardiomyopathy, valvular disease, wound, epithelial damage, fibrosis, lung disease and cancer.

[41] The cell population according to any one of [2] to [6], for use in the treatment of a disease.

[42] The cell population according to [41], wherein a single dose of the adherent stem cells to a human is $1\times10^{12}$ cells/kg body weight or less.

[43] The cell population according to [41] or [42], being an injectable preparation.

[44] The cell population according to [41] or [42], being a transplant preparation.

[45] The pharmaceutical composition according to [44], wherein the transplant preparation is a cell aggregate or sheet-like structure.

[46] The cell population according to any one of [41] to [45], wherein the disease is a disease selected from immune-related disease, ischemic disease, lower-limb ischemia, cerebrovascular ischemia, renal ischemia, pulmonary ischemia, neurological disease, graft-versus-host disease, inflammatory bowel disease, Crohn's disease, ulcerative colitis, radiation enteritis, systemic lupus erythematosus, lupus erythematosus, collagen disease, stroke, cerebral infarction, intracerebral hematoma, cerebrovascular paralysis, liver cirrhosis, atopic dermatitis, multiple sclerosis, psoriasis, epidermolysis bullosa, diabetes mellitus, mycosis fungoides, scleroderma, disease caused by the degeneration and/or inflammation of connective tissues such as cartilage, articular cartilage defect, meniscal damage, osteochondritis dissecans, aseptic necrosis, knee osteoarthritis, inflammatory arthritis, rheumatoid arthritis, eye disease, angiogenesis-related disease, ischemic heart disease, coronary heart disease, myocardial infarction, angina pectoris, cardiac failure, cardiomyopathy, valvular disease, wound, epithelial damage, fibrosis, lung disease and cancer.

Advantageous Effects of Invention

According to the present invention, a cell population comprising adherent stem cells maintaining a normal karyotype can be obtained. According to the present invention, a means for quickly evaluating the presence or absence of karyotypic abnormality by monitoring occurrence of karyotypic abnormality over time in a cell population comprising adherent stem cells, can be also provided. According to the present invention, the positive rate of a predetermined antigen can be used as an index for formation of a cell population comprising safe adherent stem cells maintaining a normal karyotype. According to the present invention, a safe cell preparation (pharmaceutical composition) having high chromosomal stability and suitable for clinical use can be manufactured.

BRIEF DESCRIPTION OF DRAWINGS

FIG. 1 shows the results of the proportion of KCNAB1-positive cells in amniotic adherent stem cells obtained from fetal appendages of 5 pregnant women analyzed by a flow cytometer.

EMBODIMENTS FOR CARRYING OUT THE INVENTION

Embodiments of the present invention will be specifically described below. The descriptions below are intended to facilitate understanding of the present invention. Thus, the scope of the present invention is not limited to the following embodiments. Other embodiments, which may be obtained as appropriate by replacing features of the following embodiments, are also included in the scope of the present invention.

[1] Explanation of Terms

The term "fetal appendage" used herein refers to a fetal membrane, a placenta, an umbilical cord, and amniotic fluid. In addition, the term "fetal membrane" refers to a fetal sac comprising fetal amniotic fluid, which consists of an amnion, a chorion, and a decidua in that order from the inside. Among them, the amnion and the chorion are originated from the fetus. The term "amnion" refers to a transparent thin membrane with few blood vessels, which is located in the most inner layer of the fetal membrane. The inner layer (also called epithelial cell layer) of the amnion is covered with a layer of epithelial cells having a secretory function and secretes amniotic fluid. The outer layer (also called extracellular matrix layer, which corresponds to the stroma) of the amnion comprises adherent stem cells.

The term "adherent stem cells" used herein refers to stem cells that satisfy the definition described below and "mesenchymal stromal cells" and "mesenchymal stem cells" are also included in the adherent stem cells. The term "mesenchymal stem cells" is also referred to as "MSCs" in the specification.

As the term "adherent stem cells", somatic stem cells (tissue stem cells) taken from various tissues and organs and satisfying the following definition can be used. Examples of the somatic stem cells (tissue stem cells) include, but are not particularly limited to, bone marrow-derived mesenchymal stem cells, hematopoietic stem cells, stem cells in umbilical blood, umbilical cord-derived stem cells, amnion-derived stem cells, amniotic fluid stem cells, placental villus cell-derived mesenchymal stem cells, neural stem cells, adipose tissue-derived stem cells, pancreatic stem cells, synovial mesenchymal stem cells, dental pulp stem cells, stem cells from pulp from deciduous milk teeth, germline stem cells (GS cells), multipotent germline stem cells (mGS cells), corneal epithelial stem cells, corneal parenchymal stem cells, pigment stem cells and tissue stem cells in organs.

Definition of Adherent Stem Cells i) Adherence to plastics under culture conditions in a standard medium.

ii) Positive for surface antigens CD73 and CD90, and negative for surface antigen CD326.

The "adherent stem cells" are not particularly limited as long as they satisfy the definitions in i) ii) above and are not particularly restricted by the presence or absence of differentiation capacity into bone, cartilage, adipose and the like. Cells having differentiation capacity into bone, cartilage and adipose, like mesenchymal stem cells are included in the "adherent stem cells" herein. In addition, the cells that satisfy the above definitions but fail to have differentiation capacity into bone, cartilage, adipose are also included in the "adherent stem cells". In addition, the cells that satisfy the above definitions and differentiate only into any one or two of bone, cartilage and adipose are also included in the "adherent stem cells".

The term "amnion-derived adherent stem cells" used herein, refers to adherent stem cells derived from the amnion and "amniotic mesenchymal stromal cells" and "amniotic mesenchymal stem cells" are also included in the term. The term "amniotic mesenchymal stem cells" used herein is also referred to as "amniotic MSCs".

The term "adherent stem cell population" used herein means a cell population comprising adherent stem cells. Examples of the form thereof include, but are not particularly limited to, cell pellets, cell sheets, cell aggregates, cell-floated liquids and cell suspensions.

The term "karyotypic abnormality" used herein refers to chromosome structural abnormality and means numerical aberration of chromosomes and partial chromosome structural abnormality. Examples of the numerical aberration include "monosomy" having only one chromosome instead of the usual pair of chromosomes and "trisomy" having three chromosomes. Examples of the partial chromosome structural abnormality include translocation, inversion and deletion.

The term "normal karyotype" used herein refers to a karyotype having no karyotypic abnormality as mentioned above or a karyotype close to normal.

The "normal karyotype" and "karyotypic abnormality" can be evaluated by karyotypic analysis. Specifically, the "normal karyotype" and "karyotypic abnormality" can be evaluated by identifying individual chromosomes based on characteristic band pattern to chromosome detected by a differential staining technique and analyzing, e.g., numerical aberration and partial structural abnormality. The type of karyotypic analysis is not particularly limited. Examples thereof known in the art include Q-band analysis using a fluorescent dye such as quinacrine mustard and Hoechst for detection; G-band analysis using a treatment with a protease such as trypsin and detection with Giemsa staining; a multi-color FISH method for coloring chromosomes with different colors and a simple analytical method by Giemsa staining. Any one of the methods may be used in the present invention. For example, for determining karyotypic abnormality, chromosome is extracted from 20 cells and subjected to karyotypic analysis. In this manner, the presence or absence of karyotypic abnormality can be evaluated. As the criteria for a normal karyotype, it is preferable that the proportion of cells having karyotypic abnormality in 20 cells subjected to analysis is 10% or less, more preferably 5% or less, further preferably 4% or less, further preferably 3% or less, further preferably 2% or less, further preferably 1% or less and further preferably 0%.

The phrase "proportion of KCNAB1-positive adherent stem cells" used herein refers to the proportion of cells positive for the antigen analyzed by flow cytometry, as described in Examples mentioned later. The phrase "proportion of antigen-positive cells" is also referred to as a "positive rate" in the specification.

[2] Cell Population Comprising Adherent Stem Cells

The cell population comprising adherent stem cells and provided by the present invention is characterized in that the proportion of KCNAB1-positive adherent stem cells in the cell population is 85% or more.

In addition, if the cell population comprising adherent stem cells and provided by the present invention satisfies the condition that the proportion of KCNAB1-positive adherent stem cells is 85% or more, a cell population comprising adherent stem cells maintaining a normal karyotype is formed. Because of this, in the present invention, the above condition can be used as an index for formation of a cell population comprising adherent stem cells maintaining a normal karyotype. Also, a change in karyotypic abnormality of adherent stem cells can be quickly and easily determined and predicted by measuring the index over time. Further, according to the present invention, the quality of a donor itself and/or a biological sample collected from the donor can be evaluated by using the index. Further, according to the present invention, the enzyme treatment method for treating a biological sample collected from a donor with an enzyme is appropriate or not can be determined and/or predicted by using the index. Also, in addition to the above index, predetermined numerical ranges in which relative expression levels of KCNAB1 gene, SULT1E1 gene, MN1 gene, and RARRES2 gene fall, can be used as indices for formation of a cell population comprising adherent stem cells maintaining a normal karyotype.

The proportion of KCNAB1-positive adherent stem cells in the cell population is preferably 86% or more, further preferably 87% or more, further preferably 88% or more, further preferably 89% or more, further preferably 90% or more, further preferably 91% or more, further preferably 92% or more, further preferably 93% or more, further preferably 94% or more, further preferably 95% or more, further preferably 96% or more, further preferably 97% or more, further preferably 98% or more, further preferably 99% or more, and further preferably 100%.

According to an aspect of the present invention, the cell population comprising adherent stem cells and provided by the present invention may satisfy a condition that a proportion of CD105, CD73, and/or CD90-positive adherent stem cells is 90% or more.

CD105, which means cluster of differentiation 105, is a protein also known as Endoglin.

CD73, which means cluster of differentiation 73, is a protein also known as 5-Nucleotidase or Ecto-5'-nucleotidase.

CD90, which means cluster of differentiation 90, is a protein also known as Thy-1.

The proportion of CD105-positive adherent stem cells in a cell population may be 91% or more, 92% or more, 93% or more, 94% or more, 95% or more, 96% or more, 97% or more, 98% or more, 99% or more, or 100%.

The proportion of CD73-positive adherent stem cells in a cell population may be 91% or more, 92% or more, 93% or more, 94% or more, 95% or more, 96% or more, 97% or more, 98% or more, 99% or more, or 100%.

The proportion of CD90-positive adherent stem cells in a cell population may be 91% or more, 92% or more, 93% or more, 94% or more, 95% or more, 96% or more, 97% or more, 98% or more, 99% or more, or 100%.

According to an aspect of the present invention, the cell population comprising adherent stem cells and provided by the present invention may satisfy a proportion of CD166-positive adherent stem cells of 30% or more.

CD166, which means cluster of differentiation 166, is a protein also known as Activated leukocyte cell adhesion molecule (ALCAM).

The proportion of CD166-positive adherent stem cells in a cell population may be 31% or more, 32% or more, 33% or more, 34% or more, 35% or more, 36% or more, 37% or more, 38% or more, 39% or more, 40% or more, 41% or more, 42% or more, 43% or more, 44% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more, or 100%.

According to an aspect of the present invention, the cell population comprising adherent stem cells and provided by the present invention may satisfy a proportion of CD45, CD34, and/or CD326-negative adherent stem cells of 95% or more.

CD45, which means cluster of differentiation 45, is a protein also known as PTPRC (Protein tyrosine phosphatase, receptor type C) or LCA (Leukocyte common antigen).

CD34, which means cluster of differentiation 34, is a protein also known as Hematopoietic progenitor cell antigen CD34.

CD326, which means cluster of differentiation 326, is a protein also known as an epithelial cell adhesion molecule encoded by EPCAM gene.

The proportion of CD45-negative adherent stem cells in a cell population may be 96% or more, 97% or more, 98% or more, 99% or more, or 100%.

The proportion of CD34-negative adherent stem cells in a cell population may be 96% or more, 97% or more, 98% or more, 99% or more, or 100%.

The proportion of CD326-negative adherent stem cells in a cell population may be 96% or more, 97% or more, 98% or more, 99% or more, or 100%.

Individual antigens including KCNAB1, CD73, CD90, CD166, CD34, CD45 and CD326 can be detected by any detection method as long as it is known in the art. Examples of the method for detecting these antigens include, but are not limited to, flow cytometry and cell staining. In the flow cytometry using a fluorescently labeled antibody, if cells emitting higher fluorescence than the cells of a negative control (isotype control) are detected, the cells are determined as being "positive" for the marker. As the fluorescently labeled antibody, any antibody can be used as long as it is known in the art and examples thereof include antibodies labeled with, e.g., fluorescein isothiocyanate (FITC), phycoerythrin (PE) and allophycocyanin (APC), respectively; however, examples are not limited to these. In the cell staining, when cells that are colored or emit fluorescence were observed by a microscope, the cells are determined as being "positive" for the marker. The cell staining may be immunostaining using an antibody or non-immunostaining not using an antibody.

The proportion (positive rate) of KCNAB1-positive cells can be measured specifically by flow cytometry dot-plot analysis by the following procedures (1) to (8).

(1) A cryopreserved cell population is thawed and centrifugally collected. The collected cell population is washed with phosphate buffer (PBS) and centrifugally collected.

(2) The cells are fixed with a solution prepared by adding polyoxyethylene (10) octyl phenyl ether (Triton-X) to 4% paraformaldehyde so as to obtain a final concentration of 0.1%. The cell suspension is passed through membrane filtration. The cells are washed with phosphate buffer (PBS) and a cell suspension is prepared in 0.5% BSA/PBS at $2.0 \times 10^6$ cells/mL. The cell suspension is dispensed in 100 μL each.

(3) The dispensed cell suspensions are centrifuged and 100 μL of 0.5% BSA/PBS is each added to the obtained cell pellets, followed by addition of antibodies against the respective antigen markers or the isotype control antibodies thereof. Each reaction solution is mixed by vortexing and then allowed to stand at 4° C. for 20 minutes.

(4) The cell is centrifugally washed by addition of 0.5% BSA/PBS, suspended in 0.5% BSA/PBS and filtered through a cell strainer (35-μm-nylon mesh filter) (Corning Inc./Product number: 352235).

(5) The cell suspension obtained by filtration is analyzed by using a BD Accuri™ C6 Flow Cytometer (Becton, Dickinson and Company) (ALL Event 10000).

(6) The measurement results are plotted as dots with SSC (side scattered light) on the vertical axis and FSC (forward-scattered light) on the horizontal axis.

(7) In the dot plot diagram, all regions (gates) in which the cell population with stronger fluorescence intensity is 0.5% or less from all cells measured with the isotype control antibodies are selected.

(8) The proportion of cells comprised in the gate selected in (7) among all cells measured with the antibody against the antigen marker is calculated.

Note that, the proportion of cells negative for each surface antigen (negative rate) is calculated by the following equation:

Negative rate (%)=100−positive rate

The timing for detecting KCNAB1 described above is not particularly limited, and examples thereof include immediately after separation of cells from a biological sample, during a culture step, after purification in the culture step, immediately after n times passages (n represents an integer of 1 or more), during maintenance culture, before cryopreservation, after thawing and before formulation as a pharmaceutical composition.

The cell population comprising adherent stem cells and provided by the present invention preferably satisfies the relative expression level of KCNAB1 gene to the expression level of SDHA gene of 0.05 or more.

The relative expression level of KCNAB1 gene to the expression level of SDHA gene may be 0.75 or more, 0.1 or more, 0.15 or more, 0.2 or more, 0.25 or more, 0.3 or more, 0.35 or more, or 0.4 or more. The upper limit of the relative expression level of KCNAB1 gene to the expression level of SDHA gene is not particularly limited, and may be, for example, 5 or less, 4 or less, 3 or less, 2 or less, 1 or less, 0.9 or less, 0.8 or less, 0.7 or less or 0.6 or less.

The cell population comprising adherent stem cells and provided by the present invention preferably satisfies the relative expression level of SULT1E1 gene to the expression level of SDHA gene of 0.1 or more.

The relative expression level of SULT1E1 gene to the expression level of SDHA gene may be 0.13 or more, 0.15 or more, 0.2 or more, 0.3 or more, 0.4 or more, 0.5 or more, or 0.6 or more. The upper limit of the relative expression level of SULT1E1 gene to the expression level of SDHA gene is not particularly limited, and may be, for example, 5 or less, 4 or less, 3 or less, 2 or less, 1 or less, 0.9 or less, 0.8 or less, 0.7 or less, 0.6 or less, or 0.5 or less.

The cell population comprising adherent stem cells and provided by the present invention preferably satisfies the relative expression level of MN1 gene to the expression level of SDHA gene of 0.7 or more.

The relative expression level of MN1 gene to the expression level of SDHA gene may be 0.8 or more, 0.9 or more, 1 or more, 1.1 or more, 1.2 or more, 1.3 or more, 1.4 or more, 1.5 or more, 1.6 or more, or 1.7 or more. The upper limit of the relative expression level of MN1 gene to the expression level of SDHA gene is not particularly limited, and may be, for example, 10 or less, 9 or less, 8 or less, 7 or less, 6 or less, 5 or less, 4 or less, 3 or less, or 2 or less.

The cell population comprising adherent stem cells and provided by the present invention preferably satisfies the relative expression level of RARRES2 gene to the expression level of SDHA gene of 0.4 or less.

The relative expression level of RARRES2 gene to the expression level of SDHA gene may be 0.3 or less, 0.2 or less, 0.1 or less, 0.05 or less, 0.04 or less, 0.03 or less, 0.02 or less, 0.01 or less, 0.009 or less, 0.008 or less, 0.007 or less, 0.006 or less, 0.005 or less, 0.004 or less, or 0.003 or less. The lower limit of the relative expression level of RARRES2 gene to the expression level of SDHA gene is not particularly limited, and may be, for example, 0.001 or more, or 0.002 or more.

The methods for detecting individual genes and/or measuring expression levels thereof are not particularly limited as long as they are known in the art and, for example, a microarray, RT-PCR, quantitative RT-PCR or northern blot hybridization can be used. As a method for measuring the relative expression levels of individual genes to the expression level of SDHA gene, a microarray can be used. The microarray can be performed specifically by the following procedures (1) to (5). The following procedures (3) to (5) can be entrusted to and performed by RIKEN GENESIS Co., Ltd.

(1) A cryopreserved cell population is thawed and centrifugally collected. The collected cell population is washed with phosphate buffer (PBS) and the cells are centrifugally collected.

(2) Total RNA is extracted and purified by RNA extraction kit (RNeasy Plus Mini kit (manufactured by QIAGEN)).

(3) Using the purified total RNA as a template, cDNA is synthesized by reverse transcription. Then, the synthesized cDNA is further transcribed to cRNA by in vitro transcription with biotin labeling.

(4) The biotin-labeled cRNA is added to a hybridization buffer and subjected to hybridization on Human GeneGenome U133A 2.0 Array (manufactured by Affymetrix, Inc.) for 16 hours, followed by washing with GeneChip Fluidics Station 450 (manufactured by Affymetrix, Inc.), staining with phycoerythrin, scanning using GeneChip Scanner 3000 7G (manufactured by Affymetrix, Inc.), image analysis using AGCC (Affymetrix GeneChip Command Console Software, manufactured by Affymetrix, Inc.), and then quantification using Affymetrix Expression Console (manufactured by Affymetrix, Inc.).

(5) Numerical data files are compared and analyzed using the analysis software GeneSpring GX (manufactured by Agilent Technologies, Inc.). The relative expression levels of individual genes to the expression level of SDHA gene in each cell are calculated.

As the method for measuring the relative expression levels of individual genes to the expression level of SDHA gene, quantitative PCR can be used. The quantitative PCR can be carried out specifically in accordance with the following procedures (1) to (5).

(1) A cell population cryopreserved is thawed and centrifugally collected. The collected cell population is washed with phosphate buffer (PBS) and the cells are centrifugally collected.

(2) Total RNA is extracted and purified by RNA extraction kit (RNeasy Plus Mini kit (manufactured by QIAGEN)).

(3) Using the total RNA purified as a template, cDNA is synthesized by a reverse transcription reaction. The synthesized cDNA, Taqman Fast Advanced Master Mix (manufactured by Applied Biosystems) and primers (Taqman Gene Expression Assay, manufactured by Thermo Fisher) were mixed, poured in a 96-well plate and subjected to quantitative PCR.

(4) $\Delta$Ct values of individual samples to SDHA were analyzed by StepOnePlus Real-Time PCR System (manufactured by Applied Biosystems) to calculate the relative expression levels ($2^{(-\Delta Ct)}$) of the individual genes to the expression level of SDHA gene in each cell.

SDHA (Succinate dehydrogenase complex, subunit A) is a kind of housekeeping gene. The sequence of the gene is registered as ID: 6389 in the gene database of the National Center for Biotechnology Information. SDHA is a gene consisting of the nucleotide sequence represented by SEQ ID NO: 1 or a gene encoding a polypeptide consisting of the amino acid sequence represented by SEQ ID NO: 2.

The sequence of KCNAB1 (potassium channel, voltage gated subfamily A regulatory beta subunit 1) gene is registered as ID:7881 in the gene database of the National Center for Biotechnology Information. KCNAB1 is a gene consisting of the nucleotide sequence represented by SEQ ID NO: 3 or a gene encoding a polypeptide consisting of the amino acid sequence represented by SEQ ID NO: 4.

The sequence of SULT1E1 (sulfotransferase family 1E member 1) gene is registered as ID: 6783 in the gene database of the National Center for Biotechnology Information. SULT1E1 is a gene consisting of the nucleotide sequence represented by SEQ ID NO: 5 or a gene encoding a polypeptide consisting of the amino acid sequence represented by SEQ ID NO: 6.

The sequence of MN1 (meningioma (disrupted in balanced translocation) 1) gene is registered as ID:4330 in the gene database of the National Center for Biotechnology Information. MN1 is a gene consisting of the nucleotide sequence represented by SEQ ID NO: 7 or a gene encoding a polypeptide consisting of the amino acid sequence represented by SEQ ID NO: 8.

The sequence of RARRES2 (retinoic acid receptor responder (tazarotene induced) 2) gene is registered as ID: 5919 in the gene database of the National Center for Biotechnology Information. RARRES2 is a gene consisting of the nucleotide sequence represented by SEQ ID NO: 9 or a gene encoding a polypeptide consisting of the amino acid sequence represented by SEQ ID NO: 10.

The timing for measuring the above gene expression levels is not particularly limited and examples thereof include immediately after separation of cells from a biological sample, during a culture step, after purification in the culture step, immediately after n times passages (n represents an integer of 1 or more), during maintenance culture, before cryopreservation, after thawing and before formulation as a pharmaceutical composition.

In a cell population according to the present invention, the adherent stem cells can be cultured up to preferably Day 20 or later, further preferably Day 25 or later, Day 30 or later, Day 35 or later, Day 40 or later, Day 45 or later, Day 50 or later, Day 55 or later, Day 60 or later, Day 65 or later, Day 70 or later, Day 75 or later, Day 80 or later, Day 85 or later, Day 90 or later, Day 95 or later, Day 100 or later, Day 105 or later, or Day 110 or later, after the start of in vitro culture, while maintaining a normal karyotype and without terminating proliferation.

The possible number of passages of adherent stem cells in the cell population according to the present invention is 1 or more, preferably 2 or more, more preferably 3 or more, further preferably 4 or more, further preferably 5 or more, further preferably 6 or more, further preferably 8 or more, further preferably 10 or more, further preferably 12 or more, further preferably 14 or more, further preferably 16 or more, further preferably 18 or more, further preferably 20 or more, further preferably 22 or more, further preferably 24 or more, and further preferably 25 or more, wherein the passage culture can be made while maintaining a normal karyotype. The upper limit of possible number of passages is not particularly limited and is, for example, 50 or less, 45 or less, 40 or less, 35 or less, or 30 or less.

The cell population comprising adherent stem cells and provided by the present invention can be subjected to population doubling preferably 10 times or more, further preferably 20 times or more, 30 times or more, 40 times or more, 50 times or more, or 60 times or more, while maintaining a normal karyotype. The cell population comprising adherent stem cells and provided by the present invention can be subjected to population doubling; for example, 100 times or less, 90 times or less, 80 times or less or 70 times or less; but are not limited to these. The number of population doubling is a number of times of division of cell population in a certain culture period and is calculated according to an equation: [$\log_{10}$(cell number at the completion of culture)−$\log_{10}$(cell number at the start of culture)]/$\log_{10}(2)$. In a case where subculture is performed, the number of population doubling for each passage is calculated according to the equation described above and then cumulated, and thereby a total number of population doubling is calculated.

The cell viability of the cell population comprising adherent stem cells and provided by the present invention can be measured, for example, by trypan blue staining, PI(Propidium iodide) staining, or MTT (3-(4,5-Dimethyl-2-thiazolyl)-2,5-diphenyltetrazolium Bromide) assay, but is not limited to these.

The cell viability of the cell population comprising adherent stem cells and provided by the present invention is preferably 70% or more, further preferably 75% or more, 80% or more, 85% or more, 90% or more, 95% or more, 96% or more, 97% or more, 98% or more, 99% or more, or 100%.

The origin of adherent stem cells is not particularly limited, and adherent stem cells derived from, for example, a fetal appendage, bone marrow, adipose tissue or tooth pulp can be used. The adherent stem cells are preferably adherent stem cells derived from a fetal appendage, and more preferably adherent stem cells derived from the amnion. The adherent stem cells are adherent stem cells isolated from an autologous, allogeneic or heterologous biological sample, and preferably adherent stem cells isolated from an allogeneic biological sample.

The adherent stem cells are recombinant or non-recombinant adherent stem cells, and preferably non-recombinant adherent stem cells.

The cell population according to the present invention may comprise any number of adherent stem cells. The cell population according to the present invention can include, but are not limited to, not less or not more than $1.0\times10^1$ cells, $1.0\times10^2$ cells, $1.0\times10^3$ cells, $1.0\times10^4$ cells, $1.0\times10^5$ cells, $1.0\times10^6$ cells, $1.0\times10^7$ cells, $1.0\times10^8$ cells, $1.0\times10^9$ cells, $1.0\times10^{10}$ cells, $1.0\times10^{11}$ cells, $1.0\times10^{12}$ cells and $1.0\times10^{13}$ cells.

The cell population according to the present invention may comprise any components other than adherent stem cells. Examples of the components include, but are not limited to, salts (e.g., physiological saline, Ringer's solution, BICANATE infusion), polysaccharides (e.g., hydroxyethyl starch (HES) and dextran), proteins (e.g., albumin), dimethyl sulphoxide (DMSO), amino acids, and medium components (e.g., components comprised in RPMI1640 medium).

The cell population according to the present invention may be preserved in a frozen state until immediately before use. The cell population described above may comprise cryopreservation solution in addition to adherent stem cells. As the cryopreservation solution described above, a commercially available cryopreservation solution may be used. Examples thereof include, but are not limited to, CP-1 (registered trademark) (manufactured by Kyokuto Pharmaceutical Industrial Co, Ltd.), BAMBANKER (manufactured by Lymphotec Inc.), STEM-CELLBANKER (manufactured by Nippon Zenyaku Kogyo Co., Ltd.), ReproCryo RM (manufactured by REPROCELL Inc.), CryoNovo (manufactured by Akron Biotechnology, LLC.), MSC Freezing Solution (manufactured by Biological Industries Inc.), and CryoStor (manufactured by HemaCare Inc.).

The cell population according to the present invention may be provided as a composition in combination with a vehicle. As the vehicle, preferably a liquid vehicle (e.g., media, dimethyl sulfoxide (DMSO), cryopreservation solutions or pharmaceutically acceptable vehicles described below) can be used.

The composition comprising the cell population according to the present invention and the vehicle may be in any cell concentration. Exemplary cell concentrations of the composition comprising the cell population according to the present invention and a vehicle include, but are not limited to, not less or not more than $1.0\times10^1$ cells/mL, $1.0\times10^2$ cells/mL, $1.0\times10^3$ cells/mL, $1.0\times10^4$ cells/mL, $1.0\times10^5$ cells/mL, $1.0\times10^6$ cells/mL, $1.0\times10^7$ cells/mL, $1.0\times10^8$ cells/mL, $1.0\times10^9$ cells/mL, or $1.0\times10^{10}$ cells/mL.

[3] Production Method of a Cell Population Comprising Adherent Stem Cells

A production method of the cell population comprising adherent stem cells according to the present invention is a method of obtaining a cell population comprising cells collected from a living tissue or an organ such as fetal appendage and satisfying the proportion of the KCNAB1-positive adherent stem cells of 85% or more. The method for producing the cell population comprising adherent stem cells according to the present invention is also a method comprising a step of culturing a cell population comprising cells collected from a living tissue or an organ such as fetal appendage under such a condition that the proportion of KCNAB1-positive adherent stem cells is maintained at 85% or more. The condition described above serves as an index for formation of a cell population comprising adherent stem cells maintaining a normal karyotype; and the culture method according to the present invention is not particularly limited as long as the index is satisfied.

The production method according to the present invention may comprise a cell population obtainment step of obtaining a cell population comprising adherent stem cells by enzymatically treating, for example, a fetal appendage such as the amnion. Said cell population obtainment step may be a step comprising a step of obtaining the amnion by cesarean section. Further, the cell population obtainment step may comprise a step of washing a biological sample comprising adherent stem cells.

The amnion consists of an epithelial cell layer and an extracellular matrix layer, and the latter layer comprises amniotic adherent stem cells. Like other epithelial cells, the amniotic epithelial cells are characterized by expression of an epithelial adhesion factor (EpCAM: CD326). On the other hand, the amniotic adherent stem cells do not express such epithelial-specific surface antigen marker of CD326 and they can be easily distinguished by flow cytometry. The cell population obtainment step may be a step comprising a step of obtaining the amnion by cesarean section.

The cell population comprising adherent stem cells according to the present invention is preferably a cell population obtained by treating a biological sample comprising an epithelial cell layer and an adherent stem cell layer collected from a fetal appendage with at least collagenase.

The enzymatic treatment of a biological sample collected from a fetal appendage (preferably a biological sample comprising an epithelial cell layer and an adherent stem cell layer) is preferably a treatment with an enzyme (or a combination of enzymes) that can release adherent stem cells comprised in the extracellular matrix layer of the fetal appendage, and does not degrade the epithelial cell layer. Examples of such an enzyme include, but are not particularly limited to, collagenase and/or metalloproteinase. Examples of the metalloproteinase can include, but are not particularly limited to, thermolysin and/or dispase, which is metalloproteinase that cleaves nonpolar amino acids at their N-terminal sides.

The active concentration of the collagenase is preferably 50 PU/ml or higher, more preferably 100 PU/ml or higher, and further preferably 200 PU/ml or higher. The active concentration of the collagenase is, but is not particularly limited to, for example, 1000 PU/ml or lower, 900 PU/ml or lower, 800 PU/ml or lower, 700 PU/ml or lower, 600 PU/ml or lower, or 500 PU/ml or lower. In this context, PU (Protease Unit) is defined as the amount of the enzyme that degrades 1 μg of FITC-collagen in 1 minute at 30° C. and pH 7.5.

The active concentration of the metalloproteinase (e.g., thermolysin and/or dispase) is preferably 50 PU/ml or higher, more preferably 100 PU/ml or higher, and further preferably 200 PU/ml or higher. Also, the active concentration of the metalloproteinase is preferably 1000 PU/ml or lower, more preferably 900 PU/ml or lower, further preferably 800 PU/ml or lower, further preferably 700 PU/ml or lower, further preferably 600 PU/ml or lower, and further preferably 500 PU/ml or lower. In this context, PU (Protease Unit) in an aspect of using dispase as the metalloproteinase is defined as the amount of the enzyme that releases an amino acid corresponding to 1 μg tyrosine from casein lactate in 1 minute at 30° C. and pH 7.5. In the concentration range of the enzyme described above, adherent stem cells comprised in the extracellular matrix layer can be efficiently released while preventing contamination with epithelial cells comprised in the epithelial cell layer of the fetal appendage. The preferred combination of the concentrations of the collagenase and/or the metalloproteinase can be determined by the microscopic observation of the fetal appendage after the enzymatic treatment, or the flow cytometry of the obtained cells.

It is preferred to treat the fetal appendage with collagenase and metalloproteinase in combination, from the viewpoint of efficiently collecting live cells. It is further preferred to treat the fetal appendage at the same time with the above combination. In this case, thermolysin and/or dispase can be used as the metalloproteinase, though the metalloproteinase is not limited thereto. Adherent stem cells can be easily obtained by treating the fetal appendage only once with an enzyme solution comprising collagenase and metalloproteinase. The treatment at the same time can reduce the risk of contamination by bacteria, viruses, and the like.

For the enzymatic treatment of the fetal appendage, it is preferred to immerse the amnion washed using a washing solution such as physiological saline or Hank's balanced salt solution in the enzyme solution, and perform the treatment with stirring using stirring means. A stirrer or a shaker can be used as such stirring means from the viewpoint of efficiently releasing adherent stem cells comprised in the extracellular matrix layer of the fetal appendage, though the stirring means is not limited thereto. The stirring rate is not particularly limited and is, for example, 10 rpm or more, 30 rpm or more or 50 rpm or more when using a stirrer or a shaker. Also, the stirring rate is not particularly limited and is, for example, 100 rpm or less, 80 rpm or less or 60 rpm or less when using a stirrer or a shaker. The enzymatic treatment duration is not particularly limited and is, for example, 10 minutes or longer, 30 minutes or longer, 50 minutes or longer, 70 minutes or longer or 90 minutes or longer. Also, the enzymatic treatment duration is not particularly limited and is, for example, 6 hours or shorter, 4 hours or shorter, 2 hours or shorter, or 100 minutes or shorter. The enzymatic treatment temperature is not particularly limited and is, for example, 16° C. or higher, 20° C. or higher, 24° C. or higher, 28° C. or higher, 32° C. or higher or 36° C. or higher. Also, the enzymatic treatment temperature is not particularly limited and is, for example, 40° C. or lower, 39° C. or lower, or 38° C. or lower.

In the production method according to the present invention, if desired, the released adherent stem cells can be separated and/or collected from the enzyme solution comprising the released adherent stem cells by a known method such as a filter, centrifugation, a hollow fiber separation membrane, or a cell sorter. Preferably, the enzyme solution comprising the released adherent stem cells is filtered through a filter. In an aspect of filtering the enzyme solution through a filter, only the released cells pass through the filter, whereas an undegraded epithelial cell layer remains on the filter without passing through the filter. Therefore, not only can the released adherent stem cells be easily separated and/or collected, but the risk of contamination by bacteria, viruses, and the like can be reduced. Examples of the filter can include, but are not particularly limited to, mesh filters. The pore size (mesh size) of the mesh filter is not particularly limited and is, for example, 40 μm or larger, 60 μm or larger, 80 μm or larger, or 90 μm or larger. Also, the pore size of the mesh filter is not particularly limited and is, for example, 200 μm or smaller, 180 μm or smaller, 160 μm or smaller, 140 µm or smaller, 120 µm or smaller, or 100 µm or smaller. The filtration rate is not particularly limited. By using the pore size of the mesh filter within the range described above, the enzyme solution comprising the adherent stem cells can be filtered by free fall. This can prevent decrease in cell survival rate.

Nylon is preferably used as a material for the mesh filter. A tube comprising a 40 µm, 70 µm, 95 µm, or 100 µm nylon mesh filter such as a Falcon cell strainer, which is widely used for research purposes, can be used. Alternatively, medical mesh cloth (nylon and polyester) used for hemodialysis and the like can be used. Further, an arterial filter used for extracorporeal circulation (polyester mesh filter, pore size: 40 µm or larger and 120 µm or smaller) can also be used. A mesh made of any other material, for example, a stainless-steel mesh filter, may also be used.

Preferably, the adherent stem cells are allowed to pass through a filter in natural drop (free fall). It is also possible to force the cells to pass through a filter by suction using a pump or the like. In this case, minimum necessary pressurization is desirable in order to avoid damage of the cells.

The adherent stem cells that have passed through the filter can be collected by centrifugation after dilution of the filtrate with two times or more its volume of a medium or balanced salt buffer solution. Examples of the balanced salt buffer solution that can be used include, but are not limited to, physiological saline, Dulbecco's phosphate buffer (DPBS), Earle's balanced salt solution (EBSS), Hank's balanced salt solution (HBSS), and phosphate buffer (PBS).

The cell population obtained in the cell population obtainment step described above is cultured under the conditions: the proportion of KCNAB1-positive adherent stem cells in the cell population being 85% or more is maintained. The condition is useful as an index for obtaining a cell population comprising adherent stem cells maintaining a normal karyotype. The culturing method is not particularly limited as long as the index is satisfied. Examples of such a method may include: separating a cell population satisfying the above index by a cell sorter, and a method of culturing a cell population under conditions satisfying the index.

Examples of a culture method satisfying the index include, for example, a step of repeating, a plurality of times, the inoculation of the cell population into an uncoated plastic culture vessel at a density of 100 to 20,000 cells/cm$^2$ followed by culture. The lower limit of the density of the cell population for inoculation is further preferably 200 cells/cm$^2$ or more, further preferably 400 cells/cm$^2$ or more, further preferably 600 cells/cm$^2$ or more, further preferably 800 cells/cm$^2$ or more, further preferably 1000 cells/cm$^2$ or more, further preferably 1200 cells/cm$^2$ or more, further preferably 1400 cells/cm$^2$ or more, further preferably 1600 cells/cm$^2$ or more, further preferably 1800 cells/cm$^2$ or more, and further preferably 2000 cells/cm$^2$ or more. The upper limit of the density of the cell population for inoculation is further preferably 18000 cells/cm$^2$ or less, further preferably 16000 cells/cm$^2$ or less, further preferably 14000 cells/cm$^2$ or less, further preferably 12000 cells/cm$^2$ or less, further preferably 10000 cells/cm$^2$ or less, and further preferably 8000 cells/cm$^2$ or less.

Examples of the other culture methods that satisfy the index include a step of repeating a plurality of times the inoculation of the cell population into a plastic culture vessel coated with a coating agent at a density of 100 to 20,000 cells/cm$^2$ followed by culture. Preferred density conditions for the inoculation of the cell population are similar to the conditions described above.

Examples of the coating agent include, but are not limited to, extracellular matrix, fibronectin, vitronectin, osteopontin, laminin, entactin, collagen I, collagen II, collagen III, collagen IV, collagen V, collagen VI, gelatin, poly-L-ornithine, poly-D-lysine, and Matrigel (registered trademark) matrix.

The medium for use in the culture can be prepared by utilizing any liquid medium for animal cell culture as a basal medium and, if necessary, appropriately adding other components (albumin, serum, a serum replacement reagent, a growth factor, or human platelet lysate, etc.) thereto.

Examples of the basal medium that can be used include, but are not particularly limited to, media such as BME medium, BGJb medium, CMRL1066 medium, Glasgow MEM medium, improved MEM zinc option medium, IMDM medium (Iscove's modified Dulbecco's medium), Medium 199 medium, Eagle MEM medium, aMEM (alpha modification of minimum essential medium eagle) medium, DMEM medium (Dulbecco's modified Eagle's medium), Ham's F10 medium, Ham's F12 medium, RPMI 1640 medium, Fischer's medium, and mixed medium thereof (e.g., DMEM/F12 medium (Dulbecco's modified Eagle's medium/nutrient mixture F-12 Ham)).

Alternatively, the medium for use in the culture may be a commercially available serum-free medium. Examples thereof include, but are not particularly limited to, STK1 and STK2 (manufactured by DS Pharma Biomedical Co., Ltd.), EXPREP MSC Medium (manufactured by BioMimetics Sympathies Inc.), and Corning stemgro human adherent stem cell medium (manufactured by Corning Inc.).

Examples of other components to be added to the basal medium include albumin, serum, serum replacement reagents, growth factors or human platelet lysate. In an aspect of adding albumin to the basal medium, the concentration of albumin is preferably higher than 0.05% and 5% or lower. In an aspect of adding serum to the basal medium, the concentration of serum is preferably 5% or higher. In an aspect of adding a growth factor, a reagent (e.g., protein such as heparin, gel, and polysaccharide) for stabilizing the growth factor in a medium may be further added in addition to the growth factor; or the growth factor stabilized in advance may be added to the basal medium. Examples of the growth factor that can be used include, but are not particularly limited to, fibroblast growth factor (FGF), epidermal growth factor (EGF), transforming growth factor (TGF), vascular endothelial cell growth factor (VEGF), platelet-derived growth factor (PDGF), and families thereof.

Examples of further other culture methods that satisfy the index include culturing with addition of human platelet lysate (hPL) to the basal medium for use in the culture. The human platelet lysate is preferably subjected to inactivation and/or sterilization treatment for bacteria and viruses, in advance. As the above human platelet lysate, commercially available human platelet lysate may be used. Examples thereof include, but are not limited to, Stemulate (manufactured by Cook Regentec), PLTMax (manufactured by Mill Creek Life Science), UltraGRO (manufactured by AventaCell BioMedial) and PLUS (manufactured by Compass Biomedical).

The final concentration of human platelet lysate in a medium is preferably 1% or more, further preferably 2% or more, further preferably 3% or more, further preferably 4% or more and further preferably 5% or more. The final concentration of platelet lysate in a medium is preferably 20% or less, further preferably 18% or less, further preferably 16% or less, further preferably 14% or less, further preferably 12% or less, further preferably 10% or less, further preferably 9% or less, further preferably 8% or less, further preferably 7% or less and further preferably 6% or less.

Timing for adding human platelet lysate is not particularly limited and examples thereof include the beginning of a culture step, during the culture step, after purification in the culture step, immediately after n times passages (n represents an integer of 1 or more), during maintenance culture, before cryopreservation, or after thawing.

The culture of adherent stem cells can be performed by, for example, the following steps. First, a cell suspension is centrifuged; the supernatant is removed; and the obtained cell pellet is suspended in a medium. Next, the cells are inoculated into a plastic culture vessel and cultured to 95% confluence or less using a medium in an environment of a $CO_2$ concentration of 3% or higher and 5% or lower at 37° C. Examples of the medium can include, but are not limited to, αMEM, M199, and mediums using these as a base. The cells obtained by the culture as described above are cells cultured once.

Examples of the culture period of a single culture process can include 2 to 15 days and specifically 2 days, 3 days, 4 days, 5 days, 6 days, 8 days, 10 days, 12 days, 14 days and 15 days.

The cells cultured once described above can be further passaged and cultured, for example, as follows: first, the cells cultured once are treated by cell dissociation means, and thereby dissociated from the plastic culture vessel. Next, the obtained cell suspension is centrifuged, the supernatant is removed, and the obtained cell pellet is suspended in a medium. Finally, the cells are inoculated to a plastic culture vessel, and cultured to 95% or less confluence using a medium in an environment of a $CO_2$ concentration of 3% or higher, and 5% or lower at 37° C. Examples of the medium can include, but are not limited to, αMEM, M199, and media based thereon. The cells obtained by the passage and the culture as described above are cells passaged once. Cells passaged N times can be obtained by similar passage and culture (n represents an integer of 1 or more). From the viewpoint of producing the cells at a large scale, the lower limit of passage number n is, for example, 1 or more, preferably 2 or more, more preferably 4 or more, further preferably 6 or more, further preferably 8 or more, further preferably 10 or more, further preferably 12 or more, further preferably 14 or more, further preferably 16 or more, further preferably 18 or more, further preferably 20 or more, and further preferably 25 or more. In addition, from the viewpoint of suppressing cell senescence, the upper limit of passage number n is, for example, preferably 50 or less, 40 or less, or 30 or less. As the cell dissociation means, a cell dissociation agent, for example, may be used. As the cell dissociation agent, trypsin, collagenase, dispase, ethylenediaminetetraacetic acid (EDTA) or the like can be used, but the cell dissociation agent is not particularly limited. As the cell dissociation agent, a commercially available cell dissociation agent may be used. Examples thereof include, but are not limited to, trypsin-EDTA solution (manufactured by Thermo Fisher Scientific Inc.), TrypLE Select (manufactured by Thermo Fisher Scientific Inc.), Accutase (manufactured by Stemcell Technologies Inc.), and Accumax (manufactured by Stemcell Technologies Inc.). In addition, as cell dissociation means, physical cell dissociation means may be used, and examples thereof to be used include, but are not limited to, a cell scraper (manufacture by Corning Inc.). Cell dissociation means may be used alone or a plurality of cell dissociation means may be used in combination.

According to the production method in the present invention, adherent stem cells maintaining a normal karyotype can be obtained and this enables production of a safe cell preparation (a pharmaceutical composition). The lower limit of the cell number obtained per batch of culture (cell number obtained per unit surface area per unit number of culture days) differs depending on, e.g., the number of inoculated cells, the inoculation density, and is, for example, $5.0 \times 10^3$ (cells/cm$^2$/day) or more, $6.0 \times 10^3$ (cells/cm$^2$/day) or more, $8.0 \times 10^3$ (cells/cm$^2$/day) or more, $1.0 \times 10^4$ (cells/cm$^2$/day) or more, $1.1 \times 10^4$ (cells/cm$^2$/day) or more, or $1.2 \times 10^4$ (cells/cm$^2$/day) or more. Also, the upper limit of the obtained cell number per batch of culture is not particularly limited and is, for example, $1.0 \times 10^5$ (cells/cm$^2$/day) or less, $8.0 \times 10^4$ (cells/cm$^2$/day) or less, $6.0 \times 10^4$ (cells/cm$^2$/day) or less, $4.0 \times 10^4$ (cells/cm$^2$/day) or less, or $2.0 \times 10^4$ (cells/cm$^2$/day) or less.

According to the production method in the present invention, adherent stem cells maintaining a normal karyotype can be obtained. Accordingly, the adherent stem cells obtained by the production method according to the present invention can be cultured preferably up to Day 20 or later, further preferably Day 30 or later, Day 40 or later, Day 50 or later, Day 60 or later, Day 70 or later, Day 80 or later, Day 90 or later, Day 100 or later, or Day 110 or later, after the start of in vitro culture, while maintaining a normal karyotype and without terminating proliferation.

The adherent stem cells obtained by the production method according to the present invention can be cultured up to doubling number of preferably 10 or more, 20 or more, 30 or more, 40 or more, 50 or more, or 60 or more after the start of in vitro culture, while maintaining a normal karyotype and without terminating proliferation.

The production method according to the present invention may comprise an identification step of identifying a cell population comprising adherent stem cells maintaining a normal karyotype by using the proportion of KCNAB1-positive adherent stem cells being 85% or more in a cell population comprising adherent stem cells as an index.

Means for identifying the cell population comprising adherent stem cells is preferably flow cytometry, microarray, RT-PCR, and/or quantitative RT-PCR.

The timing for performing the above identification is not particularly limited, and examples thereof include immediately after separation of cells from a biological sample, during a culture step, after purification in the culture step, immediately after n times passages (n represents an integer of 1 or more), during maintenance culture, before cryopreservation, after thawing, and before formulation as a pharmaceutical composition.

The production method according to the present invention may include a step of selectively separating the identified cell population after identifying the cell population comprising adherent stem cells by using the proportion of KCNAB1-positive adherent stem cells being 85% or more as an index. Examples of the means for selectively separating the identified cell population include, but are not particularly limited to, separation of a cell population by a cell sorter, and purification of a cell population by culture.

The production method according to the present invention also may comprise a step of cryopreserving the cell population comprising adherent stem cells. In an aspect of comprising a step of cryopreserving the cell population, the cell population thawed, if necessary, may be separated, collected and/or cultured. Alternatively, the cell population thawed may be directly used.

Examples of the means for cryopreserving the cell population comprising adherent stem cells include, but are not particularly limited to, program freezers, deep freezers, and immersing in liquid nitrogen. The temperature for freezing is preferably −30° C. or lower, −40° C. or lower, −50° C. or lower, −80° C. or lower, −90° C. or lower, −100° C. or lower, −150° C. or lower, −180° C. or lower, or −196° C. (temperature of liquid nitrogen) or lower. The preferable rate of freezing is, for example, −1° C./min, −2° C./min, −5° C./min, −9° C./min, −10° C./min, −11° C./min, or −15° C./min. In the case of using a program freezer as such freezing means, the temperature can be lowered to a temperature to −50° C. or higher and −30° C. or lower (e.g., −40° C.) at a freezing rate of, for example, −2° C./min or more and −1° C./min or less, and further lowered to a temperature of −100° C. or higher and −80° C. or lower (for example, −90° C.) at a freezing rate of −11° C./min or more and −9° C./min or less (e.g., −10° C./min). When immersing in liquid nitrogen is used as a freezing means, the temperature can be rapidly lowered to, for example −196° C. for freezing, and then, cryopreservation can be carried out in liquid nitrogen (gas phase).

When freezing by the freezing means, the cell population may be frozen in a state comprised in any preservation container. Examples of such a preservation container include, but are not limited to, cryotubes, cryovials, freezing bags, and infusion bags.

When freezing by the freezing means, the cell population may be frozen in any cryopreservation solution. As the cryopreservation solution described above, a commercially available cryopreservation solution may be used. Examples of the cryopreservation solution include, but are not limited to, CP-1 (registered trademark) (manufactured by Kyokuto Pharmaceutical Industrial Co., Ltd.), BAMBANKER (manufactured by Lymphotec Inc.), STEM-CELLBANKER (manufactured by Nippon Zenyaku Kogyo Co., Ltd.), ReproCryo RM (manufactured by REPROCELL Inc.), CryoNovo (Akron Biotechnology, LLC.), MSC Freezing Solution (Biological Industries Inc.), and CryoStor (HemaCare Inc.).

The cryopreservation solution can comprise polysaccharides at a defined concentration. The preferable concentration of polysaccharides is, for example, 1% by mass or higher, 2% by mass or higher, 4% by mass or higher, or 6% by mass or higher. In addition, the preferable concentration of polysaccharides is, for example, 20% by mass or lower, 18% by mass or lower, 16% by mass or lower, 14% by mass or lower, or 13% by mass or lower. Examples of the polysaccharides include, but are not limited to, hydroxyethyl starch (HES) and dextran (e.g., Dextran40).

The cryopreservation solution can comprise dimethyl sulphoxide (DMSO) at a defined concentration. The preferable concentration of DMSO is, for example, 1% by mass or higher, 2% by mass or higher, 3% by mass or higher, 4% by mass or higher, or 5% by mass or higher. Also, the preferable concentration of DMSO is, for example, 20% by mass or lower, 18% by mass or lower, 16% by mass or lower, 14% by mass or lower, 12% by mass or lower, or 10% by mass or lower.

The cryopreservation solution may be a solution comprising albumin at a defined concentration higher than 0% by mass. The preferable concentration of albumin is, for example, 1% by mass or higher, 2% by mass or higher, 3% by mass or higher, or 4% by mass or higher. Also, the preferable concentration of albumin is, for example, 30% by mass or lower, 20% by mass or lower, 10% by mass or lower or 9% by mass or lower. Examples of albumin can include, but are not limited to, bovine serum albumin (BSA), mouse albumin, and human albumin.

The production method according to the present invention can comprise a step of washing the cell population comprising adherent stem cells. Examples of a washing solution to be used in the step of washing the cell population comprising adherent stem cells include, but are not limited to, physiological saline, Dulbecco's phosphate buffer (DPBS), Earle's balanced salt solution (EBSS), Hank's balanced salt solution (HBSS) and phosphate-buffer (PBS). Washing a cell population can reduce or remove allergen, endotoxin or the like. Examples of the allergen include, but are not limited to, bovine serum albumin (BSA), swine trypsin and swine heparin.

The production method according to the present invention can comprise, if desired, a step of removing undesirable cell aggregates from the cell population comprising adherent stem cells. The step of removing undesirable cell aggregates from the cell population comprising adherent stem cells may be a step comprising a step of filtering a cell population comprising adherent stem cells (cell suspension) by a filter.

The production method according to the present invention can comprise a step of filling the cell population comprising adherent stem cells into a preservation container. Examples of such a preservation container include, but are not limited to, cryotubes, cryovials, freezing bags, and infusion bags.

[4] Method for Monitoring Karyotypic Abnormality of Adherent Stem Cells, Method for Evaluating a Donor and/or a Biological Sample Collected from the Donor, and Method for Determining and/or Predicting an Optimal Enzymatic Treatment Condition In the present invention, in a cell population comprising adherent stem cells, the karyotypic abnormality of adherent stem cells can be monitored by performing measurement (preferably by performing measurement over time) by using the proportion of KCNAB1-positive adherent stem cells being 85% or more. Examples of the step that requires monitoring include a culture step, a cryopreservation step and/or a formulation step.

In the culture step, for example, measurement of the index over time allows changes in karyotypic abnormality of adherent stem cells to be quickly and easily known and predicted. It can be known that in a cell population comprising adherent stem cells satisfying the index, the adherent stem cells maintain a normal karyotype. On the other hand, when a culture state continues with a value deviating from the index, it can be predicted that the karyotypic abnormality of adherent stem cells is increasing. When it is read out from the index that the karyotypic abnormality of adherent stem cells is increasing, expression of the karyotypic abnormality of adherent stem cells can be suppressed by properly changing culture conditions (change of an inoculation density, a medium, a growth factor, serum, etc.) as needed. When the index is not satisfied, only a cell population comprising adherent stem cells that satisfy the index is separated by use of, for example, a cell sorting technique. The adherent stem cells in the cell population are inoculated again and subcultured, and thereby expression of the karyotypic abnormality of adherent stem cells can be suppressed. At the early stage of culture, culture conditions (change of an inoculation density, a medium, a growth factor, serum, etc.) may be designed such that the index is satisfied at the final stage of the step, and thus, the index may be satisfied at least at the final stage.

In the present invention, the quality of a donor itself and/or a biological sample collected from the donor can be evaluated by obtaining a cell population comprising adherent stem cells from the donor, measuring the proportion of KCNAB1-positive adherent stem cells in the cell population and performing evaluation based on the proportion of KCNAB1-positive adherent stem cells in the cell population being 85% or more as an index. When a cell population comprising adherent stem cells that satisfy the index is obtained (preferably, easily obtained), the quality of the donor and/or a biological sample collected from the donor can be confirmed to be good. On the other hand, the case where the proportion in the cell population comprising adherent stem cells deviates from the index means that the quality of a biological sample collected from the donor is bad. In this case, occurrence of the karyotypic abnormality of adherent stem cells can be suppressed by properly changing culture conditions (change of an inoculation density, a medium, a growth factor, serum, etc.). When the proportion in the cell population comprising adherent stem cells deviates from the index, the karyotypic abnormality of adherent stem cells can be reduced by separating a cell population comprising adherent stem cells satisfying the index by use of, for example, a cell sorting technique, and inoculating and culturing the adherent stem cells in the cell population. Alternatively, a risk of obtaining bad-quality adherent stem cells in a large amount can be reduced by discarding a biological sample deviating from the index without subjecting to culture. At the early stage of culture, culture conditions (change of an inoculation density, a medium, a growth factor, serum, etc.) may be designed such that the index is satisfied at the final stage of the step, and thus, the index may be satisfied at least at the final stage. Note that, in confirming the quality of a biological sample collected from a donor, a method for preparing and treating a biological sample, and a method for culturing a cell population are not particularly limited, and any methods can be employed.

In the present invention, in regard to a cell population obtained by enzymatically treating a biological sample collected from a donor, an optimal enzymatic treatment condition can be determined and/or predicted by measuring the proportion of KCNAB1-positive adherent stem cells in the cell population and performing evaluation based on the proportion of KCNAB1-positive adherent stem cells in the cell population being 85% or more as an index. When a cell population comprising adherent stem cells that satisfies the index is obtained (preferably, easily obtained), the enzymatic treatment method can be determined and/or predicted to be appropriate for the biological sample collected from a donor. On the other hand, when a culture state continues with a value deviating from the index, the enzymatic treatment method can be determined and/or predicted to be inappropriate for the biological sample collected from a donor. Note that, in determining and/or predicting an optimal enzymatic treatment method, a method for preparing and treating the biological sample, and a method for culturing a cell population are not particularly limited, and any methods can be employed.

The index can be measured at a necessary timing. Examples of the timing include, but are not particularly limited to, immediately after separation of cells from a biological sample, during a culture step, after purification in the culture step, immediately after n times passages (n represents an integer of 1 or more), during maintenance culture, before cryopreservation, after thawing, or before formulation as a pharmaceutical composition.

[5] Pharmaceutical Composition

The cell population comprising adherent stem cells according to the present invention can be used as a pharmaceutical composition. That is, the present invention provides a pharmaceutical composition comprising the cell population comprising adherent stem cells according to the present invention and a pharmaceutically acceptable vehicle. According to the present invention, a pharmaceutical composition comprising a cell population comprising adherent stem cells according to the present invention and additional cells that can be administered is further provided.

The pharmaceutical composition according to the present invention can be used as a cell therapy agent, for example, a therapeutic agent for intractable diseases.

The pharmaceutical composition according to the present invention can be used as a therapeutic agent for a disease selected from immune-related disease, ischemic disease, lower-limb ischemia, cerebrovascular ischemia, renal ischemia, pulmonary ischemia, neurological disease, graft-versus-host disease, inflammatory bowel disease, Crohn's disease, ulcerative colitis, radiation enteritis, systemic lupus erythematosus, lupus erythematosus, collagen disease, stroke, cerebral infarction, intracerebral hematoma, cerebrovascular paralysis, liver cirrhosis, atopic dermatitis, multiple sclerosis, psoriasis, epidermolysis bullosa, diabetes mellitus, mycosis fungoides, scleroderma, disease caused by the degeneration and/or inflammation of connective tissues such as cartilage, articular cartilage defect, meniscal damage, osteochondritis dissecans, aseptic necrosis, knee osteoarthritis, inflammatory arthritis, rheumatoid arthritis, eye disease, angiogenesis-related disease, ischemic heart disease, coronary heart disease, myocardial infarction, angina pectoris, cardiac failure, cardiomyopathy, valvular disease, wound, epithelial damage, fibrosis, lung disease and cancer. The above diseases can be treated by administering the pharmaceutical composition according to the present invention to a treatment site in an amount whereby an effect can be measured.

The present invention provides the cell population comprising adherent stem cells according to the present invention for use in a pharmaceutical composition.

The present invention provides the cell population comprising adherent stem cells according to the present invention for use in a cell therapy agent.

The present invention provides a cell population comprising adherent stem cells according to the present invention for use in treating a disease selected from immune-related disease, ischemic disease, lower-limb ischemia, cerebrovascular ischemia, renal ischemia, pulmonary ischemia, neurological disease, graft-versus-host disease, inflammatory bowel disease, Crohn's disease, ulcerative colitis, radiation enteritis, systemic lupus erythematosus, lupus erythematosus, collagen disease, stroke, cerebral infarction, intracerebral hematoma, cerebrovascular paralysis, liver cirrhosis, atopic dermatitis, multiple sclerosis, psoriasis, epidermolysis bullosa, diabetes mellitus, mycosis fungoides, scleroderma, disease caused by the degeneration and/or inflammation of connective tissues such as cartilage, articular cartilage defect, meniscal damage, osteochondritis dissecans, aseptic necrosis, knee osteoarthritis, inflammatory arthritis, rheumatoid arthritis, eye disease, angiogenesis-related disease, ischemic heart disease, coronary heart disease, myocardial infarction, angina pectoris, cardiac failure, cardiomyopathy, valvular disease, wound, epithelial damage, fibrosis, lung disease and cancer.

The present invention provides a cell population comprising adherent stem cells according to the present invention for use in regeneration of myocardium, producing of cardiomyocytes, angiogenesis, repair of blood vessels, or suppression of immune response by administering it to a patient or a subject.

The present invention provides a method for transplanting cells to a patient or a subject and a method for treating a disease of a patient or a subject, comprising a step of administering a therapeutically effective amount of the cell population comprising adherent stem cells according to the present invention to the patient or the subject.

The present invention provides use of the cell population comprising adherent stem cells according to the present invention for the manufacture of a pharmaceutical composition.

The present invention provides use of the cell population comprising adherent stem cells according to the present invention for the manufacture of a cell therapy agent.

The present invention provides use of a cell population comprising adherent stem cells according to the present invention for producing a therapeutic agent for a disease selected from immune-related disease, ischemic disease, lower-limb ischemia, cerebrovascular ischemia, renal ischemia, pulmonary ischemia, neurological disease, graft-versus-host disease, inflammatory bowel disease, Crohn's disease, ulcerative colitis, radiation enteritis, systemic lupus erythematosus, lupus erythematosus, collagen disease, stroke, cerebral infarction, intracerebral hematoma, cerebrovascular paralysis, liver cirrhosis, atopic dermatitis, multiple sclerosis, psoriasis, epidermolysis bullosa, diabetes mellitus, mycosis fungoides, scleroderma, disease caused by the degeneration and/or inflammation of connective tissues such as cartilage, articular cartilage defect, meniscal damage, osteochondritis dissecans, aseptic necrosis, knee osteoarthritis, inflammatory arthritis, rheumatoid arthritis, eye disease, angiogenesis-related disease, ischemic heart disease, coronary heart disease, myocardial infarction, angina pectoris, cardiac failure, cardiomyopathy, valvular disease, wound, epithelial damage, fibrosis, lung disease and cancer.

The present invention provides use of a cell population comprising adherent stem cells according to the present invention for producing a therapeutic agent required for suppressing regeneration of myocardium, producing of cardiomyocytes, angiogenesis, repair of blood vessels, or suppression of immune response by administering it to a patient or a subject.

The pharmaceutical composition according to the present invention may be obtained by diluting a cell population comprising adherent stem cells with a pharmaceutically acceptable vehicle. The pharmaceutically acceptable vehicle is not particularly limited as long as it is a solution that can be administered to a patient or a subject. The pharmaceutically acceptable vehicle may be an infusion preparation, and examples thereof include, but are not limited to, water for injection, physiological saline, 5% glucose solution, Ringer's solution, lactated Ringer's solution, acetated Ringer's solution, bicarbonated Ringer's solution, amino acid solution, starter solution (Solution I), rehydration solution (Solution II), maintenance infusion (Solution III), postoperative recovery solution (Solution IV), and Plasma-Lyte A (registered trademark).

The "patient or subject" used herein is typically a human and may be other animals. Examples of other animals include, but are not limited to, mammals such as dogs, cats, cattle, horses, pigs, goats, sheep, monkeys (cynomolgus monkey, rhesus monkey, common marmoset and Japanese monkey), ferrets, rabbits and rodents (mouse, rat, Mongolian gerbil, guinea pig and hamster); birds such as chickens and quails.

The term "therapy" used herein refers to significantly improving at least one of, for example, life prognosis, functional prognosis, viability, weight loss, anemia, diarrhea, melena, pain in the abdomen, fever, reduction in appetite, malnutrition, vomiting, fatigue, rash, inflammation, ulcer, erosion, fistula, constriction, ileus, internal bleeding, rectal bleeding, convulsions, pain, hypohepatia, cardiac hypofunction, pulmonary hypofunction and blood test items of a patient or a subject, but examples are not limited to these.

The pharmaceutical composition according to the present invention may comprise any component for use in the treatment of a patient or a subject. Examples of the component include, but are not limited to, salts (e.g., physiological saline, Ringer's solution, BICANATE infusion), polysaccharides (e.g., hydroxyethyl starch (HES) and dextran), proteins (e.g., albumin), dimethyl sulphoxide (DMSO), amino acids, and medium components (e.g., components comprised in RPMI1640 medium).

The pharmaceutical composition according to the present invention may comprise various additives for increasing the preservation stability, the isotonicity, the absorbability, and/or the viscosity, such as an emulsifier, a dispersant, a buffer, a preservative, a wetting agent, an antioxidant, a chelating agent, a thickener, a gelling agent and a pH adjuster. Examples of the thickener include, but are not limited to, HES, dextran, methylcellulose, xanthan gum, carboxymethylcellulose and hydroxypropyl methylcellulose. The concentration of the thickener can be optionally set according to the selected thickener, within the range of concentration that is safe when administered to the patient or the subject and achieves the desired viscosity.

The pharmaceutical composition according to the present invention may comprise one or more additional medicines besides the adherent stem cells. Examples of the additional medicines include, but are not limited to, antibiotics, albumin preparations, vitamin preparations and anti-inflammatory agents. Examples of the anti-inflammatory agents include, but are not limited to, 5-aminosalicylic acid preparations, steroid preparations, immunosuppressants and biological preparations. Examples of the 5-aminosalicylic acid preparations include, but are not limited to, salazosulfapyridine and mesalazine. Examples of the steroid preparations include, but are not limited to, cortisone, prednisolone and methylprednisolone. Examples of the immunosuppressants include, but are not limited to, tacrolimus, cyclosporine, methotrexate, azathioprine and 6-mercaptopurine. Examples of the biological preparations include, but are not limited to, infliximab, adalimumab, ustekinumab, secukinumab, ixekizumab, brodalumab, tocilizumab, vedolizumab, filgotinib, golimumab, certolizumab pegol, abatacept and etanercept.

The additional medicines may be additional cells that can be administered. Examples of the additional cells that can be administered include, but are not limited to, blood-derived cells (e.g., white blood cells, red blood cells, mononuclear cells), vascular endothelial cells, endothelial precursor cells, pericytes, vascular wall cells, fibroblasts, skeletal myoblasts, epithelial cells, stromal cells, and mature adipose cells.

The pH of the pharmaceutical composition according to the present invention can be around neutral pH, for example, pH5.5 or more, 6.5 or more or pH7.0 or more and also pH10.5 or less, pH9.5 or less, pH8.5 or less or pH8.0 or less; however, the pH is not limited to these.

The cell concentration of the pharmaceutical composition according to the present invention is the concentration of cells that allows a patient or a subject to whom the pharmaceutical composition has been administered to obtain therapeutic effects on diseases, compared with a patient or a subject to whom the pharmaceutical composition has not been administered. The specific cell concentration can be appropriately determined depending on the form of administration, the administration method, the intended use, the age, body weight, symptoms of a patient or a subject, and the like. The lower limit of cell concentration of the pharmaceutical composition according to the present invention is not particularly limited, and is, for example, $1.0\times10^5$ cells/mL or more, $1.0\times10^6$ cells/mL or more, $1.2\times10^6$ cells/mL or more, $1.4\times10^6$ cells/mL or more, $1.6\times10^6$ cells/mL or more, $1.8\times10^6$ cells/mL or more, $2.0\times10^6$ cells/mL or more, $3.0\times10^6$ cells/mL or more, $4.0\times10^6$ cells/mL or more, $5.0\times10^6$ cells/mL or more, $6.0\times10^6$ cells/mL or more, $7.0\times10^6$ cells/mL or more, $8.0\times10^6$ cells/mL or more, $9.0\times10^6$ cells/mL or more, $9.5\times10^6$ cells/mL or more, or $1.0\times10^7$ cells/mL or more. The upper limit of cell concentration of the pharmaceutical composition according to the present invention is not particularly limited, and is, for example, $1.0\times10^{10}$ cells/mL or less, $1.0\times10^9$ cells/mL or less, $8.0\times10^8$ cells/mL or less, $6.0\times10^8$ cells/mL or less, $4.0\times10^8$ cells/mL or less, $2.0\times10^8$ cells/mL or less, or $1.0\times10^8$ cells/mL or less.

The pharmaceutical composition according to the present invention is preferably a liquid preparation, and more preferably an injectable liquid preparation. As the injectable liquid preparation, liquid preparations suitable for injection are known in, for example, International Publication No. WO 2011/043136 and JP Patent Publication (Kokai) No. 2013-256510. The pharmaceutical composition according to the present invention may also be an injectable liquid preparation described in the above literatures.

The above liquid preparation may be a cell suspension or a liquid preparation having cells dispersed in liquid. Further, the form of cells comprised in the liquid preparation is not particularly limited, and, for example, may be single cells or cell aggregates.

If the pharmaceutical composition according to the present invention is an injectable liquid preparation, the lower limit of cell concentration of the injectable liquid preparation, from the viewpoint of enhancing therapeutic effect on a disease, is preferably $1.0\times10^6$ cells/mL or more, $1.2\times10^6$ cells/mL or more, $1.4\times10^6$ cells/mL or more, $1.6\times10^6$ cells/mL or more, $1.8\times10^6$ cells/mL or more, $2.0\times10^6$ cells/mL or more, $3.0\times10^6$ cells/mL or more, $4.0\times10^6$ cells/mL or more, $5.0\times10^6$ cells/mL or more, $6.0\times10^6$ cells/mL or more, $7.0\times10^6$ cells/mL or more, $8.0\times10^6$ cells/mL or more, $9.0\times10^6$ cells/mL or more, $9.5\times10^6$ cells/mL or more, or $1.0\times10^7$ cells/mL or more. In contrast, the upper limit of cell concentration of the injectable liquid preparation, from the viewpoint of simplifying preparation and administration of the injectable liquid preparation, is preferably $1.0\times10^9$ cells/mL or less, $8.0\times10^8$ cells/mL or less, $6.0\times10^8$ cells/mL or less, $4.0\times10^8$ cells/mL or less, $2.0\times10^8$ cells/mL or less, or $1.0\times10^8$ cells/mL or less.

According to one aspect of the present invention, the pharmaceutical composition according to the present invention may be a transplant preparation. The transplant preparation is a solid-state or gel-like preparation. As the solid-state transplant preparation, for example, a transplant preparation of a sheet-like structure or a pellet-like structure is mentioned. As the gel-like transplant preparation, a transplant preparation comprising gel, which is obtained by bonding discrete cells with an adhesive (for example, fibrinogen) is known in, for example, International Publication No. WO 2017/126549. Also, according to an aspect according to the present invention, the pharmaceutical composition according to the present invention may be a gel preparation prepared by mixing cells and a gel. As the gel preparation, for example, a cell therapy agent constituted of an adherent stem cells and a hydrogel composition is known in JP Patent Publication (Kohyo) No. 2017-529362. The pharmaceutical composition according to the present invention can be formed into a gel preparation by employing a method described in the above literatures.

As the sheet-like transplant preparation, a cell sheet obtained by culturing in a temperature-responsive culture dish (for example, UpCell (registered trademark) (manufactured by CellSeed Inc.)), a laminate of a sheet-like cell culture and fibrin gel, and a cell-coated sheet obtained by applying a cell suspension to a sheet-like substrate, are known in, for example, International Publication No. WO 2006/080434 and JP Patent Publication (Kokai) No. 2016-52272. The pharmaceutical composition according to the present invention may be used for preparing various transplant preparations of a sheet-like structure by employing a method described, for example, in the above literatures.

Examples of the administration method of the pharmaceutical composition according to the present invention include, but are not particularly limited to, subcutaneous injection, intradermal injection, intramuscular injection, intra-lymph nodal injection, intravenous injection, intra-arterial injection, intraperitoneal injection, intrathoracic injection, direct localized injection, direct patch and direct localized transplantation. According to an aspect of the present invention, an injectable liquid preparation can be filled in a syringe and administered through a needle or a catheter into the vein, artery, myocardium, internodal space, hepatic artery, muscle, epidural site, gum, ventricle, subcutaneous site, intradermal site, intraperitoneal site and portal vein; however, injection sites are not limited to these. Regarding the administration method of the pharmaceutical composition according to the present invention, intravenous injection, intravenous drip injection, local direct injection, local direct transplantation and others are known in, for example, JP Patent Publication (Kokai) No. 2015-61520, Onken J E, et al., American College of Gastroenterology Conference 2006 Las Vegas, NV, Abstract 121, and Garcia-Olmo D, et al., Dis Colon Rectum 2005; 48: 1416-23. The pharmaceutical composition according to the present invention can also be administered by various methods described in the above literatures.

The dose of the pharmaceutical composition according to the present invention is the amount of cells that allows a patient or a subject to whom the pharmaceutical composition has been administered to obtain therapeutic effects on diseases, compared with a patient or a subject to whom the pharmaceutical composition has not been administered. A specific dose can be appropriately determined depending on the form of administration, the administration method, the intended use, the age, body weight, symptoms of a patient or a subject, and the like. A single dose of adherent stem cells to a human is not particularly limited and is, for example, $1\times10^4$ cells/kg body weight or more, $1\times10^5$ cells/kg body weight or more, $5\times10^5$ cells/kg body weight or more, $1\times10^6$ cells/kg body weight or more, $2\times10^6$ cells/kg body weight or more, $4\times10^6$ cells/kg body weight or more, $6\times10^6$ cells/kg body weight or more, or $8\times10^6$ cells/kg body weight or more. A single dose of adherent stem cells to a human is not particularly limited and is, for example, $1\times10^{12}$ cells/kg body weight or less, $1\times10^{11}$ cells/kg body weight or less, $1\times10^{10}$ cells/kg body weight or less, $1\times10^9$ cells/kg body weight or less, $5\times10^8$ cells/kg body weight or less, $1\times10^8$ cells/kg body weight or less, $8\times10^7$ cells/kg body weight or less, $6\times10^7$ cells/kg body weight or less, $4\times10^7$ cells/kg body weight or less, or $2\times10^7$ cells/kg body weight or less.

When the pharmaceutical composition according to the present invention is an injectable liquid preparation, a single dose of adherent stem cells of the injectable liquid preparation to a human, from the viewpoint of enhancing therapeutic effect on a disease, is preferably, $1\times10^5$ cells/kg body weight or more, $5\times10^5$ cells/kg body weight or more, $1\times10^6$ cells/kg body weight or more, $2\times10^6$ cells/kg body weight or more, $4\times10^6$ cells/kg body weight or more, $6\times10^6$ cells/kg body weight or more, or $8\times10^6$ cells/kg body weight or more. Also, a single dose of adherent stem cells of the injectable liquid preparation to a human, from the viewpoint of simplifying preparation and administration of an injectable liquid preparation, is preferably, $1\times10^9$ cells/kg body weight or less, $5\times10^8$ cells/kg body weight or less, $1\times10^8$ cells/kg body weight or less, $8\times10^7$ cells/kg body weight or less, $6\times10^7$ cells/kg body weight or less, $4\times10^7$ cells/kg body weight or less, or $2\times10^7$ cells/kg body weight or less.

The frequency of administration of the pharmaceutical composition according to the present invention is the frequency that allows a patient or a subject to whom the pharmaceutical composition has been administered to obtain therapeutic effects on diseases. A specific frequency of administration can be appropriately determined depending on the form of administration, the administration method, the intended use, the age, body weight, symptoms of a patient or a subject, and the like, and is, for example, once every 4 weeks, every 3 weeks, every two weeks, every week, twice per week, three times per week, four times per week, five times per week, six times per week, or seven times per week.

The administration period of the pharmaceutical composition according to the present invention is the period that allows a patient or a subject to whom the pharmaceutical composition has been administered to obtain therapeutic effects on diseases. Specific administration period can be appropriately determined depending on the form of administration, the administration method, the intended use, the age, body weight, symptoms of a patient or a subject, and the like, and is, for example, a week, 2 weeks, 3 weeks, 4 weeks, 5 weeks, 6 weeks, 7 weeks, or 8 weeks.

The timing for administering the pharmaceutical composition according to the present invention to a patient or a subject is not particularly limited, and examples thereof include immediately after onset of a disease, within n days (n represents an integer of 1 or more) from onset, immediately after diagnosis, within n days (n represents an integer of 1 or more) from diagnosis, before remission, during remission, after remission, before relapse, during relapse and after relapse.

The pharmaceutical composition according to the present invention can be preserved in a frozen state until immediately before use. The temperature for cryopreservation is preferably −30° C. or lower, −40° C. or lower, −50° C. or lower, −80° C. or lower, −90° C. or lower, −100° C. or lower, −150° C. or lower, −180° C. or lower or −196° C. (liquid nitrogen temperature) or lower. When the pharmaceutical composition according to the present invention is administered to a patient or a subject, it can be used after being quickly thawed at 37° C.

Other examples of diseases that can be treated by use of a cell population comprising adherent stem cells in a patient or a subject and still other specific examples of the diseases and specific procedures for treatment can be referred to the descriptions of, e.g., Hare et al., J. Am. Coll. Cardiol., 2009 Dec. 8; 54 (24): 2277-2286, Honmou et al., Brain 2011: 134; 1790-1807, Makhoul et al., Ann. Thorac. Surg. 2013; 95: 1827-1833, JP Patent No. 590577, JP Patent Publication (Kokai) No. 2010-518096, JP Patent Publication (Kohyo) No. 2012-509087, JP Patent Publication (Kohyo) No. 2014-501249, JP Patent Publication (Kokai) No. 2013-256515, JP Patent Publication (Kokai) No. 2014-185173, JP Patent Publication (Kohyo) No. 2010-535715, JP Patent Publication (Kokai) No. 2015-038059, JP Patent Publication (Kokai) No. 2015-110659, JP Patent Publication (Kohyo) No. 2006-521121, JP Patent Publication (Kohyo) No. 2009-542727, JP Patent Publication (Kokai) No. 2014-224117, JP Patent Publication (Kokai) No. 2015-061862, JP Patent Publication (Kohyo) No. 2002-511094, JP Patent Publication (Kohyo) No. 2004-507454, JP Patent Publication (Kohyo) No. 2010-505764, JP Patent Publication (Kohyo) No. 2011-514901, JP Patent Publication (Kokai) No. 2013-064003, JP Patent Publication (Kokai) No. 2015-131795.

The present invention will be specifically explained with reference to the Examples below; however, the present invention is not limited to the Examples.

EXAMPLES

Comparative Example 1

In the following Comparative Example 1 and Example 1, the index for obtaining a cell population comprising adherent stem cells exhibiting high karyotype stability was investigated.

Step 1-1: Collection of Amnion

A fetal membrane and a placenta, which are fetal appendages, were aseptically collected from a pregnant woman of an elective cesarean section case after obtaining informed consent. The obtained fetal membrane and placenta were comprised in a sterile tray comprising physiological saline. An amnion was manually separated from the stump of the fetal membrane. The amnion was washed with a Hank's balanced salt solution (free of Ca and Mg) to remove attached blood and clots.

Step 1-2: Enzymatic Treatment of Amnion and Collection of Amniotic Adherent Stem Cells The amnion comprising the epithelial cell layer and adherent stem cell layer was immersed in a Hank's balanced salt solution (comprising Ca and Mg) comprising 240 PU/mL collagenase and 200 PU/mL dispase I and stirred while shaking at 37° C., for 90 minutes and at 50 rpm to enzymatically treat the amnion. The solution after enzymatic treatment was filtered through a nylon mesh having openings of 95 μm to remove undigested products of the amnion so as to collect a cell suspension comprising amniotic adherent stem cells.

Step 1-3: Culture of Amniotic Adherent Stem Cells

The cell population comprising amniotic adherent stem cells and obtained in the above section "Enzymatic treatment of amnion and collection of amniotic adherent stem cells" was inoculated into a culture vessel, CellSTACK (registered trademark) (manufactured by Corning Incorporated) at a density of 6,000 cells/cm² and adherent cultured in αMEM (Alpha Modification of Minimum Essential Medium Eagle) comprising 10% (final concentration) fetal bovine serum (FBS) and 10 ng/mL (final concentration)

basic fibroblast growth factor (bFGF), until subconfluence. Thereafter, the zero-th passage cells were dissociated by using TrypLE Select. A ⅕ amount of the cells was inoculated in the CellSTACK (registered trademark) at the same scale as that of the previous culture, and subcultured. Medium replacement was carried out at a frequency of once every 2 to 4 days. The first-passage cells that reached subconfluence were dissociated by using TrypLE Select and RPMI1640 was added so as to obtain a cell concentration of $2 \times 10^7$ cells/mL. To this, the same amount of a CP-1 (registered trademark) solution, which is a solution comprising CP-1 (registered trademark) and 25% human serum albumin in a ratio of 34:16, was added, transferred to cryovials in an amount of 1 mL per vial, gradually frozen up to −80° C. and then cryopreserved a day in liquid nitrogen. Thereafter, the second-passage cells were thawed and inoculated at a density of about 15,000 to 18,000 cells/cm² in CellSTACK (registered trademark) and adherent cultured in αMEM (Alpha Modification of Minimum Essential Medium Eagle) comprising 10% (final concentration) fetal bovine serum (FBS) and 10 ng/mL (final concentration) basic fibroblast growth factor (bFGF), until subconfluence. Thereafter, the second-passage cells were dissociated by using TrypLE Select. A ⅕ amount of the cells was inoculated in the CellSTACK (registered trademark) at the same scale as that of the previous culture and subcultured. Medium replacement was carried out at a frequency of once every 2 to 4 days. The third-passage cells that reached subconfluence were dissociated by using TrypLE Select and RPMI1640 was added so as to obtain a cell concentration of $4 \times 10^6$ cells/mL. To this, the same amount of a CP-1 (registered trademark) solution, which is a solution comprising CP-1 (registered trademark) and 25% human serum albumin in a ratio of 34:16, was added, transferred to cryovials in an amount of 1 mL per vial, gradually frozen up to −80° C. and then cryopreserved a day in liquid nitrogen. Thereafter, the fourth-passage cells were thawed and inoculated at a density of about 6,000 cells/cm² in CellSTACK (registered trademark) and adherent cultured in αMEM (Alpha Modification of Minimum Essential Medium Eagle) comprising 10% (final concentration) fetal bovine serum (FBS) and 10 ng/mL (final concentration) basic fibroblast growth factor (bFGF), until subconfluence. Thereafter, the fourth-passage cells were dissociated by using TrypLE Select. A ⅕ amount of the cells was inoculated in the CellSTACK (registered trademark) at the same scale as that of the previous culture and subcultured. Medium replacement was carried out at a frequency of once every 2 to 4 days. The fifth-passage cells that reached subconfluence were dissociated by using TrypLE Select and RPMI1640 was added so as to obtain a cell concentration of $4 \times 10^6$ cells/mL. To this, the same amount of a CP-1 (registered trademark) solution, which is a solution comprising CP-1 (registered trademark) and 25% human serum albumin in a ratio of 34:16, was added, transferred to cryovials in an amount of 1 mL per vial, gradually frozen up to −80° C. and cryopreserved in liquid nitrogen.

Step 1-4: Analysis for Antigen of Amniotic Adherent Stem Cells

With respect to the fifth-passage amniotic adherent stem cells cultured by the above culture method, individual surface antigens known as an MSC marker (CD73 positive rate, CD90 positive rate, CD105 positive rate, CD166 positive rate, CD45 negative rate, CD34 negative rate, CD326 negative rate) were analyzed by a flow cytometer. As a result, the CD73, CD90 and CD105 positive rates were all 90% or more (specifically, CD73: 100%, CD90: 97%, CD105: 100%); and the CD166 positive rates were all 30% or more (specifically, CD166: 98%). CD45, CD34 and CD326 negative rates were all 95% or more (specifically, CD45: 100%, CD34: 100%, CD326: 100%). From the results, it was confirmed that the cells cultured by the above culture method are adherent stem cells.

Amniotic adherent stem cells of the third- and fifth-passage cultured by the above culture method were fixed, passed through a membrane and subjected to analysis by a flow cytometer to obtain the proportion of KCNAB1 antigen-positive cells. The proportion of the cells in either one of the passages was less than 85% (the third passage: 78%, the fifth passage: 81%).

Note that, in this measurement, FITC Mouse IgG1, κ Isotype Control (BD/model number: 550616) and PE Mouse IgG1, κ Isotype Control (BD/model number: 555749) were used as an isotype control antibody; FITC Mouse Anti-Human CD73 (BD/model number: 561254) as an antibody for CD73 antigen; FITC Mouse Anti-Human CD90 (BD/model number: 555595) as an antibody for CD90 antigen; Anti-Human Antibodies FITC Conjugate (BioLegend company/model number: 323203) as an antibody for CD105 antigen; PE Mouse Anti-Human CD166(BD/model number: 559263) as an antibody for CD166 antigen; FITC Mouse Anti-Human CD45 (BD/model number: 555482) as an antibody for CD45 antigen; PE Mouse Anti-Human CD34 (BD/model number: 555822) as an antibody for CD34 antigen; FITC Mouse Anti-Human EpCAM (BD/model number: 347197) as an antibody to CD326 antigen; and Kcnab1 monoclonal antibody (FITC) (Abnova/model number: MAB11866) as an antibody for KCNAB1 antigen. The surface antigen analysis and antigen analysis were carried out by use of BD Accuri™ C6 Flow Cytometer of Becton, Dickinson and Company (BD) in the conditions: analysis cell number: 5,000 cells and flow rate setting: Slow (14 μL/min). The proportion of cells positive for each antigen was calculated by the following procedures.

(1) Measurement results were plotted as dots with side scattered light (SSC) on the vertical axis and FSC (forward-scattered light) on the horizontal axis.

(2) In the dot plot diagram, all regions (gates) in which the cell population with stronger fluorescence intensity is 0.5% or less from all cells measured with the isotype control antibodies were selected.

(3) The proportion of cells comprised in the gate selected in (2) from all cells measured with the antibody against the antigen marker was calculated.

Step 1-5: Gene Expression Analysis of Amniotic Adherent Stem Cells

With respect to the fifth-passage amniotic adherent stem cells cultured in the above culture method, expression analysis of genes (KCNAB1 gene, SULT1E1 gene, MN1 gene, RARRES2 gene) by a microarray was entrusted to and performed by RIKEN GENESIS Co., Ltd.

The microarray analysis was carried out in accordance with the following procedures (1) to (4). Note that, the procedures of (2) to (4) were carried out by RIKEN GENESIS Co., Ltd.

(1) A cryopreserved cell population was thawed and centrifugally collected. The collected cell population was washed with phosphate buffer (PBS) and centrifugally collected. Thereafter, total RNA was extracted and purified by RNeasy Plus Mini kit (manufactured by QIAGEN).

(2) cDNA was synthesized by a reverse transcription from 100 ng of total RNA. Then, cDNA was transcribed into cRNA by in vitro transcription with biotin labeling (using 3' IVT PLUS Reagent Kit).

(3) The labeled cRNA (10.0 μg) was added to a hybridization buffer and subjected to hybridization on Human GeneGenome U133A 2.0 Array (manufactured by Affymetrix, Inc.) for 16 hours, followed by washing with GeneChip Fluidics Station 450 (manufactured by Affymetrix, Inc.), staining with phycoerythrin, scanning using GeneChip Scanner 3000 7G (manufactured by Affymetrix, Inc.), image analysis using AGCC (Affymetrix GeneChip Command Console Software) (manufactured by Affymetrix, Inc.), and then quantification using Affymetrix Expression Console (manufactured by Affymetrix, Inc.).

(4) Numerical data files were analyzed using the analysis software GeneSpring GX (manufactured by Agilent Technologies, Inc.).

The expression level of each gene was measured as the relative expression level to the expression level of the SDHA gene. As a result, each was: KCNAB1 gene: 0.03, SULT1E1 gene: 0.05, MN1 gene: 0.69, or RARRES2 gene: 0.41.

Step 1-6: Karyotypic Analysis for Amniotic Adherent Stem Cells

The third- and fifth-passage amniotic adherent stem cells cultured by the above culture method were subjected to karyotypic analysis by the G band method, which was entrusted to and performed by NIHON GENE RESEARCH LABORATORIES Inc. The third- and fifth-passage cells frozen were thawed and inoculated each in two T25 flasks at a density of about 8,000 cells/cm$^2$. αMEM (5 mL) comprising 10% (final concentration) fetal bovine serum (FBS) and 10 ng/mL (final concentration) basic fibroblast growth factor (bFGF) was added and then culture was carried out for 24 hours. Thereafter, the T25 flasks were each filled with αMEM comprising 10% (final concentration) fetal bovine serum (FBS) and 10 ng/mL (final concentration) basic fibroblast growth factor (bFGF) and transported at room temperature to NIHON GENE RESEARCH LABORATORIES Inc. (Sendai, Miyagi Prefecture). In NIHON GENE RESEARCH LABORATORIES Inc., 20 cells were arbitrarily collected and chromosomes were taken out from the cells and subjected to differential staining. Based on the band patterns characteristic to individual chromosomes, the chromosomes were identified and analyzed for the presence or absence of karyotypic abnormality such as aneuploidy or translocation. As a result, karyotypic abnormality was observed in either one of the third- and fifth-passage cells. Specifically, in the third-passage cells, karyotypic abnormality was found in one out of 20 cells, an isochromosome of a long arm of the 2nd chromosome increased (+i(2)(q10)). In the fifth-passage cells, karyotypic abnormality was found in 5 out of 20 cells and trisomy in the second chromosome was observed in all 5 cells.

Example 1

Step 2-1: Collection of Amnion

Amnion was collected in the same manner as in Comparative Example 1.

Step 2-2: Enzymatic Treatment of Amnion and Collection of Amniotic Adherent Stem Cells A cell population comprising amniotic adherent stem cells was collected in the same manner as in Comparative Example 1.

Step 2-3: Culture of Amniotic Adherent Stem Cells

The cell population comprising amniotic adherent stem cells which is obtained in the above section "Enzymatic treatment of amnion and collection of amniotic adherent stem cells" was inoculated at a density of 6,000 cells/cm$^2$ in CellSTACK (registered trademark) and adhesion cultured in αMEM comprising 5% (final concentration) human platelet lysate (hPL) until subconfluence. Thereafter, zero-th passage cells were dissociated by TrypLE Select and a ⅕ amount of the cells was inoculated in the CellSTACK (registered trademark) at the same scale as that of the previous culture and subcultured. Medium replacement was carried out at a frequency of once every 2 to 4 days. The first-passage cells that reached subconfluence were dissociated by using TrypLE Select and RPMI1640 was added so as to obtain a cell concentration of 2×10$^7$ cells/mL. To this, the same amount of CP-1 (registered trademark) solution, which is a solution comprising CP-1 (registered trademark) and 25% human serum albumin in a ratio of 34:16, was added, and transferred to cryovials in an amount of 1 mL per vial, gradually frozen up to −80° C. and then cryopreserved a day in liquid nitrogen. Thereafter, the second-passage cells were thawed and inoculated at a density of about 15,000 to 18,000 cells/cm$^2$ in CellSTACK (registered trademark) and adherent cultured in αMEM comprising 5% (final concentration) human platelet lysate (hPL), until subconfluence. Thereafter, the second-passage cells were dissociated by using TrypLE Select. A ⅕ amount of the cells was inoculated in the CellSTACK (registered trademark) at the same scale as that of the previous culture and subcultured. Medium replacement was carried out at a frequency of once every 2 to 4 days. The third-passage cells that reached subconfluence were dissociated by using TrypLE Select and RPMI1640 was added so as to obtain a cell concentration of 4×10$^6$ cells/mL. To this, the same amount of a CP-1 (registered trademark) solution, which is a solution comprising CP-1 (registered trademark) and 25% human serum albumin in a ratio of 34:16, was added, transferred to cryovials in an amount of 1 mL per vial, gradually frozen up to −80° C. and then cryopreserved a day in liquid nitrogen. Thereafter, the fourth-passage cells were thawed and inoculated at a density of about 6,000 cells/cm$^2$ in CellSTACK (registered trademark) and adherent cultured in αMEM comprising 5% (final concentration) human platelet lysate (hPL), until subconfluence. Thereafter, the fourth-passage cells were dissociated by using TrypLE Select. A ⅕ amount of the cells was inoculated in the CellSTACK (registered trademark) at the same scale as that of the previous culture and subcultured. Medium replacement was carried out at a frequency of once every 2 to 4 days. The fifth-passage cells that reached subconfluence were dissociated by using TrypLE Select and RPMI1640 was added so as to obtain a cell concentration of 4×10⁶ cells/mL. To this, the same amount of a CP-1 (registered trademark) solution, which is a solution comprising CP-1 (registered trademark) and 25% human serum albumin in a ratio of 34:16, was added, transferred to cryovials in an amount of 1 mL per vial, gradually frozen up to −80° C. and cryopreserved in liquid nitrogen. In all cell populations on and after the sixth-passage, cells were inoculated at a density of about 6,000 cells/cm² in CellSTACK (registered trademark) and adherent cultured in αMEM comprising 5% (final concentration) human platelet lysate (hPL), until subconfluence. Thereafter, the resultant cell population was dissociated by using TrypLE Select and subcultured. This operation was repeated up to the ninth passage.

Step 2-4: Analysis for Antigen of Amniotic Adherent Stem Cells

For the fifth-passage amniotic adherent stem cells cultured by the above culture method, individual surface antigens (CD73 positive rate, CD90 positive rate, CD105 positive rate, CD166 positive rate, CD45 negative rate, CD34 negative rate, and CD326 negative rate) were analyzed by a flow cytometer. As a result, the CD73, CD90 and CD105 positive rates were all 50% or more (specifically, CD73: 99%, CD90: 100%, CD105: 100%); and the CD166 positive rates were all 30% or more (specifically, CD166: 100%). The CD45, CD34 and CD326 negative rates were all 95% or more (specifically, CD45: 100%, CD34: 100%, CD326: 100%). From the results, it was confirmed that the cells cultured by the above culture method are adherent stem cells.

Additionally, for the amniotic adherent stem cells of the third- and fifth-passage cultured by the above culture method, the proportion of KCNAB1 antigen-positive cells was analyzed by a flow cytometer. The proportion of the cells in either one of the passages was 85% or more (the third passage: 91%, the fifth passage: 90%). Accordingly, it was found that the fifth-passage amniotic adherent stem cells of Example 1 satisfy the condition: the proportion of KCNAB1-positive adherent stem cells is 85% or more.

Note that, the method and reagents of the measurement herein is the same as in Comparative Example 1.

Step 2-5: Gene Expression Analysis for Amniotic Adherent Stem Cells

For the amniotic adherent stem cells of the fifth-passage cultured by the above culture method, expression analysis of genes (KCNAB1 gene, SULT1E1 gene, MN1 gene, RARRES2 gene) by a microarray was entrusted to and performed by RIKEN GENESIS Co., Ltd.

The microarray analysis was carried out in the same manner as in Comparative Example 1. The expression level of each gene was measured as the relative expression level to the expression level of the SDHA gene. As a result, each was: KCNAB1 gene: 0.44, SULT1E1 gene: 0.68, MN1 gene: 1.77, or RARRES2 gene: 0.003.

Step 2-6: Karyotypic Analysis for Amniotic Adherent Stem Cells

The third- and fifth-passage amniotic adherent stem cells cultured by the above culture method were subjected to karyotypic analysis by the G band method, which was entrusted to and performed by NIHON GENE RESEARCH LABORATORIES Inc. The third- and fifth-passage cells frozen were thawed and inoculated each in two T25 flasks at a density of about 8,000 cells/cm². αMEM (5 mL) comprising 5% (final concentration) human platelet lysate (hPL) was added and then culture was carried out for 24 hours. Thereafter, the T25 flasks were each filled with αMEM comprising 5% (final concentration) human platelet lysate (hPL) and transported at room temperature to NIHON GENE RESEARCH LABORATORIES Inc. (Sendai, Miyagi Prefecture). In NIHON GENE RESEARCH LABORATORIES Inc., 20 cells were arbitrarily collected and chromosomes were taken out from the cells and subjected to differential staining. Based on the band patterns characteristic to individual chromosomes, the chromosomes were identified and analyzed for the presence or absence of karyotypic abnormality such as aneuploidy or translocation. As a result, all of the third- and fifth-passage cells maintained a normal karyotype.

In Table 1, the positive rates of KCNAB1 and karyotypic analysis results in Comparative Example 1 and Example 1 are collectively shown.

TABLE 1

Positive rates of KCNAB1 and karyotypic analysis results in Example and Comparative Example

| | Number of passages | Positive rate of KCNAB1 | Positive rate of KCNAB1 |
|---|---|---|---|
| Comparative Example 1 | P3 | 78% | One out of 20 cells is karyotypic abnormal (an increase of isochromosome of a long arm of the 2nd chromosome (+i(2)(q10))) |
| | P5 | 81% | Five out of 20 cells are karyotypic abnormal (five cells all have trisomy of the second chromosome) |
| Example 1 | P3 | 91% | 20 cells all have normal karyotype |
| | P5 | 90% | 20 cells all have normal karyotype |

From the above results, it was found that a cell population satisfying a positive rate of KCNAB1 of 85% or more maintains a normal karyotype. It was suggested that the condition: a positive rate of KCNAB1 is 85% or more, is effective as an index for obtaining a cell population comprising adherent stem cells maintaining a normal karyotype. In other words, according to the present invention, a cell population comprising adherent stem cells maintaining a normal karyotype can be obtained by using the condition: a positive rate of KCNAB1 is 85% or more, as an index. This enables production of a safe cell preparation suitable for clinical use.

In addition, if the condition: a positive rate of KCNAB1 is 85% or more, is used as an index, the karyotype stability of a biological sample can be evaluated (determined and/or predicted) without performing karyotype analysis requiring an evaluation period of usually about a month.

Further, according to the present invention, in a cell population comprising adherent stem cells, if the condition: a positive rate of KCNAB1 is 85% or more, is used as an index, karyotype stability of a biological sample (the presence or absence of karyotypic abnormality of the adherent stem cells) can be monitored over time simply in a short time. This enables reduction of the cost and period required for quality evaluation of a biological sample, leading to a reduction of manufacturing cost for cell preparations.

Example 2

A fetal membrane and a placenta, which are fetal appendages, were aseptically collected from pregnant women (two donors #1 and #2 different from those in Comparative Example 1 and Example 1) of an elective cesarean section case after obtaining informed consent. Individual fetal appendages were treated in accordance with "Step 1-1: Collection of amnion" and "Step 1-2: Enzymatic treatment of amnion and collection of amniotic adherent stem cells" to obtain amniotic adherent stem cells.

The cell populations comprising amnion adherent stem cells obtained from #1 and #2 donors were cultured by the method of "Example 1: Culture for amniotic adherent stem cells" to obtain the fifth-passage cell population.

For the amniotic adherent stem cells cultured by the above culture method, the proportion of KCNAB1-positive cells can be analyzed by a flow cytometer in the same manner as in "Step 1-4: Antigen analysis for amniotic adherent stem cells". The KCNAB1 positive rate of donor #1 was 85% or more (specifically, #1: 94%) and that of donor #2 was less than 85% (specifically, 49%). Also, with respect to the amniotic adherent stem cells cultured by the above culture method, karyotype can be analyzed in the same manner as in "Step 1-6: Karyotypic analysis for amniotic adherent stem cells". As a result of the karyotypic analysis, all cells of donor #1 maintained a normal karyotype; whereas karyotypic abnormality was observed in the cells of donor #2 (specifically, karyotypic abnormality, which was a structural abnormality of chromosome 13 (add(13)(p11.2)), was found in one out of 20 cells).

In Table 2, the KCNAB1 positive rate and results of karyotypic analysis in Example 2 are collectively shown.

TABLE 2

KCNAB1 positive rate and karyotypic analysis results in Example 2

|  |  | Positive rate of KCNAB1 | Karyotypic analysis results |
| --- | --- | --- | --- |
| Example 2 | #1 | 94% | 20 cells all have normal karyotype |
|  | #2 | 49% | One out of 20 cells has karyotypic abnormality (structural abnormality of chromosome 13 (add(13)(p11.2))) |

Example 3

In Example 3, amniotic adherent stem cells were obtained from different donors and using different enzymatic treatment conditions and culture conditions from those in Comparative Example 1, Example 1 and, Example 2. A fetal membrane and a placenta, which are fetal appendages, were aseptically collected from pregnant women (three donors #3 to #5 different from those in Comparative Example 1, Example 1 and Example 2) of an elective cesarean section case after obtaining informed consent.

Step 3-1: Collection of Amnion

The amnion was obtained in the same manner as in Comparative Example 1.

Step 3-2: Enzymatic Treatment of Amnion and Collection of Amniotic Adherent Stem Cells The amnion was enzymatically treated by immersing the amnion comprising an epithelial cell layer and an adherent stem cell layer in a Hank's balanced salt solution (comprising Ca and Mg) comprising 480 PU/mL collagenase and 400 PU/mL dispase I, and shaking/stirring under conditions of 37° C., 90 minutes, and 50 rpm. The solution after enzymatic treatment was filtered through a nylon mesh having openings of 95 μm to remove undigested products of the amnion to collect a cell suspension comprising amniotic adherent stem cells.

Step 3-3: Culture of Amniotic Adherent Stem Cells

The cell population comprising amnion adherent stem cells obtained in the above section "Enzymatic treatment of amnion and collection of amniotic adherent stem cells" was inoculated at a density of 1,000 cells/cm$^2$ to CellSTACK (registered trademark) and adherent cultured in a MEM comprising a 5% (final concentration) human platelet lysate (hPL) until subconfluence. Medium replacement was carried out at a frequency of once every 3 to 5 days. Thereafter, the zero-th passage cells were dissociated by using TrypLE Select and physiological saline was added so as to obtain a cell concentration of 2×10$^7$ cells/mL. To this, the same amount of a CP-1 (registered trademark) solution (a solution prepared by mixing CP-1 (registered trademark) and 25% human serum albumin in a ratio of 34:16) was added. The resultant mixture was transferred to cryovials in an amount of 1 ml per vial, gradually frozen up to −80° C. and then cryopreserved one day in liquid nitrogen. Thereafter, the first-passage cells were thawed and inoculated at a density of about 1,000 cells/cm$^2$ in CellSTACK (registered trademark) and adherent cultured for 5 days in a MEM comprising a 5% (final concentration) human platelet lysate (hPL) until subconfluence. Thereafter, the first-passage cells were dissociated by TrypLE Select and physiological saline was added so as to obtain a cell concentration of 2×10$^7$ cells/mL. To this, the same amount of a CP-1 (registered trademark) solution (a solution prepared by mixing CP-1 (registered trademark) and 25% human serum albumin in a ratio of 34:16) was added. The resultant mixture was transferred to cryovials in an amount of 1 ml per vial, gradually frozen up to −80° C. and then cryopreserved one day in liquid nitrogen. Thereafter, the second-passage cells were thawed and inoculated at a density of about 1,000 cells/cm$^2$ in CellSTACK (registered trademark) and adherent cultured for 5 days in a MEM comprising a 5% (final concentration) human platelet lysate (hPL) until subconfluence. Thereafter, the second-passage cells were dissociated by TrypLE Select and physiological saline was added so as to obtain a cell concentration of 4×10$^6$ cells/mL. To this, the same amount of a CP-1 (registered trademark) solution (a solution prepared by mixing CP-1 (registered trademark) and 25% human serum albumin in a ratio of 34:16) was added. The resultant mixture was transferred to cryovials in an amount of 1 ml per vial, gradually frozen up to −80° C. and then cryopreserved in liquid nitrogen.

Step 3-4: Analysis for Antigen of Amniotic Adherent Stem Cells

Individual surface antigens (CD73 positive rate, CD90 positive rate, CD105 positive rate, CD166 positive rate, CD45 negative rate, CD34 negative rate, CD326 negative rate) of the second-passage amniotic adherent stem cells cultured by the above culture method were analyzed by a flow cytometer. As a result, CD73, CD90 and CD105 positive rates were all 50% or more (specifically, #3 to #5 were all 100%). CD166 positive rates were all 30% or more (specifically, #3: 99%, #4: 100%, #5: 99%). CD45, CD34 and CD326 negative rates were all 95% or more (specifically, #3: 99%, #4: 100%, #5: 100%). From the results, it was confirmed that the cells cultured by the above culture method are adherent stem cells.

The proportion of the cells positive for KCNAB1 antigen in the second-passage amniotic adherent stem cells cultured by the above culture method was analyzed by a flow cytometer. As a result, in any one of the donors, the proportion was 85% or more (#3: 98.2%, #4: 99.9%, #5: 99.7%). Thus, it was found that the second-passage amniotic adherent stem cells in Example 3 derived from all donors (#3 to #5) satisfy the condition: the proportion of KCNAB1-positive adherent stem cells is 85% or more. Note that, the methods and reagents used herein are the same as in those of Comparative Example 1.

Step 3-5: Gene Expression Analysis of Amniotic Adherent Stem Cells

For the second-passage amniotic adherent stem cells cultured in the above culture method, expression analysis of genes (KCNAB1 gene, SULT1E1 gene, MN1 gene, RARRES2 gene) by a microarray was entrusted to and performed by RIKEN GENESIS Co., Ltd.

Microarray analysis was carried out in the same manner as in Comparative Example 1. The expression level of each gene was measured as the relative expression level to the expression level of the SDHA gene. As a result, each was: in #3, KCNAB1 gene: 0.15, SULT1E1 gene: 0.36, MN1 gene: 0.81 and RARRES2 gene: 0.01; in #4, KCNAB1 gene: 0.07, SULT1E1 gene: 0.16, MN1 gene: 0.75 and RARRES2 gene: 0.001; and in #5, KCNAB1 gene: 0.11, SULT1E1 gene: 0.27, MN1 gene: 1.38 or RARRES2 gene: 0.001.

Further, for the second-passage amniotic adherent stem cells cultured by the above culture method, expression analysis of genes (KCNAB1 gene, SULT1E1 gene, MN1 gene, RARRES2 gene) by quantitative PCR was carried out in accordance with the following procedures (1) to (4).

(1) A cryopreserved cell population was thawed and centrifugally collected. The collected cell population was washed with phosphate buffer (PBS) and centrifugally collected. Thereafter, total RNA was extracted and purified by RNeasy Plus Mini kit (manufactured by QIAGEN).

(2) To the purified total RNA, ReverTra Ace qPCR RT Master Mix (manufactured by Toyobo Co., Ltd.) was added. Using the purified total RNA as a template, cDNA is synthesized by reverse transcription.

(3) Synthesized cDNA, Taqman Fast Advanced Master Mix (manufactured by Applied Biosystems), and primers (Taqman Gene Expression Assay, manufactured by Thermo Fisher, SDHA primer Assay ID: Hs00188166_m1; KCNAB1 primer Assay ID: Hs00185764_m1; SULT1E1 primer Assay ID: Hs00960938_m1; MN1 primer Assay ID: Hs00159202_m1; RARRES2 primer Assay ID: Hs00414615_m1) were mixed and poured in a 96-well plate and quantitative PCR was carried out.

(4) ΔCt values of individual samples to SDHA were analyzed by StepOnePlus Real-Time PCR System (manufactured by Applied Biosystems) to calculate the relative expression levels (2^(−ΔCt)) of individual genes to the expression level of SDHA gene in each cell. As a result, each was: in #3, KCNAB1 gene: 0.77, SULT1E1 gene: 0.37 and MN1 gene: 1.1, RARRES2 gene: 0.0026; in #4, KCNAB1 gene: 0.72, SULT1E1 gene: 0.13, MN1 gene: 1.8 and RARRES2 gene: 0.0029; and in #5, KCNAB1 gene: 4.4, SULT1E1 gene: 0.50, MN1 gene: 5.9, or RARRES2 gene: 0.0033.

Step 3-6: Analysis for Karyotype of Amniotic Adherent Stem Cells

The second-passage amniotic adherent stem cells cultured by the above culture method were subjected to karyotypic analysis by the G band method, which was entrusted to and performed by NIHON GENE RESEARCH LABORATORIES Inc. The second-passage cells frozen were thawed and inoculated in two T25 flasks at a density of about 8,000 cells/cm². αMEM (5 mL) comprising 5% (final concentration) human platelet lysate (hPL) was added and culture was carried out for 24 hours. Thereafter, the T25 flasks was each filled with αMEM comprising a 5% (final concentration) human platelet lysate (hPL) and transported at room temperature to NIHON GENE RESEARCH LABORATORIES Inc. (Sendai, Miyagi Prefecture). In NIHON GENE RESEARCH LABORATORIES Inc., 20 cells were arbitrarily collected and chromosomes were taken out from the cells and subjected to differential staining. Based on the band patterns characteristic to individual chromosomes, the chromosomes were identified and analyzed for the presence or absence of karyotypic abnormality such as aneuploidy or translocation. As a result, all second-passage cells maintained a normal karyotype.

From the results, it was found that a cell population satisfying the condition: a positive rate of KCNAB1 is 85% or more, maintains a normal karyotype. It was suggested that even if amniotic adherent stem cells are collected from the amnion and cultured by different methods, if a KCNAB1 positive rate is measured and found to satisfy 85% or more, the quality of a donor itself and a biological sample collected from a donor can be evaluated. In other words, according to the present invention, a biological sample having a high content of amniotic adherent stem cells having no karyotypic abnormality can be screened (donor screening) by using the condition: a KCNAB1 positive rate is 85% or more, as an index. Furthermore, enzymatic treatment conditions and culture conditions can be optimized (improvement of enzymatic treatment conditions/culture conditions) by using the condition: a KCNAB1 positive rate is 85% or more as an index. This enables shortening the period of quality evaluation and reduction of the period required for improvement of production method including enzymatic treatment conditions and culture conditions.

Example 4

A part of the amniotic adherent stem cells obtained in Example 1 was subjected to preparation of a pharmaceutical composition. A pharmaceutical composition (cell preparation) comprising amniotic adherent stem cells (2.0×10⁸ cells), 6.8 mL of CP-1 solution (registered trademark), 3.2 mL of 25% human serum albumin solution, and 10 mL of RPMI1640 medium is prepared. The pharmaceutical composition was placed in a freezing bag and stored in a frozen state. Note that, the pharmaceutical composition can be thawed upon use and applied to a patient.

Reference Example

Step 4-1: Culture of Bone Marrow-Derived Mesenchymal Stem Cells

Human bone marrow-derived mesenchymal stem cells (hMSC mesenchymal stem cells, manufactured by Lonza) taken from 3 donors (#6 to #8) were purchased, each thawed and inoculated at a density of 6,000 cells/cm$^2$ in a φ15-cm dish and adhesion cultured in a medium specially manufactured by Lonza, until subconfluence. Medium replacement was carried out at a frequency of once every 3 to 5 days. Thereafter, cells were dissociated by using TrypLE Select and physiological saline was added so as to obtain a cell concentration of 2×10$^6$ cells/mL. To this, the same amount of a CP-1 (registered trademark) solution (a solution prepared by mixing CP-1 (registered trademark) and 25% human serum albumin in a ratio of 34:16) was added. The resultant mixture was transferred to cryovials in an amount of 1 ml per vial, gradually frozen up to −80° C. and then cryopreserved in liquid nitrogen.

Step 4-2: Analysis for Antigen of Bone Marrow-Derived Mesenchymal Stem Cells Individual surface antigens (CD73 positive rate, CD90 positive rate, CD105 positive rate, CD166 positive rate, CD45 negative rate, CD34 negative rate, CD326 negative rate) of the bone marrow-derived mesenchymal stem cells cultured by the above culture method were analyzed by a flow cytometer. As a result, CD73, CD90 and CD105 positive rates were all 50% or more. CD166 positive rates were all 30% or more. CD45, CD34 and CD326 positive rates were all less than 5%.

Further, the proportion of the cells positive for KCNAB1 antigen was analyzed by a flow cytometer. As a result, in any one of the donors, the proportion was less than 85% (#6: 66%, #7: 71%, #8: 57%). Note that, the methods and reagents used herein are the same as in those of Comparative Example 1.

Step 4-3: Gene Expression Analysis of Bone Marrow-Derived Mesenchymal Stem Cells For the bone marrow-derived mesenchymal stem cells cultured by the above culture method, expression analysis of genes (KCNAB1 gene, SULT1E1 gene, MN1 gene, RARRES2 gene) was carried out by quantitative PCR. As a result, each was; in #6, KCNAB1 gene: 0.0015, SULT1E1 gene: not detected because the expression level was extremely low, MN1 gene: 0.54 or, RARRES2 gene: 0.0026; in #7, KCNAB1 gene: 0.0020, SULT1E1 gene: not detected because the expression level was extremely low, MN1 gene: 0.90 or RARRES2 gene: 0.0029; or in #8, KCNAB1 gene: 0.0033, SULT1E1 gene: not detected because the expression level was extremely low, MN1 gene: 0.52 or RARRES2 gene: 0.0033. Note that, the method and reagents used herein is the same as in Example 3.

In Table 3, the results of quantitative PCR gene expression analysis in Example 3 and Reference Example are collectively shown.

TABLE 3

The results of quantitative PCR gene expression analysis and flowcytometric analysis of Example 3 and Reference Example

| | | Quantitative PCR gene expression analysis | | | | Flow cytometric analysis |
|---|---|---|---|---|---|---|
| | | KCNA81 | SULT1E1 | MN1 | RARRES2 | KCNA81 |
| Example 3 | #3 | 0.77 | 0.37 | 1.1 | 0.0026 | 98% |
| | #4 | 0.72 | 0.13 | 1.8 | 0.0029 | 100% |
| | #5 | 4.4 | 0.50 | 5.9 | 0.0033 | 100% |
| Reference Example | #6 | 0.0015 | Not detected | 0.54 | 0.0026 | 66% |
| | #7 | 0.0020 | Not detected | 0.90 | 0.0029 | 71% |
| | #8 | 0.0033 | Not detected | 0.52 | 0.0033 | 57% |

The invention claimed is:

1. A method for producing a cell population comprising adherent stem cells, comprising:
   obtaining fetal membrane and placenta from a female patient;
   manually separating amnion from the stump of the fetal membrane;
   enzymatically treating the amnion comprising epithelial cell layer and adherent stem cell layer to collect amniotic adherent stem cells;
   culturing the enzymatically treated and collected amniotic adherent stem cells derived from a fetal appendage in a medium comprising human platelet lysate (hPL) and obtaining a cultured cell population;
   measuring a proportion of potassium channel, voltage gated subfamily A regulatory beta subunit 1-positive (KCNAB1-positive) of the cultured cell population;
   identifying a cell population comprising adherent stem cells maintaining a normal karyotype by using the proportion of KCNAB1-positive adherent stem cells being 85% or more in as an index to obtain an identified cell population; and
   obtaining the identified cell population identified by using said index which comprise adherent stem cells maintaining a normal karyotype by using the proportion of KCNAB1-positive adherent stem cells being 85% or more.

2. A method according to claim 1, wherein the obtained cell population has 90% or more KCNAB1-positive adherent stem cells.

3. A method according to claim 1, wherein the number of passages is five or more in the culturing step.

4. A method according to claim 1, further comprising a step of selectively separating the identified cell population.

5. A method according to claim 1, where the fetal membrane and placenta are obtained from a female patient after a cesarean section.

6. A method for producing a cell population comprising adherent stem cells, comprising:
   culturing enzymatically treated and collected amniotic adherent stem cells derived from an amnion, which are obtained from fetal membrane and placenta from a female patient, wherein amnion is manually separated from the stump of the fetal membrane, and the amnion comprising epithelial cell layer and adherent stem cell layer is enzymatically treated to collect amniotic adherent stem cells, in a medium comprising human platelet lysate (hPL); and
   obtaining a cell population having 85% or more potassium channel, voltage gated subfamily A regulatory beta subunit 1-positive (KCNAB1-positive) adherent stem cells.

7. A method according to claim 6, wherein the obtained cell population has 90% or more KCNAB1-positive adherent stem cells.

8. A method according to claim 6, wherein the number of passages is five or more in the culturing step.

9. A method according to claim 6, where the fetal membrane and placenta are obtained from a female patient after a cesarean section.

* * * * *